(12) United States Patent
Ibrahim et al.

(10) Patent No.: US 7,901,440 B2
(45) Date of Patent: Mar. 8, 2011

(54) METHOD OF COMPRESSING ADJACENT PIECES OF BONE

(75) Inventors: Zaki G. Ibrahim, Greenwood Village, CO (US); Theodore P. Bertele, Longmont, CO (US)

(73) Assignee: IB Medical, LLC, Longmont, CO (US)

( * ) Notice: Subject to any disclaimer, the term of this patent is extended or adjusted under 35 U.S.C. 154(b) by 0 days.

(21) Appl. No.: 12/694,179

(22) Filed: Jan. 26, 2010

(65) Prior Publication Data

US 2010/0114176 A1  May 6, 2010

Related U.S. Application Data

(63) Continuation of application No. 12/522,147, filed as application No. PCT/US2007/006830 on Mar. 20, 2007.

(60) Provisional application No. 60/788,607, filed on Apr. 3, 2006.

(51) Int. Cl.
*A61B 17/66* (2006.01)

(52) U.S. Cl. .......................................... 606/282

(58) Field of Classification Search ............... 606/57, 606/60, 90, 105, 70, 71, 246, 279–299
See application file for complete search history.

(56) References Cited

U.S. PATENT DOCUMENTS

| | | | |
|---|---|---|---|
| 5,154,485 | A | 10/1992 | Fleishman |
| 6,306,136 | B1 | 10/2001 | Baccelli |
| 6,802,844 | B2 | 10/2004 | Ferree |
| 7,041,105 | B2 * | 5/2006 | Michelson ............... 606/70 |
| 7,112,202 | B2 | 9/2006 | Michelson |
| 2003/0130661 | A1 | 7/2003 | Osman |
| 2003/0212399 | A1 | 11/2003 | Dinh et al. |
| 2004/0019353 | A1 | 1/2004 | Freid et al. |
| 2004/0153069 | A1 | 8/2004 | Paul |
| 2004/0210217 | A1 | 10/2004 | Baynham et al. |

(Continued)

OTHER PUBLICATIONS

International Application No. PCT/US07/06830, International Search Report & Written Opinion mailed May 20, 2008, 18 pages.

*Primary Examiner* — Anu Ramana
(74) *Attorney, Agent, or Firm* — Lathrop & Gage LLP

(57) ABSTRACT

A Static Compression Device (SC device) for active, measurable compression of a fusion graft by the surgeon at the time of surgery is disclosed. The SC device is attachable to adjacent vertebral bodies or other pieces of bone and has a device that applies compressive force to the adjacent vertebral bodies or pieces of bone to assist fusion according to Wolff's law. The SC device has a locking mechanism that maintains the compression applied at surgery, but prevents further compression (settling) from occurring after surgery. The SC device allows the surgeon the ability to compress a segment, measure the applied compression, and lock the segment in the compressed position. In one embodiment of the invention, the pressure is applied to the SC device through a compression device that applies a desired and measurable amount of force. In this embodiment, the combination of the SC device with a pressure applying and measuring device allows the surgeon more control over the force applied to a cervical, thoracic or lumbar implant than has previously been available. In the preferred embodiment, the SC device compresses two or more adjacent vertebrae across an adjacent bone graft to facilitate fusion of these vertebrae to treat pain produced by pressure from the disks between such vertebrae bulging and resulting in contact with and pressure on the spinal cord and adjacent nerve roots. In other embodiments, the SC device may be used to apply measurable compression across any type of bony interface (e.g. fractures) to facilitate union.

12 Claims, 50 Drawing Sheets

U.S. PATENT DOCUMENTS

2005/0027359 A1 2/2005 Mashburn
2006/0235427 A1 10/2006 Thomas et al.
2007/0244488 A1 10/2007 Metzger et al.
2008/0147125 A1 6/2008 Colleran et al.

* cited by examiner

METHOD OF COMPRESSING ADJACENT PIECES OF BONE

RELATED APPLICATIONS

This application is a Continuation of application Ser. No. 12/522,147, which is a US 371 National Stage Entry of PCT/US07/06830 filed Mar. 20, 2007 which claims the benefit of priority from Provisional Application Ser. No. 60/788,607 filed Apr. 3, 2006. Each of the aforementioned applications is incorporated herein by reference.

BACKGROUND OF THE INVENTION

1. Field of the Invention

The present invention is directed to devices and methods to compress two or more adjacent S vertebrae across an adjacent bone graft to facilitate fusion of these vertebrae to treat pain produced by pressure from the disks between such vertebrae bulging and resulting in contact with and pressure on the spinal cord and adjacent nerve roots.

2. Description of Related Art

For nearly half a century, anterior cervical discectomy and fusion has been performed for individuals complaining of intractable upper extremity pain due to cervical disc herniation or bone spurs at single or multiple levels. This procedure has undergone several significant modifications since its inception. The introduction of the Smith-Robinson technique of using tricortical iliac crest bone graft, the technique of denuding vertebral endplates of cartilage described by Zdeblick et al., and the present use of cervical plates have all represented significant technical advances which have increased fusion rates and improved patient outcomes. Currently it is possible to expect greater than 85% good or excellent outcomes for individuals with appropriate indications who undergo this surgical procedure.

However, several problems remain. Although fusion rates for one level anterior cervical fusion with autograft (patient's own bone) may approach 95%, these rates decrease significantly for each additional level incorporated in the fusion. Additionally, using autograft bone typically involves the use of a second incision, which significantly increases patient morbidity. Allograft bone (bone from another human) is a viable option, but has considerably lower fusion rates than autograft and is generally not considered a good choice in multiple level fusion surgery.

The use of anterior cervical plates has been credited with increasing fusion rates in multiple level fusions. It is thought that the immediate stability provided by the plate provides a more favorable environment for fusion to occur. The vast majority of plates on the market provide for static stabilization of the vertebral body-graft construct (no compression, no dynamization). More recently dynamic plates have been introduced. These plates provide for passive dynamic compression of the vertebral body-graft construct. This compression occurs postoperatively when the weight of the patient's head loads the construct, allowing for passive compression of the graft to occur. Wolff's law (The concept that bone heals best under compression) suggests that the use of dynamic compression plates should lead to increased fusion rates. However, this has not been found to be the case. Several studies have indicated that dynamic compression plates do not lead to higher fusion rates than static plates. In addition, the possibility of uncontrolled settling over time which may lead to kyphosis (reversal of the normal curvature of the neck) has caused these plates to fall out of favor with many surgeons.

Wolff's law is a well-accepted orthopedic principle, championed and reported in the trauma literature by the Swiss AO Foundation, a non-profit surgeon-driven organization dedicated to progress in research, development, and education in the field of trauma and corrective surgery. Several studies have shown that long bones heal best under rigid compression. This has lead to the development of special compression plates that are currently widely used in surgical techniques of open reduction and internal fixation of fractures.

It is believed that there is no plate on the market that truly invokes Wolff's law in spinal fusion surgery by providing rigid static loading of the graft-vertebral body construct. Mechanisms for achieving compression on adjacent vertebrae are known. But, most of these devices either utilize compression across individual screws (risking cut out due to lessened surface area) or attempt to achieve compression prior to the plate being applied (making this a cumbersome technique).

SUMMARY OF THE INVENTION

The Static Compression Device (SC device) of the present invention allows for active, measurable compression of a fusion graft by the surgeon at the time of surgery. The SC device is attachable to adjacent vertebral bodies or other pieces of bone and has a device that applies compressive force to the adjacent vertebral bodies or other pieces of bone to assist fusion according to Wolff's law. The SC device has a locking mechanism that maintains the compression applied at surgery, but prevents further compression (settling) from occurring after surgery. So, the SC device allows the surgeon the ability to compress a segment or other adjacent pieces of bone, measure the applied compression, and to lock the segment or pieces of bone in the compressed position. In one embodiment of the invention, the pressure is applied to the SC device through a compression device that applies a desired and measurable amount of force. In this embodiment, the combination of the SC device with a pressure applying and measuring device allows the surgeon more control over the force applied to a cervical, lumbar or thoracic implant or implant applied to other pieces of bone than has previously been available. The SC device of the present invention in one embodiment compresses two or more adjacent vertebrae across an adjacent bone graft to facilitate fusion of these vertebrae to treat pain produced by pressure from the disks between such vertebrae, adjacent bone spurs or both bulging and resulting in contact with and pressure on the spinal cord and adjacent nerve roots or any other disorder of the spine. The vertebrae may be in the cervical, thoracic or lumbar spine. In fact, in various embodiments, the SC device may be used to apply measurable compression across any type of bony interface (e.g. fractures) to facilitate union.

The SC device has four unique characteristics which together provide for static compression of the vertebral body-graft interface:

The use of fixed angle screws to secure the SC device to the vertebral bodies;

The use of a compression device to apply and measure the pressure applied to the vertebral bodies by the SC device;

The technique of using active, static compression to assist the fusion process; and The use of a locking mechanism that maintains compression during the fusion process to facilitate bone growth.

This SC device differs from currently known static plates by providing controlled loading (compression) of the graft at the time of surgery. The SC device also differs from currently known dynamic plates in that the compression achieved is "static" (rigid) and prevents further "dynamic" settling from occurring after the procedure is completed. The resulting major advantage of the SC device over previously known S devices is that the SC device may significantly increase fusion rates (especially in multiple level cervical fusion) and maintain the anatomy of the cervical spine (preventing excessive compression leading to kyphosis). In fact, it is believed that using the SC device to provide static loading at each level in multiple level fusions may allow the use of allograft bone to approach fusion rates now only attainable by using autograft techniques. The invention will be described hereafter in detail with particular reference to the drawings.

Throughout this description, like elements, in whatever embodiment described, refer to common elements wherever referred to and referenced by the same reference number. The characteristics, attributes, functions, interrelations ascribed to a particular element in one location apply to that element when referred to by the same reference number in another location unless specifically stated otherwise.

DETAILED DESCRIPTION OF THE INVENTION

Figure 1:
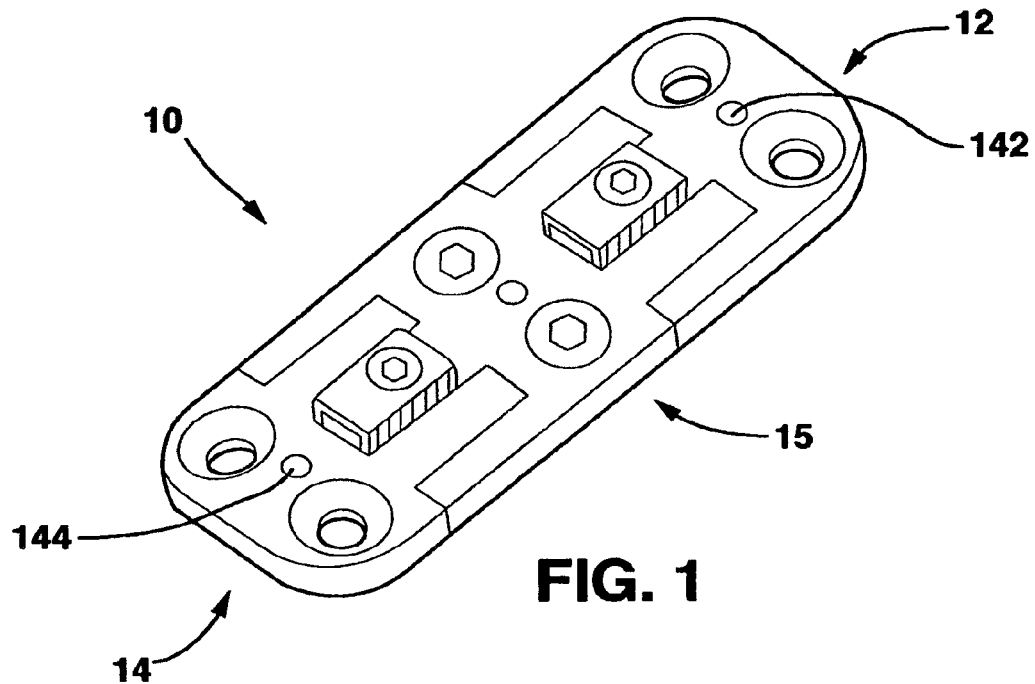
FIG. 1 is a perspective view of one embodiment of the static compression device of the present invention.
Figure 2:
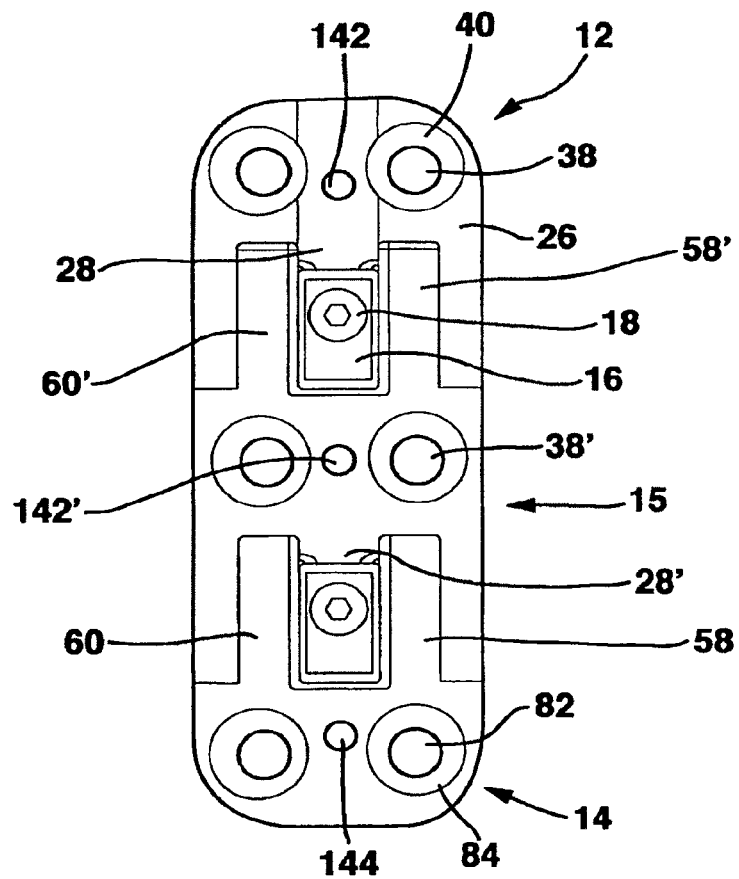
FIG. 2 is a top view of the static compression device of FIG. 1.
Figure 3:
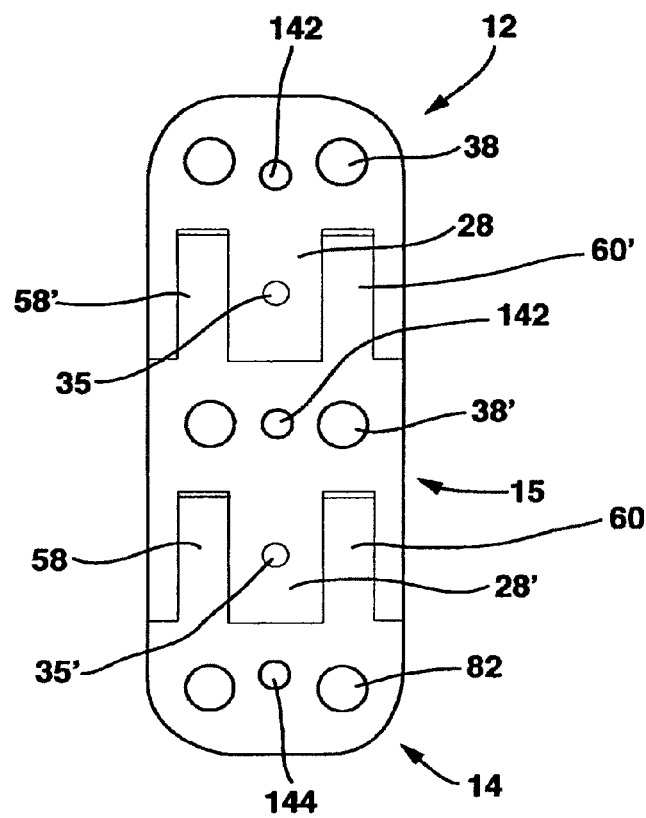
FIG. 3 is a bottom view of the static compression device of FIG. 1.
Figure 4:
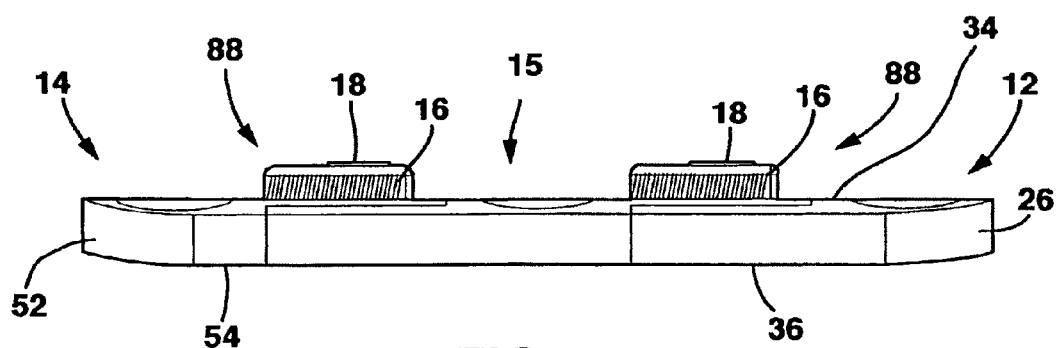
FIG. 4 is a side view of the static compression device of FIG. 1.
Figure 5:
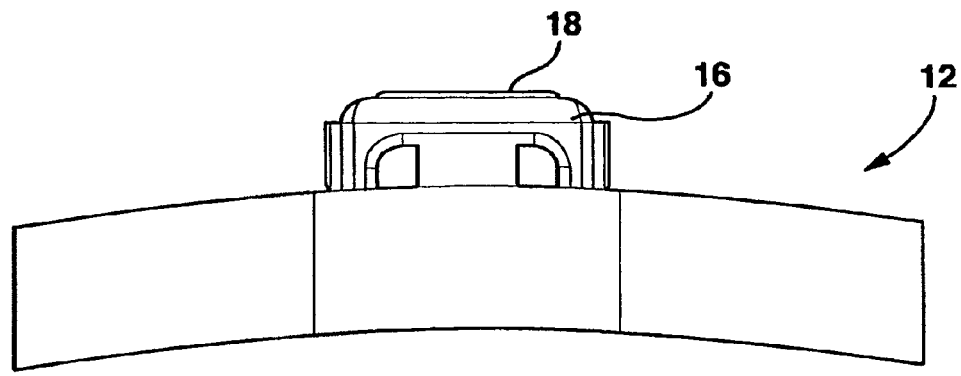
FIG. 5 is a bottom end view of the static compression device of FIG. 1.
Figure 6:
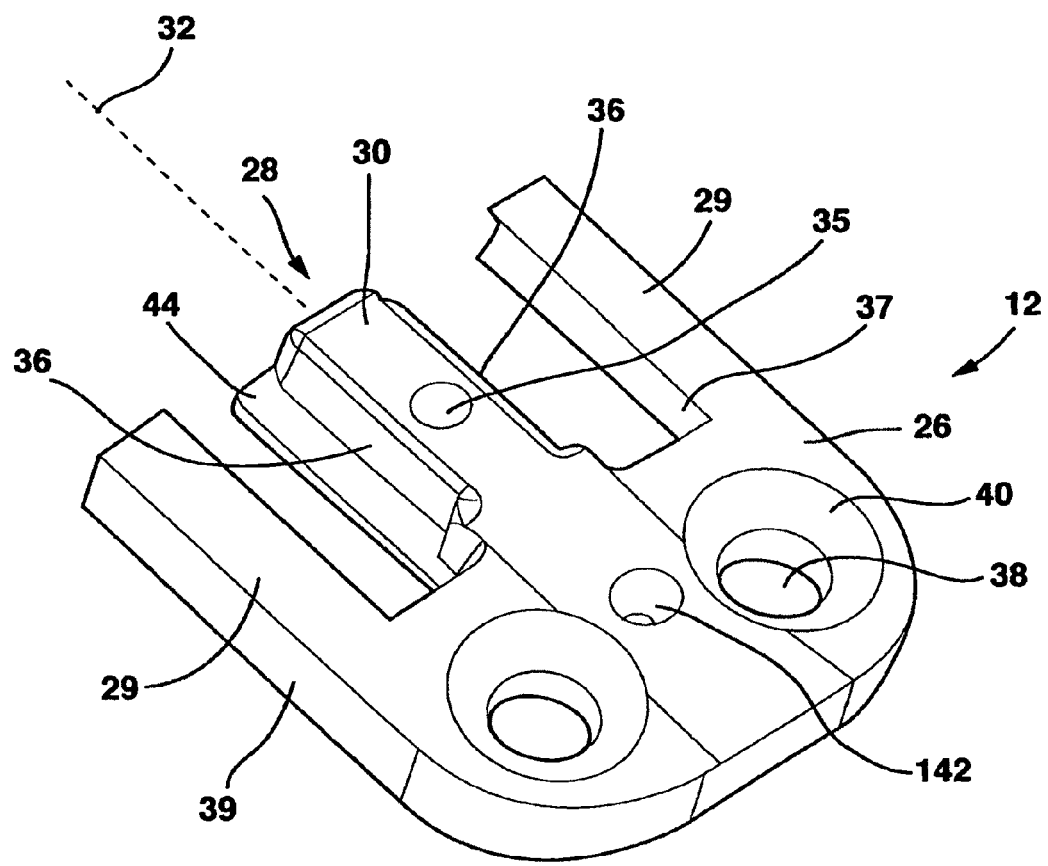
FIG. 6 is a perspective view of the male plate of the static compression device of FIG. 1.
Figure 7:
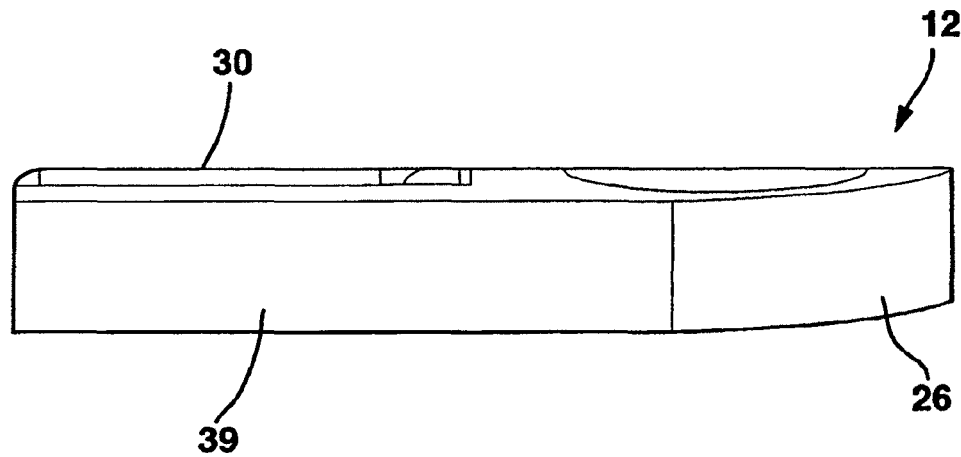
FIG. 7 is a side view of the male plate of the static compression device of FIG. 1.
Figure 8:
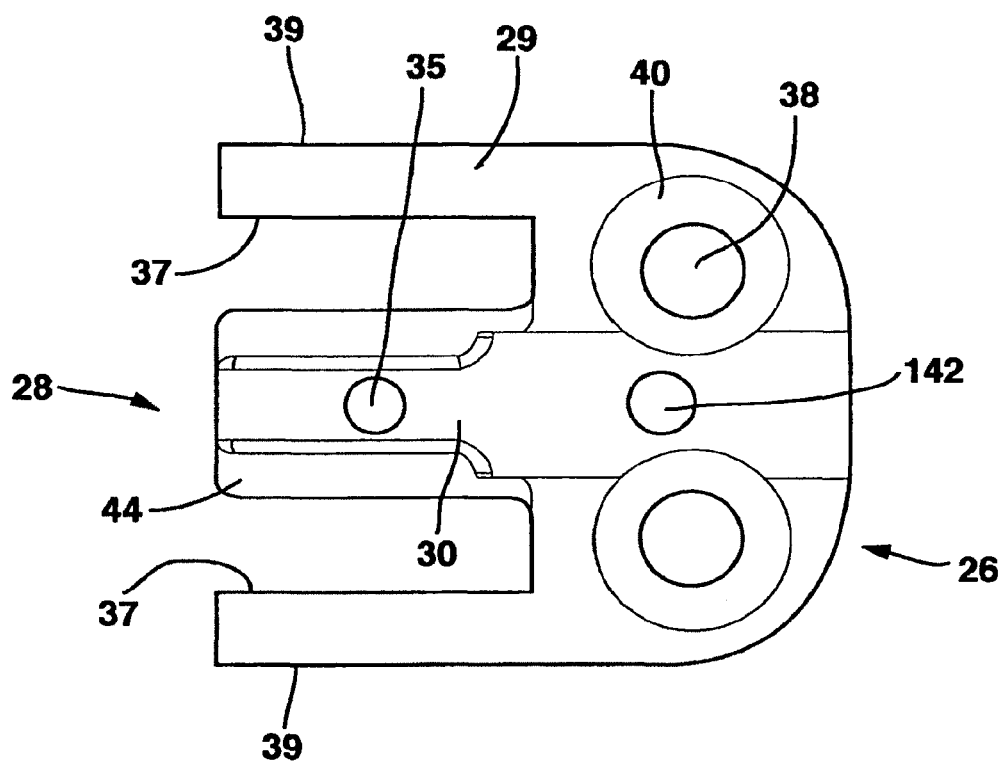
FIG. 8 is a top view of the male plate of the static compression device of FIG. 1.
Figure 9:
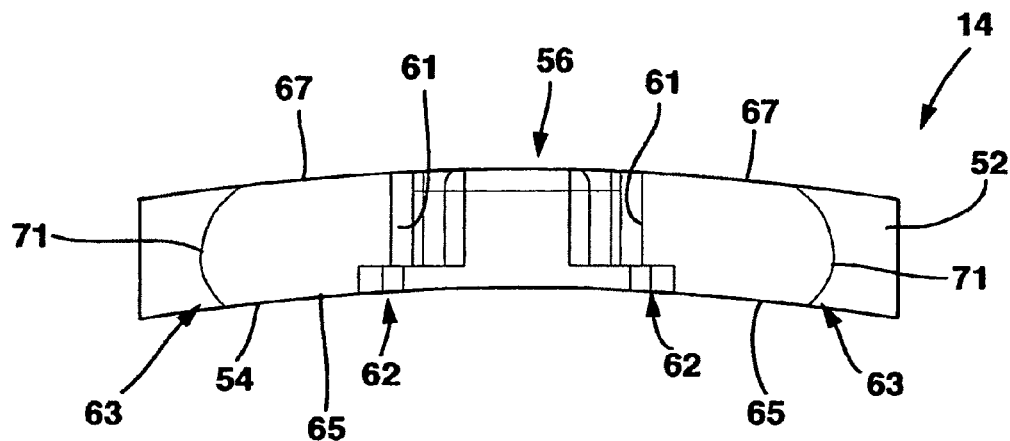
FIG. 9 is a bottom end view of the male plate of the static compression device of FIG. 1.
Figure 10:
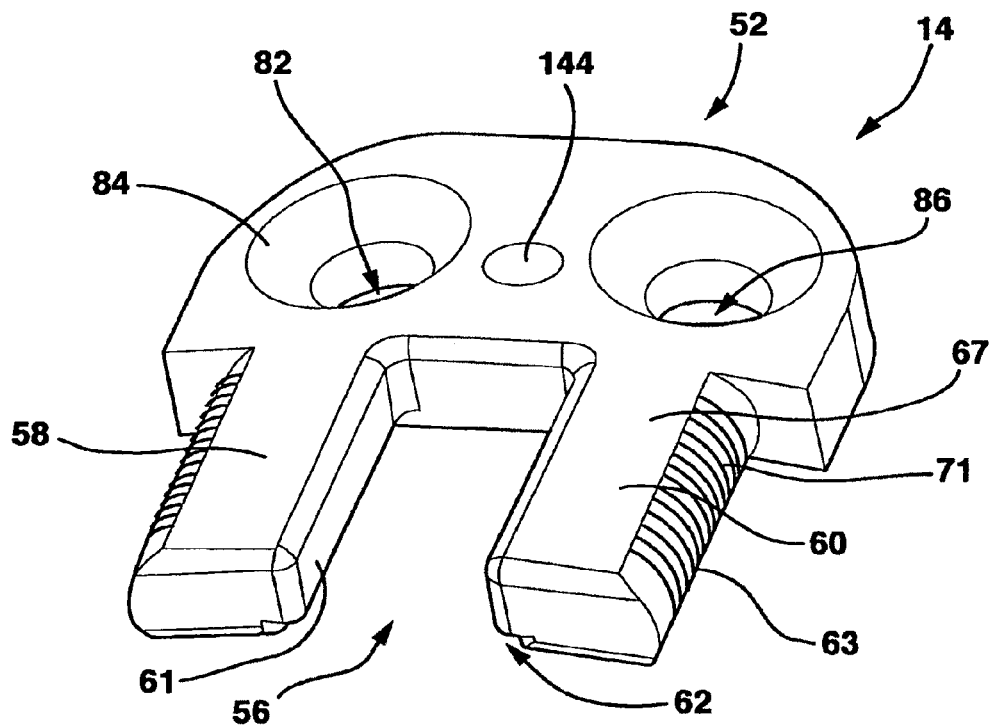
FIG. 10 is a perspective view of the female plate of the static compression device of FIG. 1.
Figure 11:
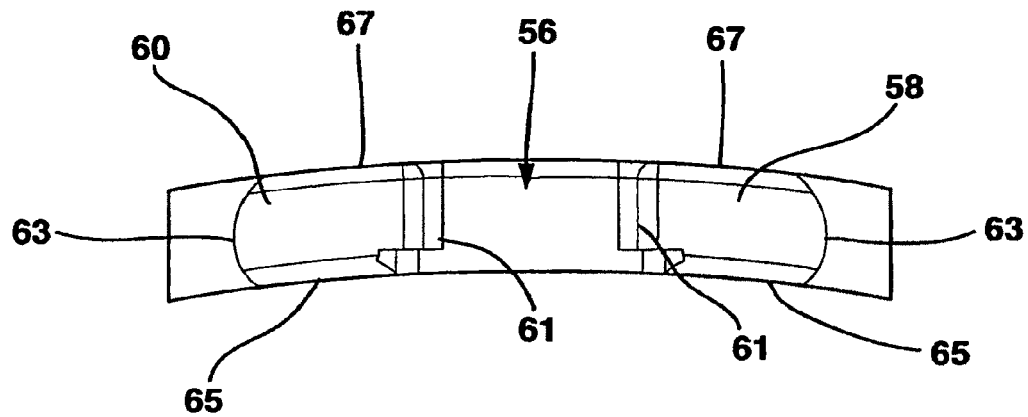
FIG. 11 is an end view of the female plate of the static compression device of FIG. 1.
Figure 12:
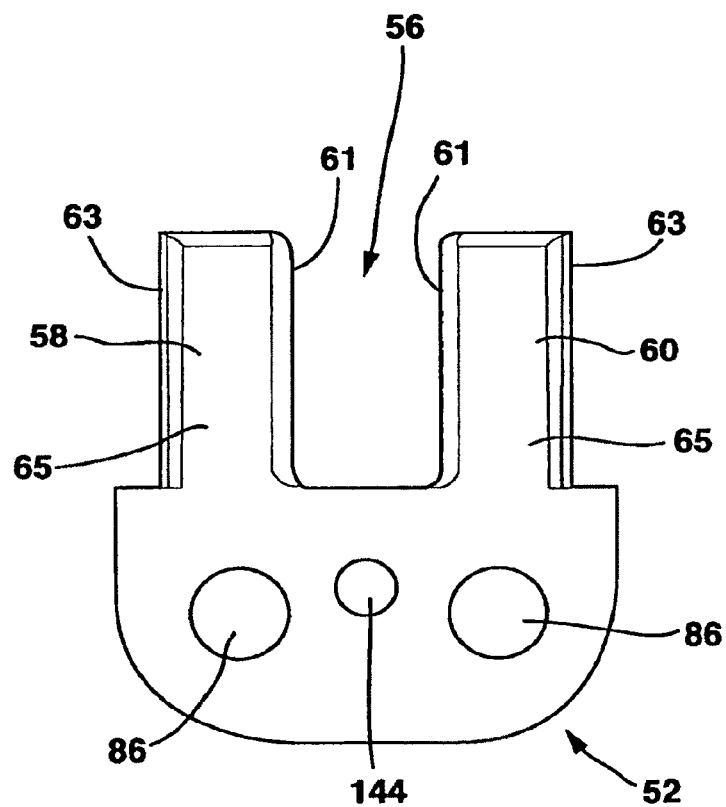
FIG. 12 is a bottom view of the female plate of the static compression device of FIG. 1.
Figure 13:
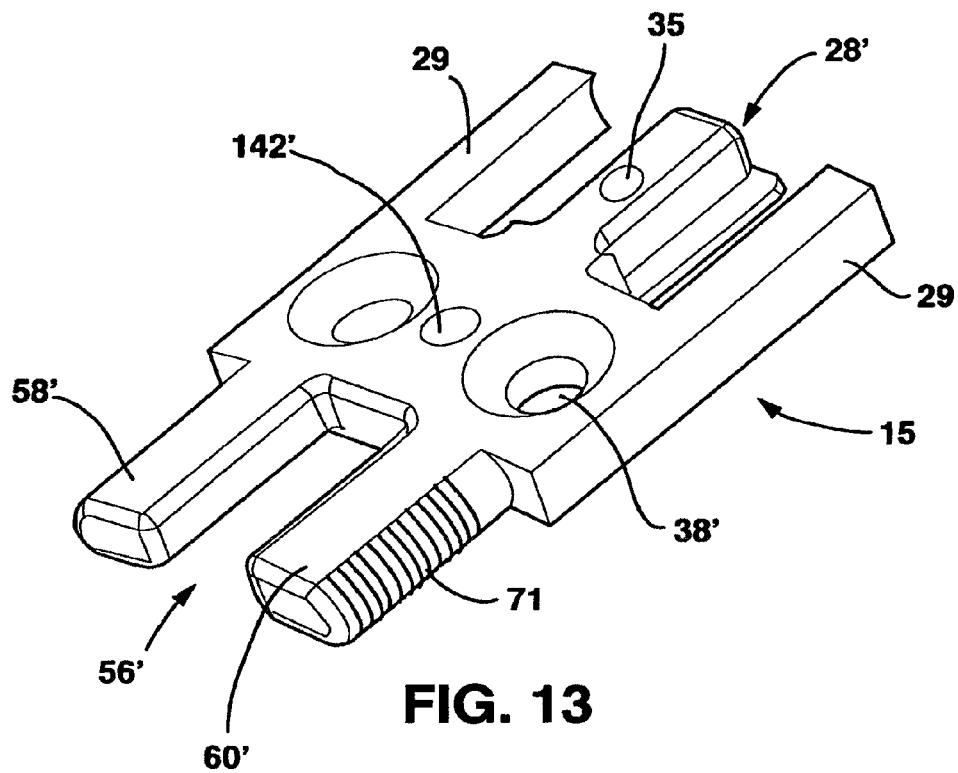
FIG. 13 is a perspective view of the interconnecting plate of the static compression device of FIG. 1.
Figure 14:
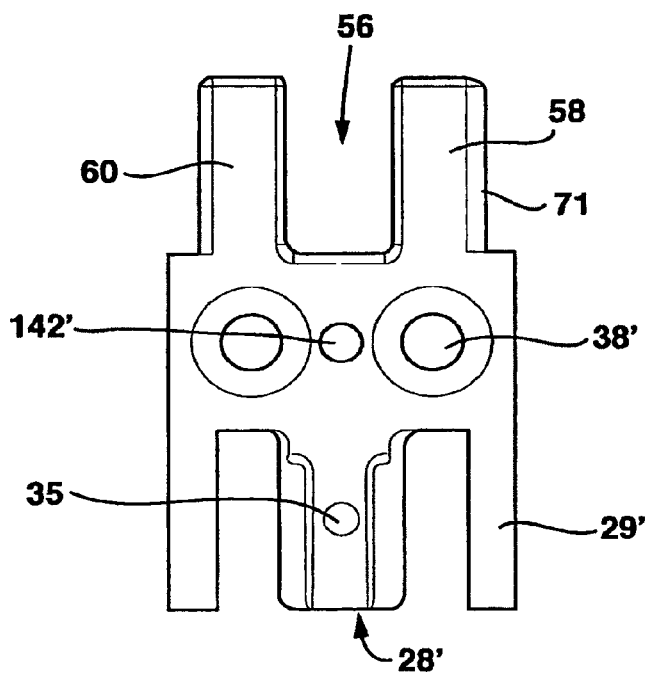
FIG. 14 is a top view of the interconnecting plate of the static compression device of FIG. 1.

The SC device 10 in a preferred embodiment shown in FIGS. 1-14 and 18 has five main parts, a male plate 12, a female plate 14, an interconnecting plate 15, a locking clamp 16 and a locking screw 18 that, in combination with standard cancellous bone screws (not shown) fix the SC device 10 to the patient's vertebrae. The SC device 10 has a top side 20, a bottom side 22 and opposed medial sides 24.

The male plate 12 has a male main body 26 and a central protrusion 28 extending away from the male main body 26. The central protrusion 28 has a top surface 30, a longitudinal axis 32, a bottom surface 33 and parallel sides 36. Central protrusion 28 also has a threaded whole 35 in the top surface 30.

The male plate 12 also has a pair of side protrusions 29 extending away from the male main body 26 on opposite sides of the central protrusion 28. Each of the side protrusions 29 has an inner surface 37 and an outer surface 39. The inner surfaces 37 are directed toward the central protrusion 28 and are preferably curved in a concave fashion to mate with the outer surfaces 63 of the left guide 58 and right guide 60 of the interconnecting plate 15 or the female plate 14 as will be described hereafter.

The male main body 26 is relatively flat with a top side 34 and a bottom side 36 and, in a preferred embodiment, has two screw receiving holes 38. The screw receiving holes 38 each have a bowl-shaped basin 40 on the top side 34 to receive the heads of the screws 43 and a through whole 42 through which the main body of the screws 43 pass to come into contact with the vertebral body. The throughholes 42 are configured in a manner that allows the cancellous bone screws 43 to be rigidly fixed to the plate once inserted in bone. The method of fixing the screws 43 to the plate may utilize any number of mechanisms well understood in the art that allow the screws 43 and the male plate 12 to maintain a rigid relationship once the screws 43 are inserted in bone.

The bottom side 36 of the male plate 12, female plate 14 and interconnecting plate 15 is preferable roughened, thereby allowing the bottom side 22 of the SC device 10 to "grip" the vertebral body when the bottom side 22 of the SC device 10 is brought into contact with and secured to the vertebral body by the interaction of the screws 43 and the body of the SC device 10 as described herein.

As mentioned, the male plate 12 has a central protrusion 28 with a top surface 30 and a longitudinal axis 32. Central protrusion 28 is dimensioned to mate with and secure the male plate 12 with the interconnecting plate 15 or the female plate 14 as will be described in detail hereafter. Where the interconnecting plate 15 is used, the combined length of the central protrusion 28 on the male plate 12 and the central protrusion 28' on the interconnecting plate 15 will be slightly longer than the distance the SC device 10 is intended to provide compression over.

Central protrusion 28 has a boss 44 extending entirely through it approximately parallel to the top surface 30 that is designed to mate with a relief cut 62 in the interconnecting plate 15/female plate 14.

The interconnecting plate 15 combines the features of the male plate 12 and the female plate 14 on its opposite ends. As a result, on one end of interconnecting plate there is a central protrusion 28' essentially as described in connection with the central protrusion 28 of male plate 12. On the opposite end of interconnection plate 15, there is a protrusion receiving channel 56 essentially as described hereafter in connection with the protrusion receiving channel 56 of female plate 14. In addition, interconnecting plate 15 has at least a pair of screw receiving holes 38 essentially as described in connection with the screw receiving holes 38 of the male plate 12.

The purpose of the interconnecting plate 15 is to allow the SC device 10 to be secured to three or more adjacent vertebrae and allow the SC device 10 to apply compression across these vertebrae to facilitate healing as described herein. As a result, a single interconnecting plate 15 may be placed between the male plate 12 and the female plate 14 and attached to the vertebra between the vertebrae that the male and females plates 12, 14 are attached to. Alternately, several interconnecting plates 15 can be connected end to end (i.e., the protrusion receiving channel 56 of one interconnecting plate 15 receives the central protrusion 28' of an adjacent interconnecting plate 15 and the process continues until all the interconnecting plates 15 are joined together) to form an interconnecting span with a male plate 12 and a female plate 14 attached to the ultimate ends of this chain of interconnecting plates 15. In this embodiment of the invention, each of the interconnecting plates 15 would have screw receiving holes 38 allowing each interconnecting plate 15 to be attached to a single vertebra by bone screws 43. In a variant of this embodiment, a single interconnecting plate 15 could have several sets of screw receiving holes 38 so that this single interconnecting plate 15 could be attached to several adjacent vertebrae or could span a previously fused segment.

The female plate 14 has a female main body 52 with a bottom side 54 and a protrusion receiving channel 56. Protrusion receiving channel 56 is formed between a left guide 58 and a right guide 60 that extend away from the female main body 52. Left guide 58 and right guide 60 each have an inner surface 61, an outer surface 63, a bottom surface 65 and a top surface 67. Left guide 58 and right guide 60 are basically rectangular in cross-section with inner surfaces 61 being preferably essentially planar and with outer surfaces 63 being essentially outwardly curved with a series of ridges 71 extending outwardly. On the bottom surface 65 of the left and right guides 58, 60 facing the protrusion receiving channel 56, there is a relief cut 62 machined to accept the boss 44 on the central protrusion 28' of the interconnecting plate 15 or the male plate 14.

Protrusion receiving channel 56 is dimensioned to snugly receive the central protrusion 28' with the locking clamp 16 in place on the central protrusion 28' as will be described hereafter so that the central protrusion 28' is "captured" and held in the protrusion receiving channel 56 by physical contact between the outer surface of the locking clamp 16 and the inner surfaces of the left guide 58 and right guide 60 as well as by the interaction between the central protrusion 28' and the boss 44 on the inferior aspect of the central protrusion 28' and relief cut 62.

The outer surfaces 63 of the left and right guides 58, 60 contact the inner surfaces 37 of the side protrusions 29 under the influence of the locking clamp 16, as will be described hereafter, to securely locate the female plate 14 with respect to the interconnecting plate 15 and the interconnecting plate 15 with the male plate 12.

The female plate 14, also in a preferred embodiment, has two screw receiving holes 82. These screw receiving holes 82 receive standard cancellous bone screws 43 that are threaded into the bone of the vertebrae. In similar fashion to screw receiving holes 38, the screw receiving holes 82 also have a bowl-shaped basin 84 on the upper surface 78 to receive the heads of the bone screws 43 and a throughole 86 through which the main body of the bone screws 43 pass to come into contact with the vertebral body. The throughholes 86 are configured in a manner that allows the cancellous bone screws 43 to be rigidly fixed to the plate once inserted in bone by the interaction of the screws 43 with the basins 84. The method of fixing the screws 43 to the female plate 14 may utilize any number of mechanisms well understood in the art that allow the screws 43 and the female plate 14 to maintain a rigid relationship once the screws 43 are inserted in bone.

The SC device 10 has a locking mechanism 88. Locking mechanism 88 converts "active" compression applied by the surgeon using the compression device 90 described below interacting with the SC device 10 at the time of surgery to "static" compression after surgery. The locking mechanism 88 also provides rigid fixation to the SC device 10 to optimize bone healing and preventing further settling from occurring.

The locking mechanism 88 in one embodiment includes locking clamp 16 and locking screw 18. The locking clamp 16 has a top surface 92 with a hole 93 extending through it, a bottom surface 94, parallel sides 96, a longitudinal axis 97 and an inner channel 99 between the parallel sides 96 and below the top surface 92. The inner width of the inner channel 99 of the locking clamp 16 (i.e., the inside distance between the parallel sides 96) is such that the locking clamp 16 will fit snugly over the central protrusion 28. The width of the locking clamp 16 (i.e., the distance between the parallel sides 96) is such that the locking clamp 16 will fit snugly between the left and right guides 58, 60 in the protrusion receiving channel 56.

A single large locking screw 18, dimensioned to rotate freely within the hole 93 of the locking clamp 16, activates the locking mechanism 88. In the embodiment of the invention shown in FIGS. 1-19, the locking screw 18 has a head 106, a body 108 and a distal end 110 opposite the head 106. The head 106 has a larger cross-sectional diameter than the threaded body 108. The body 108 is threaded at least on the distal end 110 to correspond to the threads of the threaded hole 35 in the protrusion 28.

The parallel sides 96 of locking clamp 16 preferably have a series of ridges 46 and valleys 48, preferably placed substantially perpendicular to the longitudinal axis 97 and tapered from top to bottom, to locate and affix the locking clamp 16 to the inner surfaces of the left guide 58 and right guide 60 of the interconnecting plate 15 and female plate 14.

Through this configuration, the ridges 46 and valleys 48 on the sides 96 of the locking clamp 16 preferably contact and engage with the inner surfaces of left and right guides 58, 60 in frictional or mechanical contact to precisely locate and affix the locking clamp 16 within the protrusion receiving channel 56. Because the series of ridges 46 and 48 are tapered, as the series of ridges 46, 48 are moved into contact with and engage the inner surfaces of left and right guides 58, 60, this engagement adds compressive force to the adjacent vertebral bodies through the SC device 10. The locking clamp 16 is preferably made of a material that is harder than the material of the interconnecting plate 15 or the female plate 14.

The present invention also includes a compression device 90 (FIGS. 20-23) that allows the surgeon to provide active, controlled compression between the two sliding components of the SC device 10 (male plate 12 and female plate 14) at the time of surgery. This compression device 90 allows the surgeon to accurately measure the force applied across the graft by the SC device 10 and allows the surgeon to stop compressing when a predetermined amount of force has been obtained. Since both the male plate 12 and the female plate 14 are each connected to adjacent vertebral bodies by two fixed angle bone screws 43, this provides for even, surgeon-controlled compression across the interbody graft.

The compression device 90 has two arms 114, 116 that each have a handle 118, 120 at one end and a foot 122, 124, located at a distal end 126, 128, respectively. The arms 114, 116 are connected via a pivot 130 that connects the respective arms 114, 116 and allows them to move in scissors-like movement with respect to each other. By connecting the arms 114, 116 through a pivot 130, a surgeon squeezing the handles 118, 120 moves the distal ends 126, 128 together. By connecting these distal ends 126, 128 to the SC device 10, a surgeon squeezing the handles 118, 120 together is able to apply compression to the SC device 10 and thus to adjacent vertebral bodies through the interaction of the feet 122, 124 and the male plate 12 and female plate 14 as will be explained hereafter.

Each foot 122, 124 of the compression device 90 engages the male plate 12 or female plate 14 (or interconnecting plate 15), respectively, to apply pressure to move the male plate 12 and female plate 14 toward each other as the physician squeezes the handles 118, 120 together. In the embodiment of compression device 90 and SC device 10 shown in FIG. 23, the distal ends 126, 128 of feet 122, 124, respectively, are shaped with pins 132 that protrude from the distal ends 126, 128.

Figure 21:
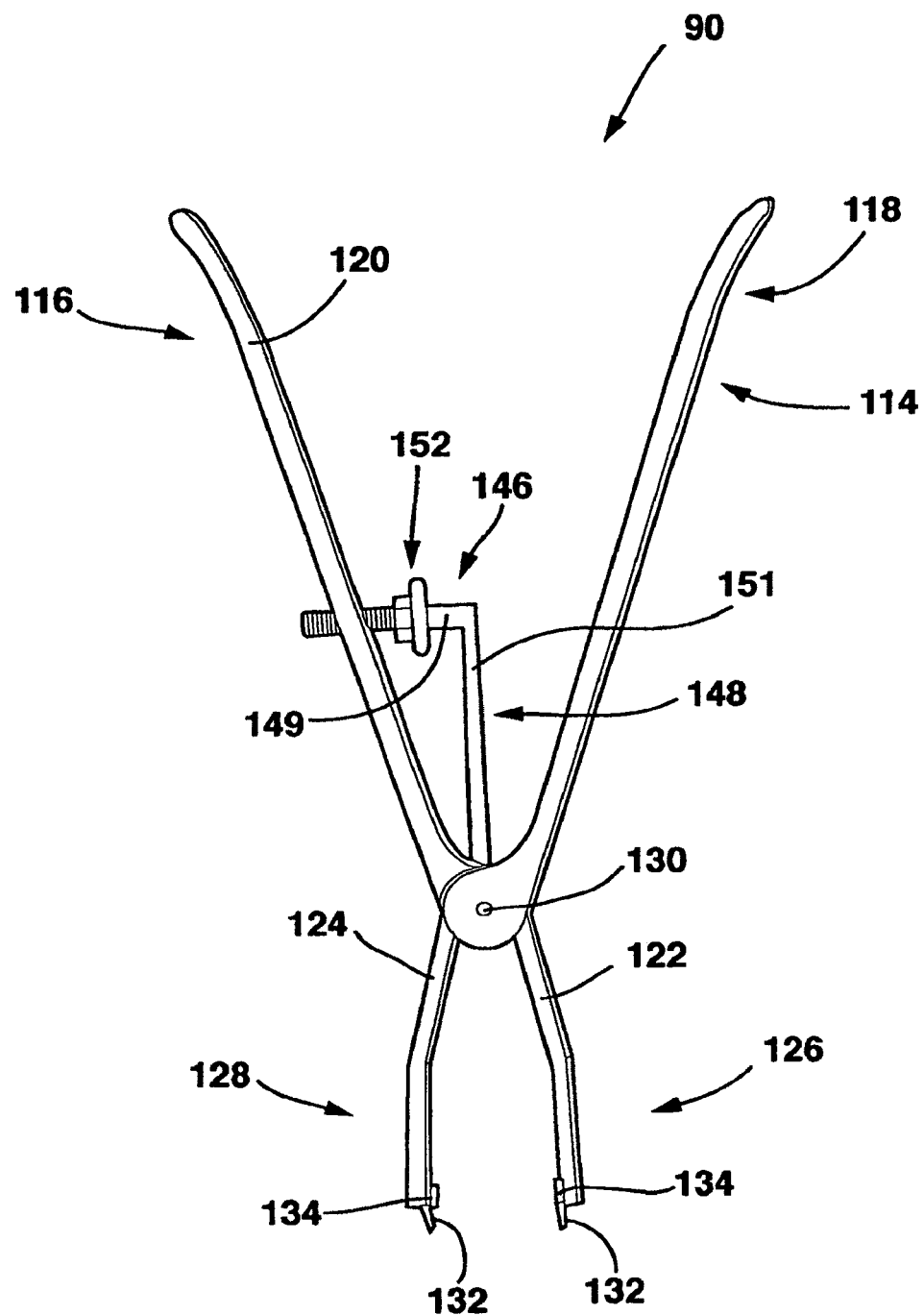
FIG. 21 is a perspective view of the embodiment of the compression tool of FIG. 20 from the opposite side of the view of FIG. 20.
Figure 22:
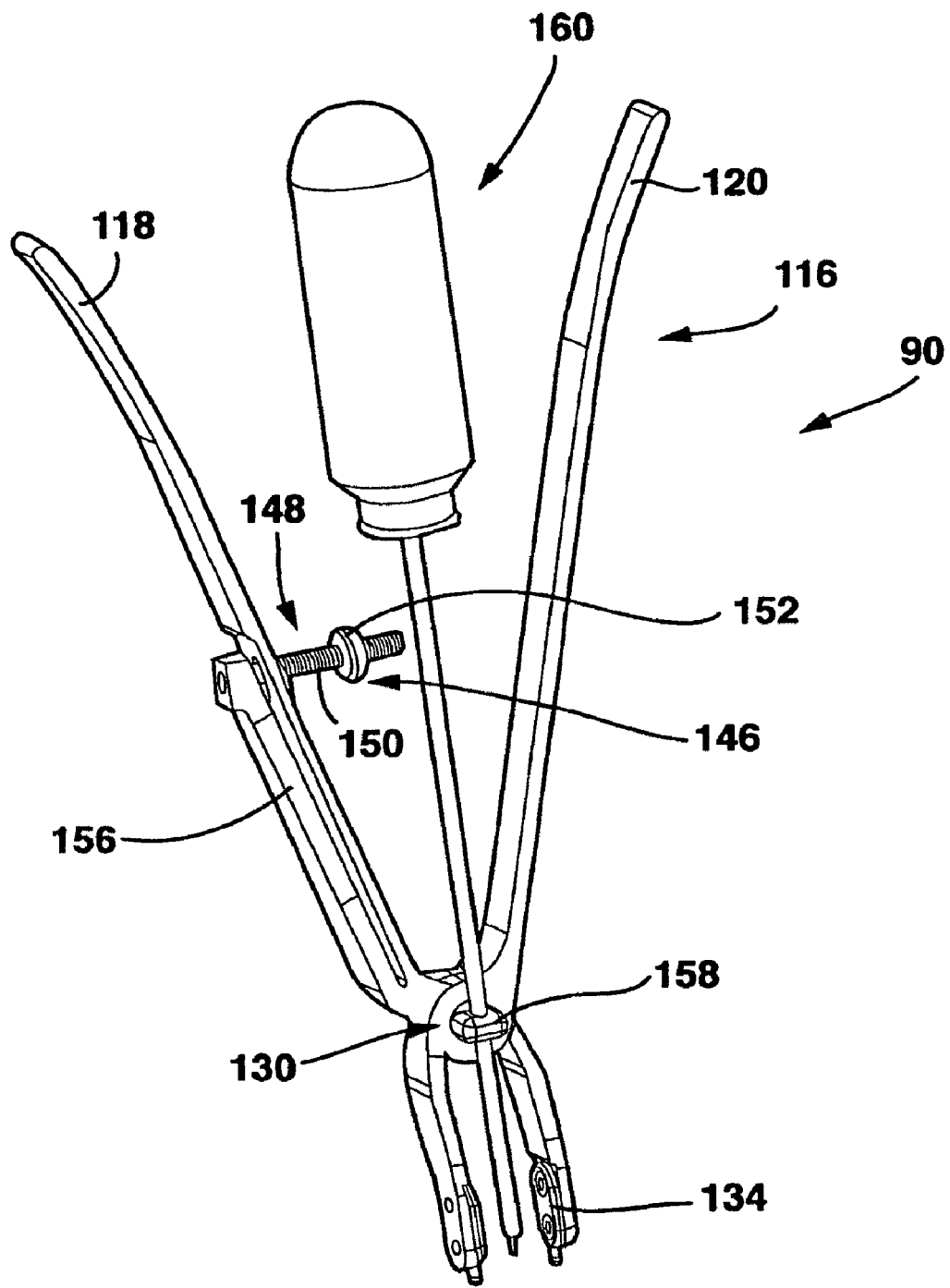
FIG. 22 is a perspective view of the preferred embodiment of the compression tool of the present invention with cannula for receiving a screwdriver.
Figure 23:
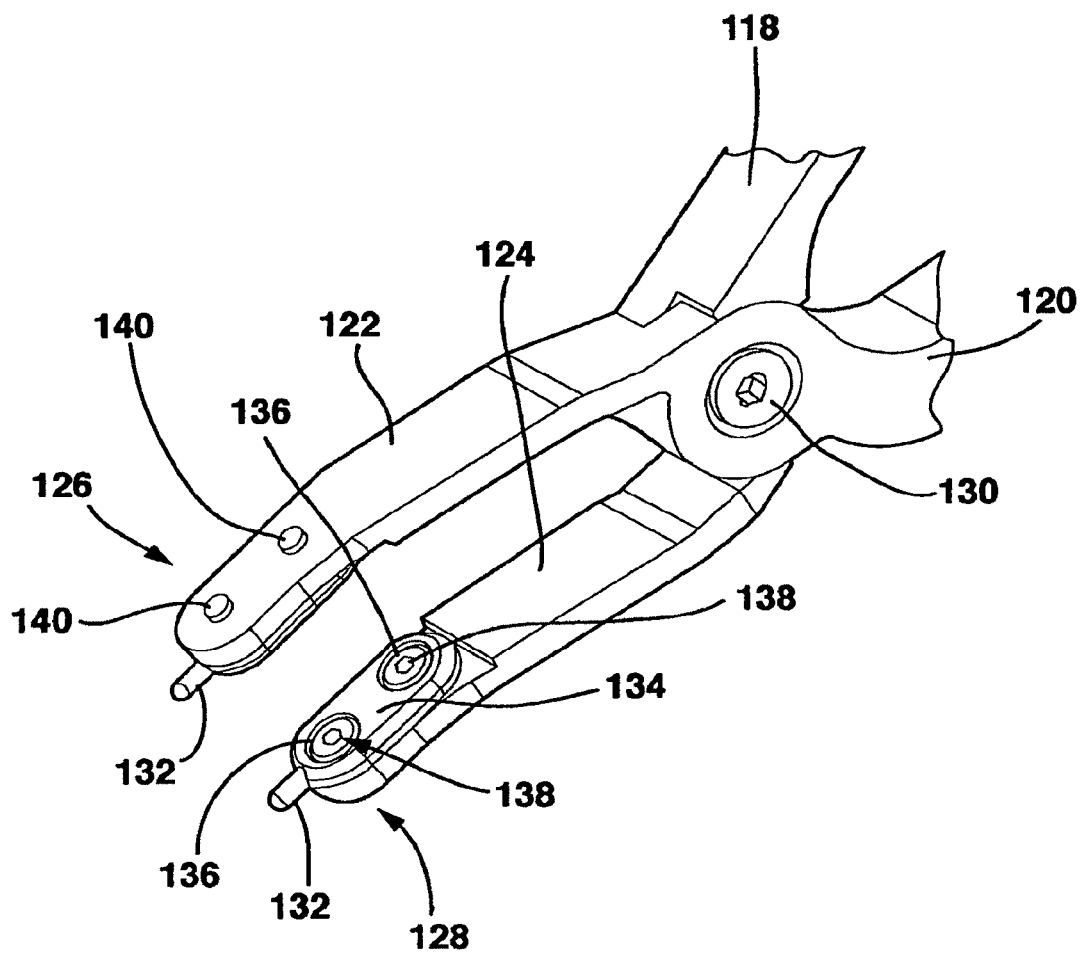
FIG. 23 is a close up perspective view of the distal end of the compression tools of the present invention.
Figure 24:
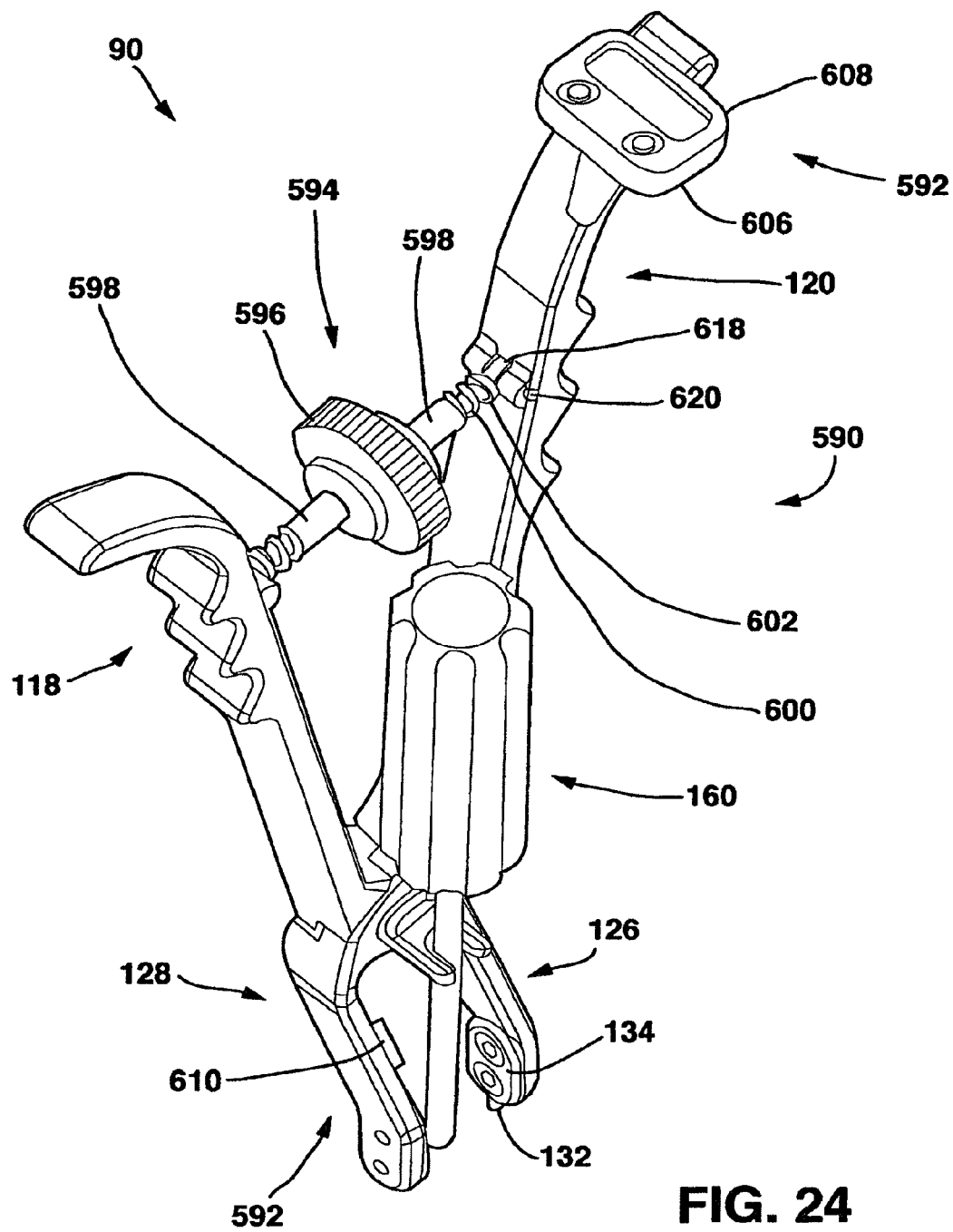
FIG. 24 is a perspective view of another embodiment of the compression tool of the present invention.
Figure 25:
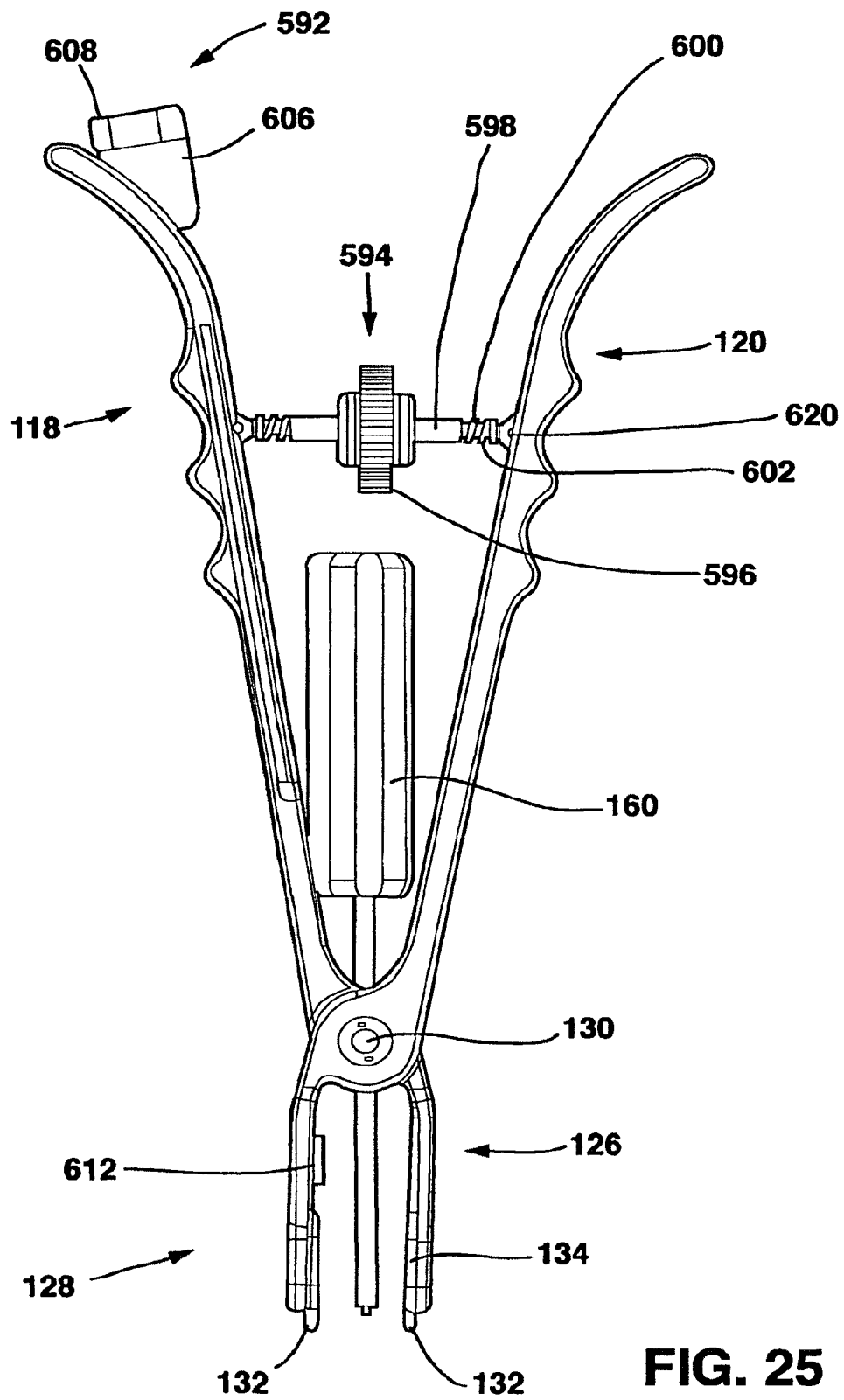
FIG. 25 is a side view of the embodiment of the compression tool of FIG. 24.

In the embodiment shown in FIGS. 21-23, pins 132 protrude from adaptor plates 134 having throughholes 136. Adaptor plates 134 are secured to the distal ends 126, 128 of feet 122, 124, respectively by screws 138 that pass through throughholes 136. The distal ends 126, 128 of feet 122, 124, respectively each have a threaded secure hole 140 that receives a screw 138. In this way, adaptor plates 134 are secured to the distal ends 126, 128 of feet 122, 124, respectively. The adaptor plates 134 may be removed and replaced with hooks protruding from the distal ends 126, 128 of feet 122, 124, respectively, that each engage a slot on the outermost aspects of the male and female plates 12, 14 placed or formed in the top side 34 of the male plate 12 and the top surface 78 of the female plate 14. This enables the ends of compression device 90 to be modular (i.e., replaceable so that the appropriate end for a desired application can be placed on the compression device 90) with respect to using different techniques to achieve compression.

The male plate 12 and female plate 14 each have a notch 142, 144, respectively, located on opposite ends of the SC device 10 and shaped to receive the pins 132 in a snug, conforming fashion so that compression applied to the feet 122, 124 by squeezing the handles 118, 120 together is transferred from the distal ends 126, 128 to the male plate 12 and female plate 14, respectively, through the interaction of the pins 132 with the notches 142, 144.

In an alternate embodiment of the invention, the distal ends 126, 128 of feet 122, 124, respectively, again engage the male plate 12 and the female plate 14, respectively, through pins 132. However, in this embodiment, the notches 142, 144 are located in the outer edge of the top surfaces 26 and upper surface 78 of the male plate 12 and female plate 14, respectively, sized and shaped to receive the pins 132 in a snug fashion so that compression applied to the feet 122, 124 by squeezing the handles 118, 120 together is transferred from the pins 132 to the male plate 12 and female plate 14, respectively, through the notches 142, 144.

The compression device 90 also preferably has a gauge 146 that allows the physician to measure the compression force being applied to the SC device 10, and thus to the vertebral bodies, by the squeezing together of the handles 118, 120. The gauge 146, by quantifying the deflection the handles 118, 120 when they are squeezed together, gives an accurate measurement of force applied across the SC device 10. In the embodiment of the compression device 90 shown in FIG. 20, gauge 146 includes an arm 148 attached to pivot 130 and located between handles 118, 120. The arm 148 preferably has a circular, oval, square or rectangular cross-section and a horizontal and a vertical component 149, 151, respectively. The aim 148 has indicia ISO located on at least a portion of the horizontal component 149.

The gauge 146 has an indicator 152 that is an annular spacer located along the horizontal component 149 of arm 148. The indicator 152 has a central opening 154 sized to be approximately the same size and shape as the cross-sectional size and shape of the horizontal component 149 of arm 148 so that indicator 152 is attached to the horizontal component 149 by sliding the horizontal component 149 through the first central opening 154. A frictional fit between the first central opening 154 and the horizontal component 149 holds the indicator 152 in position on the horizontal component 149.

As mentioned above, when the handles 118, 120 are squeezed together, the resulting amount of deflection of the handles 118, 120 is directly related to the force applied by the physician as he or she squeezes the handles 118, 120 together. Because the vertical component 151 of the arm 148 is rigidly attached to the pivot 130, as the handles 118, 120 move together as a result of being squeezed, the horizontal component of the arm 148 and its associate indicator 152 does not move. As a result, the handle 120 will be deflected along the horizontal component 149 of the arm 148 and along the indicia 150 located on the horizontal component 149. By observing the location of the handle 120 with respect to the indicia 150 on the horizontal component 149, the amount of force applied to handles 118, 120 and, therefore to the distal ends 126, 128 of feet 122, 124, is indicated. When the distal ends 126, 128 are placed in functional contact with the notches 142, 144 of the male plate 12 and female plate 14, the gauge 146 indirectly measures the compression being applied to the graft, and allows the surgeon to stop compressing once a predetermined force has been achieved.

By placing the indicator 152 at a desired location on the horizontal component 149 of arm 148, the physician can squeeze the handles 118, 120 together until the handle 120 moves into contact with the indicator 152. At this point, the physician knows that the desired amount offered has been applied to the compression device 90 and thereby to the SC device 10 to the graft.

In another embodiment of the compression device 90 shown in FIG. 22, gauge 146 again includes an arm 148. But, in this embodiment, the arm 148 is connected to a rigid arm 156 located on the outside of handle 118. Rigid arm 156 is attached to handle 118 near the pivot 130. Arm 148 extends from the rigid arm 156 in the direction that handle 118 moves when it is squeezed together with handle 120 and may extend through a slot in handle 118 or may be formed around handle 118 so that arm 148 extends toward handle 120. In this embodiment as well, indicator 152 is located between handles 118, 120.

As mentioned above, when the handles 118, 120 are squeezed together, the resulting amount of deflection of the handles 118, 120 is directly related to the force applied by the physician as he or she squeezes the handles 118, 120 together. Because the arm 148 is rigidly attached to the rigid arm 156, as the handle 118, 120 move together as a result of being squeezed, the arm 148 and its associate indicator 152 does not move. As a result, the handle 118 will be deflected along arm 148 and along the indicia 150 located on arm 148. By observing the location of the handle 118 with respect to the indicia 150 on arm 148, the amount of force applied to handles 118, 120 and, therefore to the distal ends 126, 128 of feet 122, 124, is indicated. When the distal ends 126, 128 are placed in functional contact with the notches 142, 144 of the male plate 12 and female plate 14, the gauge 146 indirectly measures the compression being applied to the graft, and allows the surgeon to stop compressing once a predetermined force has been achieved. Again, by observing the location of the handle 118 versus the indictor, the surgeon will know that the desired amount of force has been applied to the compression device 90 and thereby to the SC device 10 to the graft.

An alternative embodiment of the compression device 90 is referred to as the static compensating compressor 590 and shown in FIGS. 24-27. The static compensating compressor 590 utilizes a force indicator 592 and a method to measure static compressive forces applied by the patient's own anatomy to allow the surgeon to factor the patient's own static compressive forces out to ensure the correct value of the absolute compression applied through the SC device 10 to the vertebral bodies. The static compensating compressor 590 includes a turnbuckle 594 that uses a threaded nut 596, threaded inserts 598, along with a series of compression springs 600 and guide rods 602, collectively known as the distraction mechanism 604, to allow the surgeon to apply a measurable distraction force (a force in the opposite direction to the compressive force) to unload the vertebral segment. By unload, we mean to take compression pressure, usually applied by the patient's own muscles and ligaments, off the vertebral segments. Once compression pressure on the vertebral segment has been unloaded from the vertebral segment, a null point (i.e., a point where there is no compression or distraction force on the vertebral bodies) is established and therapeutically useful compression can be applied to the vertebral segment at a known rate.

The force indicator 592 has a central processing unit (CPU) 606 and a display 608 to determine and indicate the amount of force applied in either compression or distraction to the SC device 10 and a zeroing function that allows the surgeon to compensate for static anatomical compression. The force indicator 592 also includes a strain gauge 610. The force indicator 592 is a simple electronic device that measures the resistance across the strain gauge 610 that is secured to one of the arms 114, 116 of the compressor 90 and then uses the CPU

606 to determine, by formula or through a lookup table, and indicate the amount of force applied by the compressor 90 and then indicate this amount of force on the display 608. The CPU 606 may be an application specific integrated circuit (ASIC), a digitally based central processing unit or discrete components.

The display 608 is preferably attached to one of the handles 118, 120 of the aims 114, 116 and the CPU 606 and the display 608 are preferably combined into a single unit. However, either or both the CPU 606 and the display 608 may be located remotely from the static compensating compressor 590 and the CPU 606 and the display 608 may be located separately from each other.

The strain gauge 610 is preferably located on a distal end 126, 128 of a respective arm 114, 116 of the compression device 90 although the strain gauge may be located anywhere on an arm 114, 116 or on the pivot 130. As the physician applies compression through the compression device 90 to the SC device 10 and thus to the vertebral bodies by squeezing the handles 118, 120 of the compression device 90 together, the distal ends 126, 128 will flex or bend slightly. The strain gauge 610 measures this flexing or bending of the distal ends 126, 128 and communicates the value to the CPU 606 where the force value, once determined, indicates the amount of force applied to the SC device 10, and thus to the vertebral bodies, as is well understood in the art.

Figure 26:
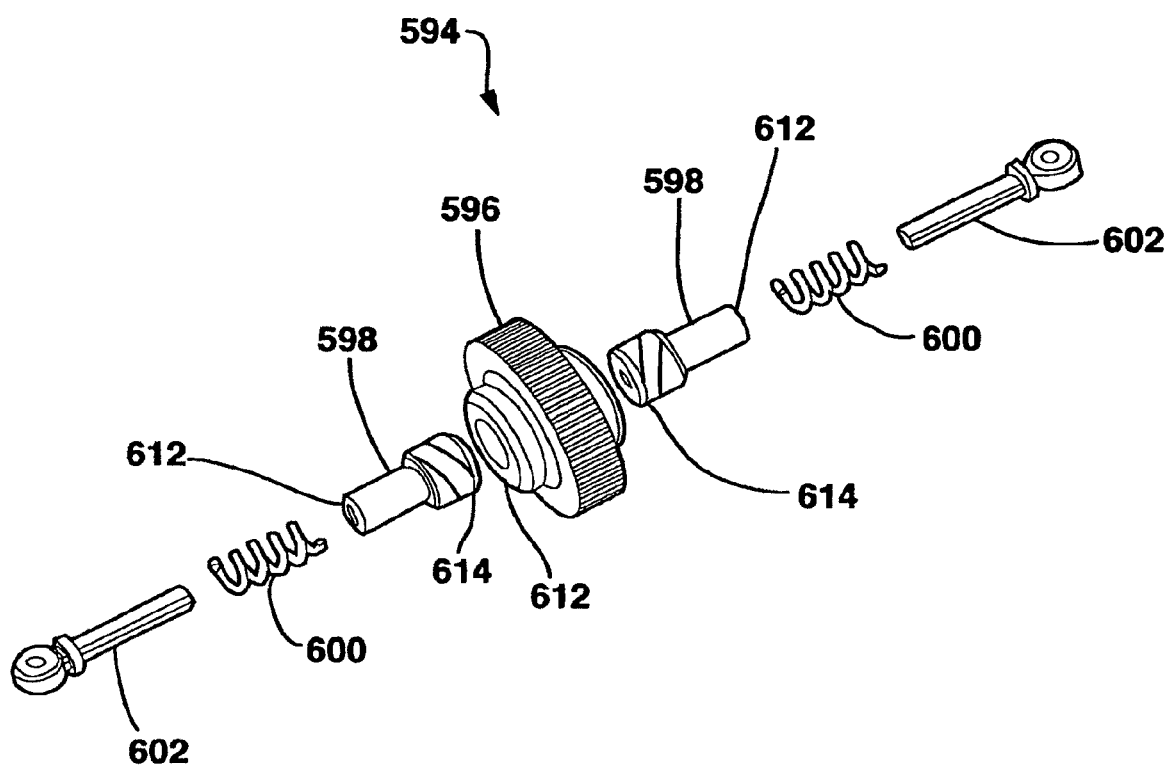
FIG. 26 is an exploded perspective view of the turnbuckle of the embodiment of the compression tool of FIG. 24.
Figure 27:
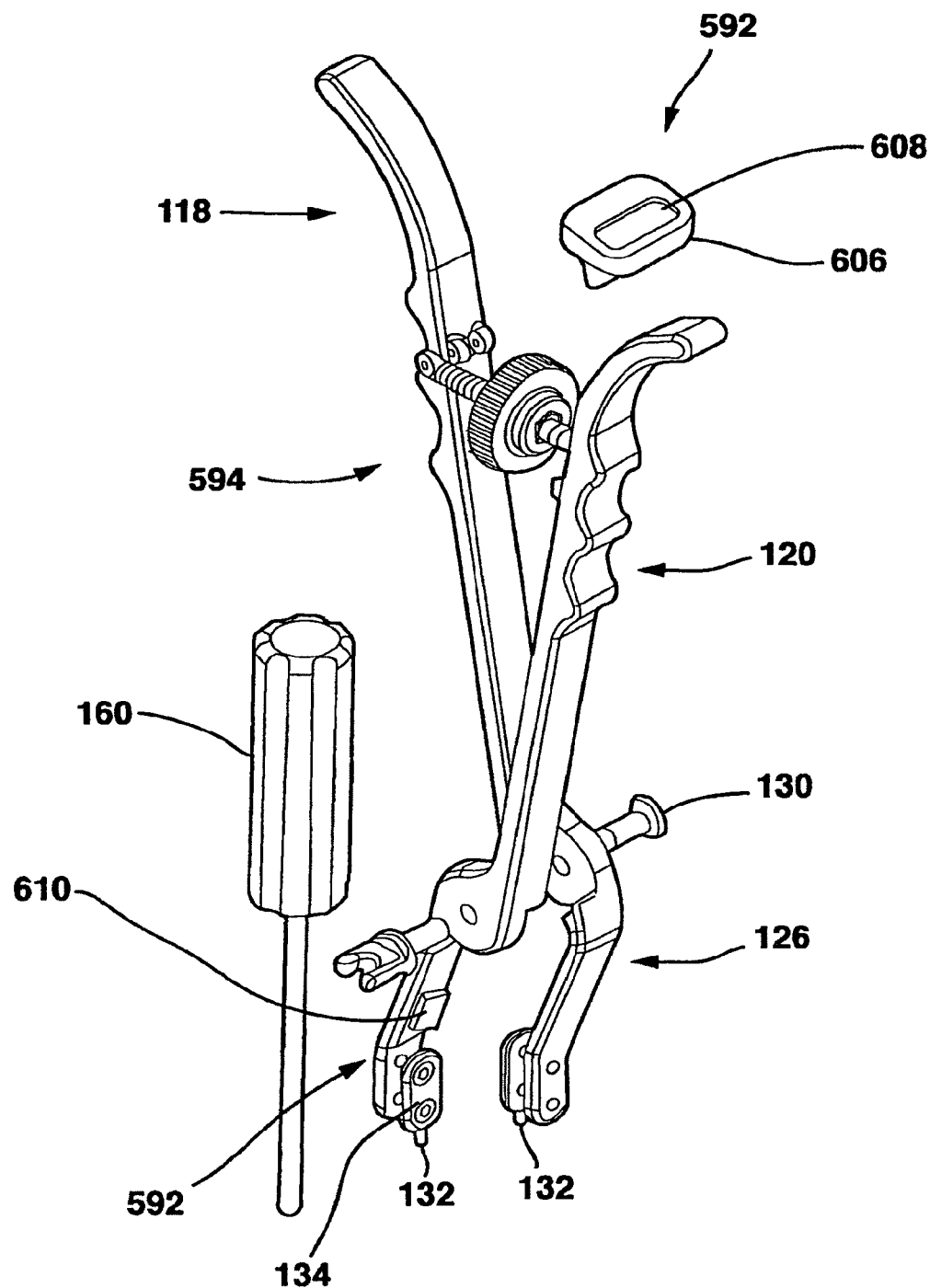
FIG. 27 is an exploded perspective view of the compression tool of FIG. 24.
Figure 28:
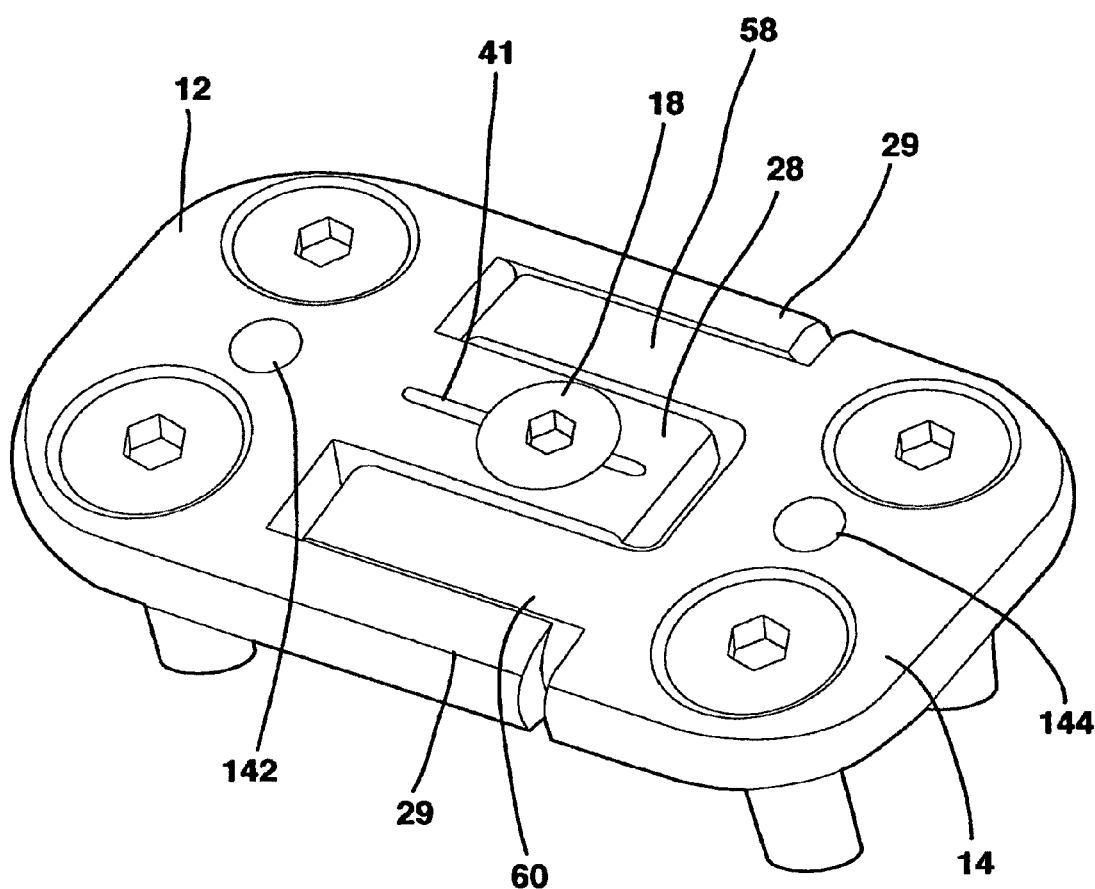
FIG. 28 is a perspective view of an embodiment of the static compression device of the present invention.
Figure 29:
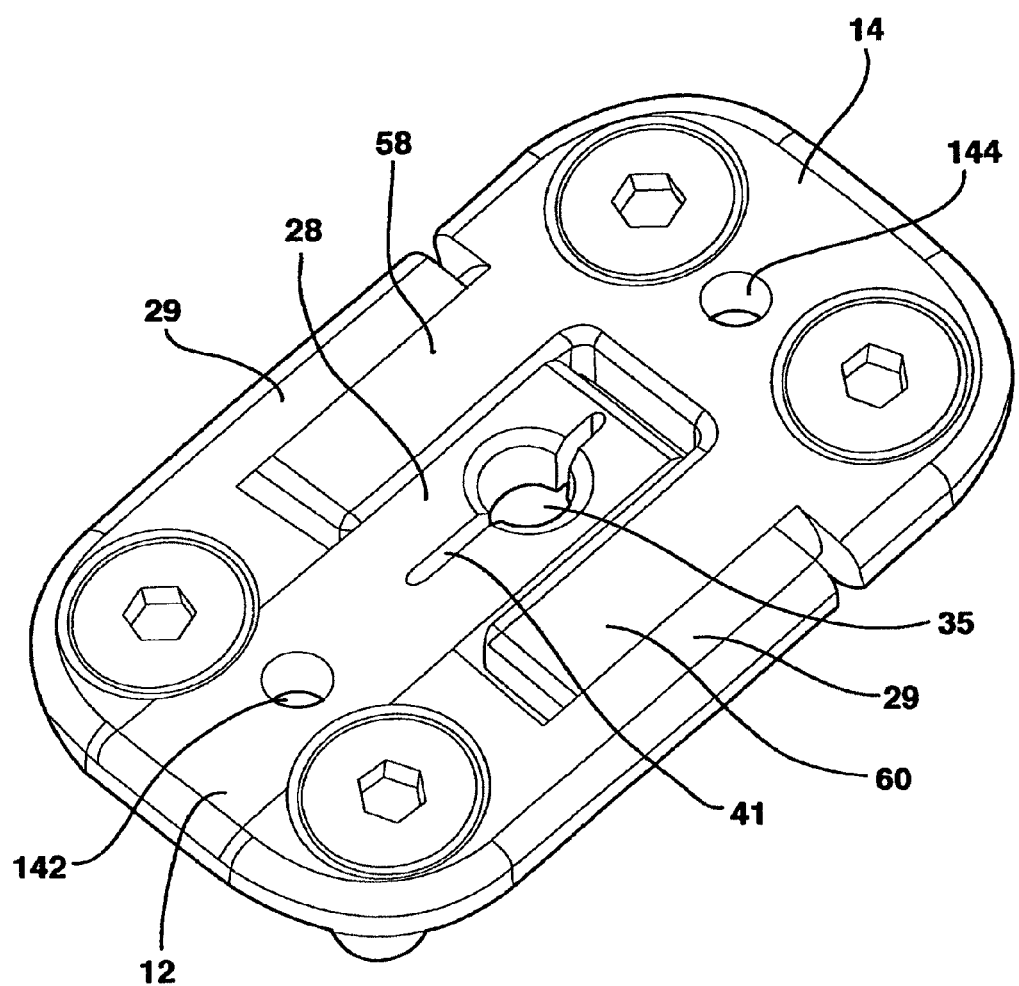
FIG. 29 is a perspective view of the static compression device of FIG. 28 without the locking screw in place.
Figure 31:
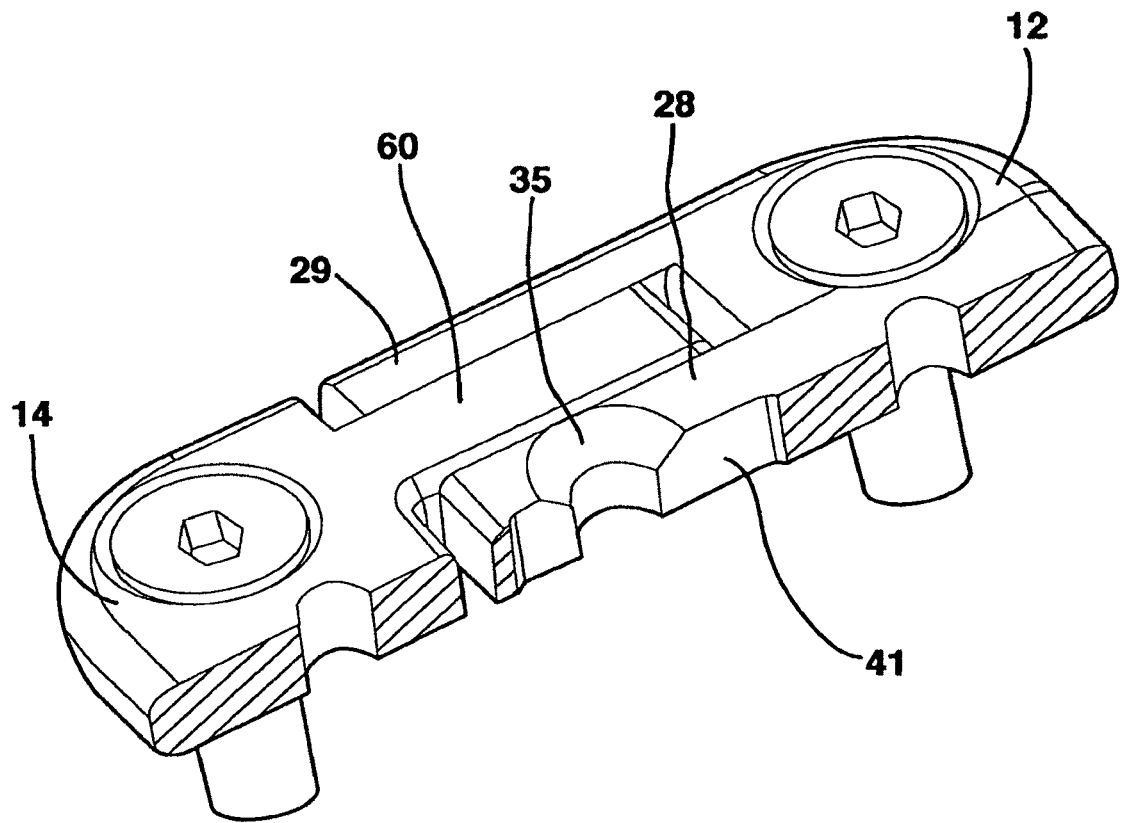
FIG. 31 is a cross-sectional perspective view of the static compression device of FIG. 28 without the locking screw in place.
Figure 32:
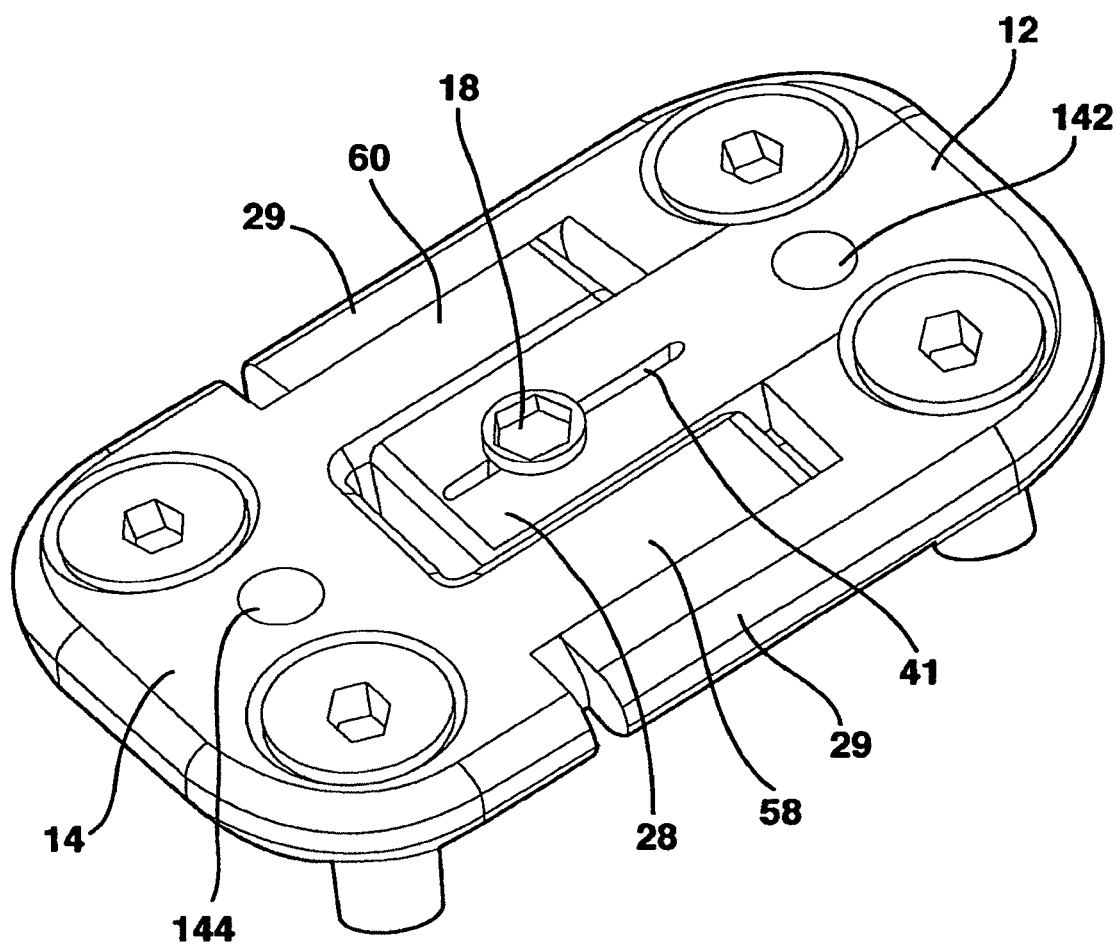
FIG. 32 is a perspective view of the static compression device of FIG. 28 without an alternate embodiment of the locking screw in place.

As mentioned above, the static compensating compressor 590 is able to apply distraction pressure to the vertebral bodies through the use of a turnbuckle 594 (FIG. 26). The threaded nut 596 has a pair of threaded holes 612. The threaded holes 612 are threaded in opposite directions (i.e., with right and left handed threads) as is well understood in turnbuckles. The threaded inserts 598 each have a threaded end 614 and a non-threaded end 616 to which a guide rod 602 is attached. The guide rods 602 are preferably attached to the non-threaded ends 616 through springs 600 that have a low spring force. Springs 600, when used, apply a low biasing force to the turnbuckle 594 to remove looseness in the connection between the turnbuckle 594 and the arms 114, 116. In another embodiment, the guide rods 602 may be attached directly to the non-threaded ends 616. The threaded inserts 598 are also each threaded on their threaded ends 614 in opposite directions (i.e., with right and left handed threads) and are mated with the threaded holes 612 of the threaded nut 596 so that as the threaded nut 596 is rotated in a first direction, the threaded inserts 598 are drawn into the threaded holes 612 and as the threaded nut 596 is rotated in a second direction, the threaded inserts 598 are moved out of the threaded holes 612. As a result, as the threaded nut 596 is rotated in a first direction, the turnbuckle 594 expands in length and as the turnbuckle 594 is rotated in a second direction opposite the first direction, the turnbuckle contracts in length.

The turnbuckle 594 is preferably attached between and applies a preload to the handles 118, 120 of the anus 114, 166 of the compressor 90. However, the turnbuckle 594 may also be attached between and apply a preload to the distal ends 126, 128 of the arms 114, 166 of the compressor 90. In either embodiment, the turnbuckle 594 is fitted between the arms 114, 116, either between the handles 118, 120 or distal ends 126, 128 preferably in slots 618, secured with pins 620 or other suitable retaining devices well understood in the art. In a variant of this embodiment, the pins 620 could be quick release pins, allowing the turnbuckle 594 to be quickly removed once the null point is found, as explained below, so that the compressor 90 would be used thereafter without the turnbuckle 594.

Once the turnbuckle 594 is attached to the arms 114, 116, by turning the threaded nut 596, the turnbuckle 594 expands or contracts (depending on the direction the threaded nut 596 is rotated) thereby applying a preload in either a compression or distraction direction to the arms 114, 166 of the compressor 90 and thus to the SC device 10 and ultimately to the vertebral bodies. This preload allows the vertebral segment that the SC device 10 is spanning to become unloaded or lifted. By "lifted" or "lift-off" we mean that a distraction force has been applied to the vertebral segment by the compressor 90 and SC device 10 to the point where the distraction force is equal to the anatomical compression force applied to the vertebral segment by the patient's own muscles and ligaments. At this point, called the null point, there is a net zero force applied to the affected vertebral segment so that the affected vertebral bodies separate or "lift-off" of each other slightly which separation is visually ascertained by the physician.

Once lift-off has been determined, and consequently, the null point established, a button is pushed on the display 608, on the CPU 606 itself or otherwise, including remotely, to alert the CPU 606 that strain measured by the strain gauge 610 at that point is the null point. As a result, the CPU 606 directs the display 608 to indicate a zero reading at that point.

At this point, the turnbuckle 594 is preferably removed from the compressor 90. As the turnbuckle 594 is removed, the patient's anatomical compression force will be applied to the affected vertebral segment. This compression force will be transferred through the SC device 10 to the compressor 90 where the strain gauge 610 will measure the anatomically applied compression force and the CPU 606 will direct the display 608 to indicate the anatomically applied compression force. Thereafter, the surgeon applies an additional compressive force to the SC device 10 which additional compressive force will be sensed by the strain gauge 610 combined with the compressive force applied by the patient's own anatomy. As a result, the CPU 606 will determine the total compressive force applied to the vertebral segment (i.e., the summation of the patient's own anatomical compressive force and the compressive force being applied by the physician by the compressor 90) which total compressive force is displayed on the display 608. The physician then applies the additional compressive force to the vertebral segment until a desired total compressive force for maximum therapeutic value is obtained.

If the force indicator 592 is set to a null point before distraction pressure is applied to the vertebral segment by the turnbuckle 594, the force indicator 592 will also indicate the distraction pressure applied to the vertebral segment by the turnbuckle 594. At the point where lift-off occurs, the display 608 will indicate the amount of distraction pressure being applied by the turnbuckle 594 which equals the amount of compression force that is applied by the patient's own anatomy. This amount of compression force is also potentially valuable information in that the amount of compression force anatomically applied by the patient may be used by the physician to determine the overall health and strength of the patient's inherent anatomical compression mechanism. Thereafter, the physician may set the force indicator 592 to zero as described above to indicate the null point for the application of compression force also as described above.

In a variant to the embodiments of the compression device 90 described above, a small cannula 158 is attached to the compression device 90 at the pivot 130. The cannula 158 is directed downward toward the SC device 10. This cannula 158 is intended to receive a special screwdriver 160 that activates the locking mechanism 88 of the SC device 10 when the desired compression is achieved. The screwdriver 160 is inserted through the cannula 158 into the loosened locking mechanism 88 as the compression device 90 engages the male plate 12 and female plate 14. Thus, it is possible for the surgeon to maintain compression across the graft with one hand on the compression device 90, to determine the degree of compression achieved on the SC device 10 by visualizing the compression gauge 146, and to activate the locking mechanism 88 of the SC device 10 with the other hand, causing the SC device 10 to become a rigid construct and preventing further movement of the vertebral bodies from occurring.

Alternately, the physician may use the screwdriver 160 without inserting it through the cannula 158 or may use the screwdriver 160 in an embodiment of the compression device 90 that does not include a cannula 158. Further, in any of the embodiments of the compressor 90, the compressor 90 may be disposable or reusable.

One mechanism of fixing the bone screws 43 to the male plate 12 at a rigid predetermined angle is described as follows. As mentioned above, bone screws 43 fix the male plate 12, the female plate 14 and the interconnecting plate, 15, if present, to the vertebral bodies. The bone screws 43 may be machined, as is common for such screws, with two separate sets of threads, one on the shaft of the screw 43, the second set on the head of the screw 43. These threads are distinct from each other in that they have different pitches and distinct outer diameters. The pitch and outer diameter of the threads on the shaft of the screw 43 are that of a standard cancellous bone screw. In order to engage the main male plate 12, the diameter of the head 45 of the bone screw 43 head is significantly larger than the diameter of the threads on the shaft of the bone screw 43. However, the threads on the bone screw 43 are smaller in outer diameter and tighter in pitch than the bore of the screw receiving holes 38. These threads are machined to engage threads of similar pitch and diameter in the screw receiving holes 38 of the male plate 12.

The screw receiving holes 38 are machined to project the screw 43 into the vertebral body at a predetermined angle determined to be most advantageous for fixing the device 10 to the vertebral bodies. Thus, by engaging the threads on the head 45 of the screw 43 with those in the screw receiving hole 38, the screw 43 projects into the vertebral body at the predetermined angle and maintains a rigid fixed relationship with the male plate 12.

The interaction between the bone screws 43 and the SC device 10 described above is one of the many ways that bone screws 43 can be connected to the SC device 10. However, it is well understood in the art that there are other commercially available ways to connect devices like the SC device 10 to vertebrae that could also be used. As a result, it is intended that any method of connecting the SC device 10 to vertebral bone so that there is a rigid fixed relationship between the SC device 10 and the bone may be used with the SC device 10 of the present invention.

The mechanism of fixing the screws 43 to the female plate 14 at a rigid predetermined angle is similar to the mechanism for fixing the screws 43 to the male plate 12 at a rigid predetermined angle as described above. Again, the bone screws 43 are machined, as is common for such screws, with two separate sets of threads, one on the shaft of the screw 43, the second set on the head of the screw 43. These threads are distinct from each other in that they have different pitches and distinct outer diameters. The pitch and outer diameter of the threads on the shaft of the screw 43 are that of a standard cancellous bone screw. In order to engage the female plate 14, the inner diameter of the screw head 45 is significantly larger than the inner diameter of the threads on the shaft. However, the threads on the screw head 45 are smaller in outer diameter and tighter in pitch than the bore of the screw receiving holes 82. These threads are machined to engage threads of similar pitch and diameter in the screw receiving holes 82 of the female plate 14. The screw receiving holes 82 are machined to project the screw 43 into the vertebral body at a predetermined angle. Thus, by engaging the threads on the head 45 of the screw 43 with those in the screw receiving holes 82, the screw 43 projects into the vertebral body at the predetermined angle and maintains a rigid fixed relationship with the female plate 14.

The SC device 10 as described in the embodiment above has the option of using fixed angle screws. However, variable angle screws 43 may be used with the SCD device 10 as long as when these screws 43 are placed through the male plate 12, female plate 14 or interconnecting plate 1 S into bone, their relationship with the respective plate 12, 14 or 15 becomes rigid. There are numerous methods of attaching bone screws to plates well understood in the art, all of which may be used with this device. It is important that the relationship between the screws and the plates 12, 14, 15 becomes rigid once the screws are placed in order to avoid "toggle" of the screws during the compression maneuver. "Toggle" must be avoided, because if it occurs, actual compression may be significantly less than measured.

Most currently available non-adjustable plates have the option to place screws into the bone at a variety of different angles to obtain optimum purchase. While this is necessary to position static plates, it is not necessary in the SC device 10. In fact the sliding capability that the SC device 10 has in the unlocked arrangement renders the common use of variable screws superfluous. Nevertheless, any type of screw may be used with the SC device 10 as long as a mechanism exists for rigidly fixing the screw to the plate.

The importance of having screws 43 that are rigidly fixed to the male plate 12 and female plate 14 at a predetermined angle is that compression occurs through the entire SC device 10 (the sliding components of the SC device 10 (male plate 12 and female plate 14 and the two rigidly attached screws)), rather than through the screws individually. Also, as mentioned, the bottom side 36 of the male plate 12 and the bottom side 54 of the female plate 14, and of the interconnecting plate 15 if present, are roughened, allowing the SC device 10 to "grip" the vertebral body. These characteristics in combination provide for a much larger surface area to compress against (the contact of the bottom side 36 and bottom side 54 on the anterior surface of the vertebrae as well as the two rigidly fixed bone screws in the male plate 12 and female plate 14, respectively). This results in a much more even compression against the entirety of the interbody graft and minimizes the potential for screw cutout or bony failure.

For purposes of illustrating the operation of locking mechanism 88 of the invention in the embodiment shown in FIGS. 1-14, a variant of the embodiment described above will be used. In this variant, shown in FIGS. 15-17, there is no interconnecting plate 15. Instead, the male plate 12 and female plate 14 intermesh directly through the interaction of the central protrusion 28 and side protrusions 29 of the male plate 12 and the left and right guides 58, 60 of the female plate 14. In describing the operation of the SC device 10, it is to be understood that the concepts described apply as well to the interaction between the male plate 12 and one end of the interconnecting plate 15 and the interaction between the opposite end of the interconnecting plate 15 and the female plate 14.

Figure 15:
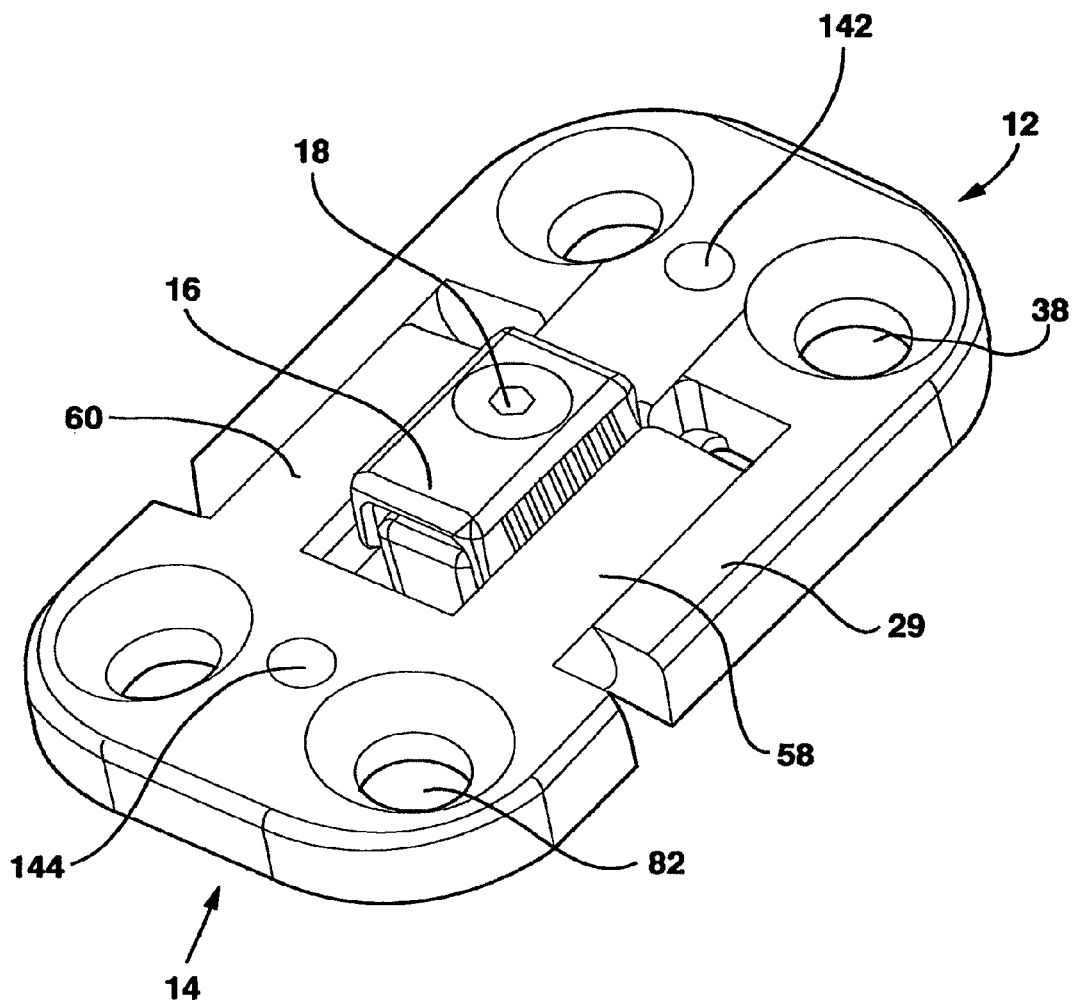
FIG. 15 is a perspective view of the static compression device of FIG. 1 in an embodiment without the interconnecting plate.

In use, the central protrusion 28 is inserted into the protrusion receiving channel 56 (FIG. 15). Because protrusion receiving channel 56 is dimensioned to receive central protrusion 28 with the locking clamp 16 in place, central protrusion 28 is precisely located and retained within the protrusion receiving channel 56. In this position with the locking clamp 16 in place on the top surface 30 of central protrusion 28, the ridges 46 and valleys 48 on the parallel sides 96 of locking clamp 16 come into loose contact with the inner surface 61 of left guide 58 and right guide 60 of the female plate 14. (FIG. 15) The locking screw 18 is passed through the screw hole 93 so that its distal end 110 comes into contact with and is threaded into the threaded hole 35 a sufficient amount to locate the distal end 110 of the locking screw 18 in the threaded hole 35 but not a sufficient amount to deform the locking clamp 16.

Bone screws are passed through the screw receiving holes 38 and 82 and into the vertebral bone. These bone screws are screwed into the vertebral bone until the heads of the bone screws seat into the basins 40, 84 of the male plate 12 and female plate 14, respectively.

The compression device 90 is then used to apply the desired compression to the SC device 10. The pins 132 are placed in the notches 142, 144 and the handles 118, 120 are squeezed together. As a result, compression pressure is applied to the male plate 12, female plate 14 and interconnecting plate 15 if present, and thereby to the vertebral bone through the bone screws.

As mentioned above, where a gauge 146 is present, the amount of compressive force applied to the SC device 10 can be ascertained.

Figure 16:
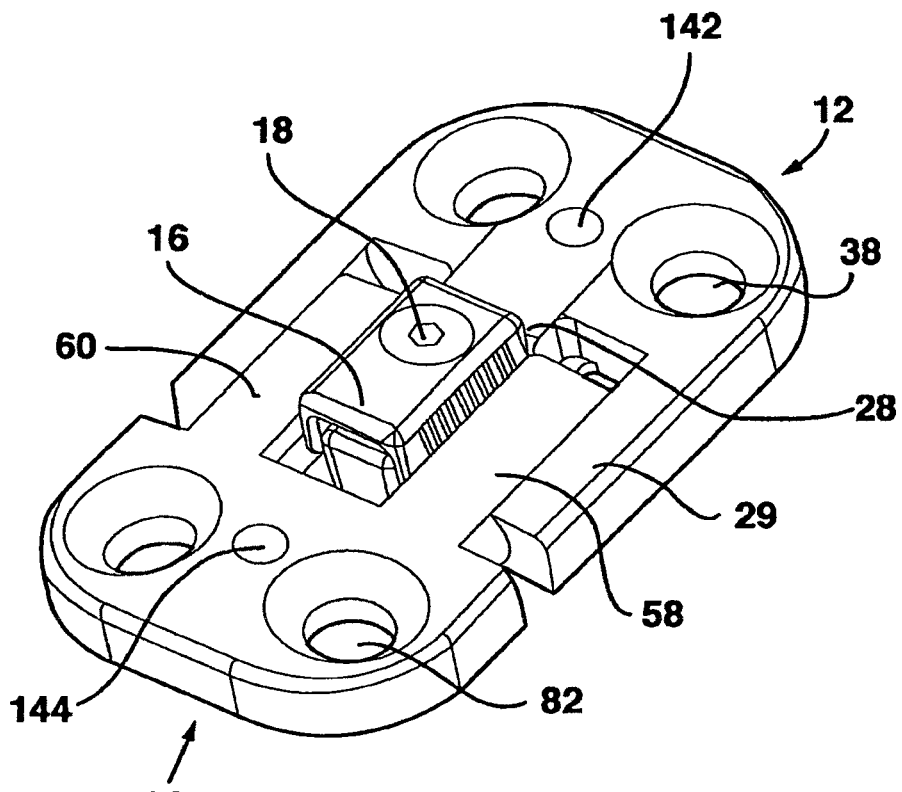
FIG. 16 is a perspective view of the static compression device of FIG. 15 in an unlocked configuration.
Figure 17:
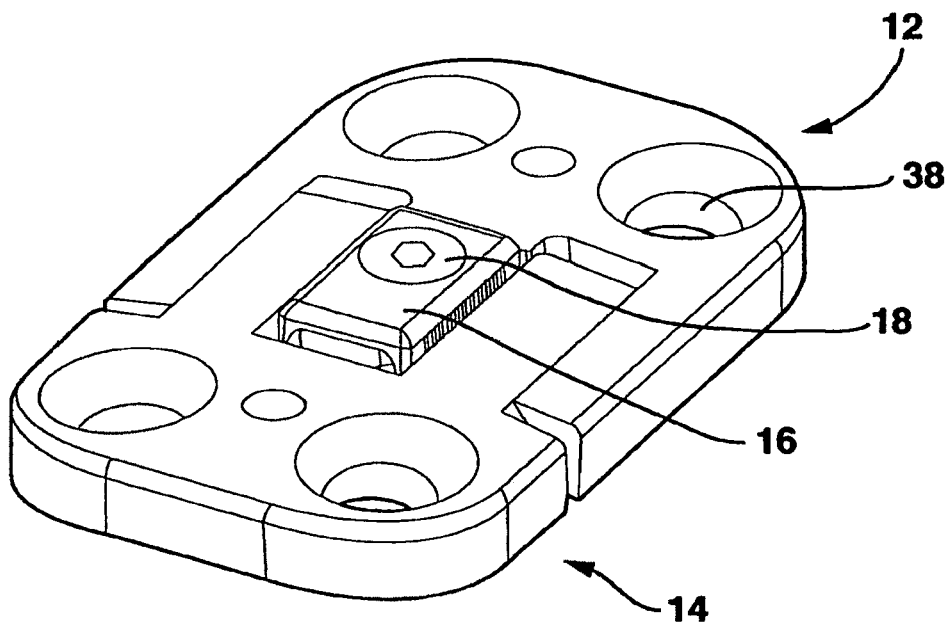
FIG. 17 is a perspective view of the static compression device of FIG. 15 in a locked configuration.
Figure 18:
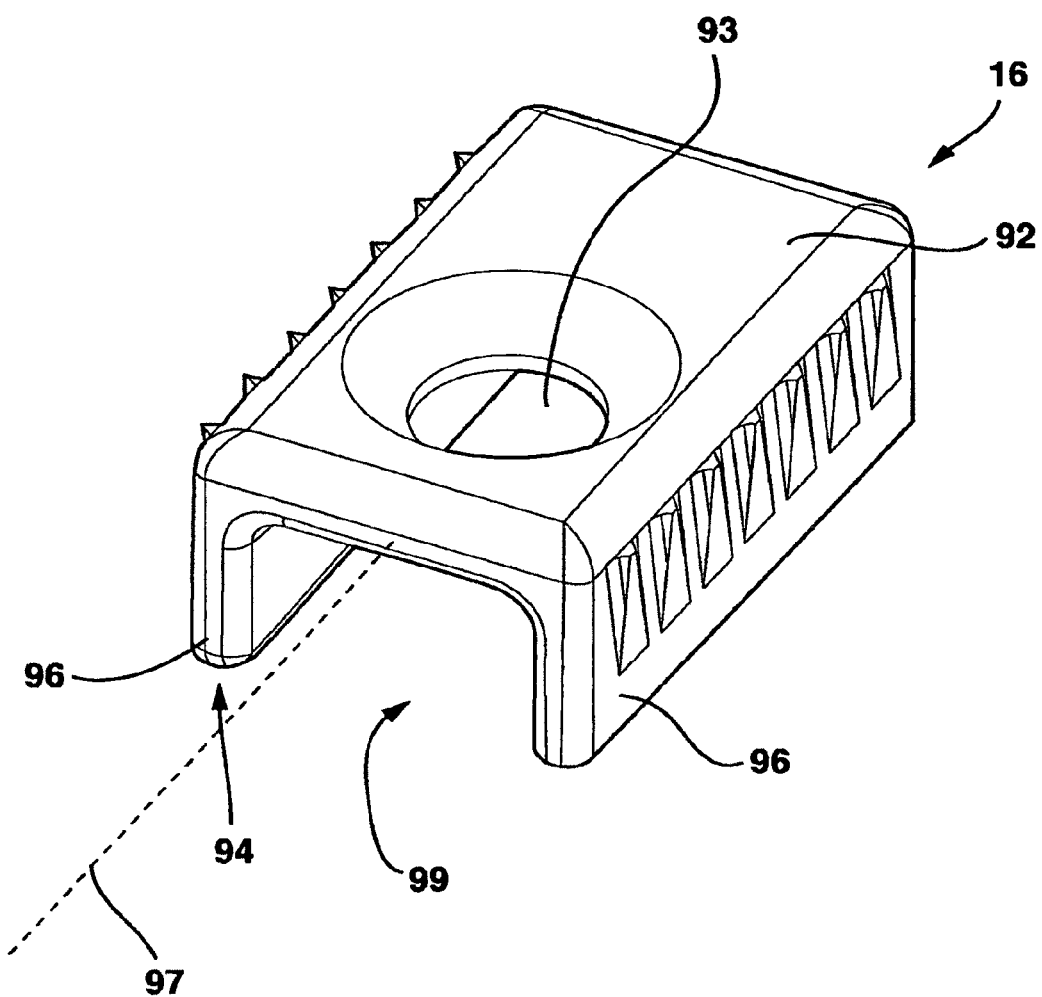
FIG. 18 is a perspective view of the locking clamp of the static compression device of FIGS. 1 and 15.
Figure 19:
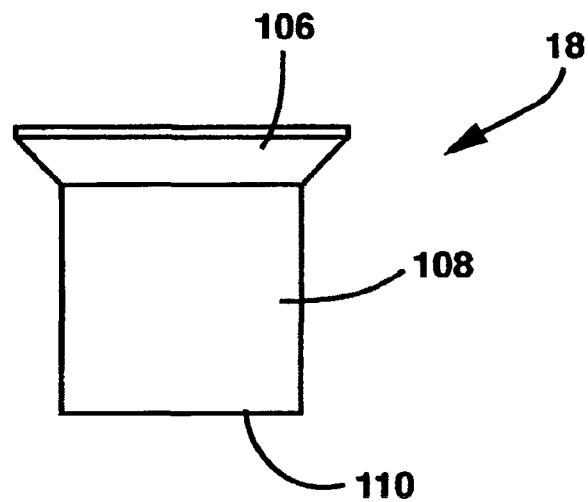
FIG. 19 is a side view of the locking screw of the static compression device of FIG. 1.
Figure 30:
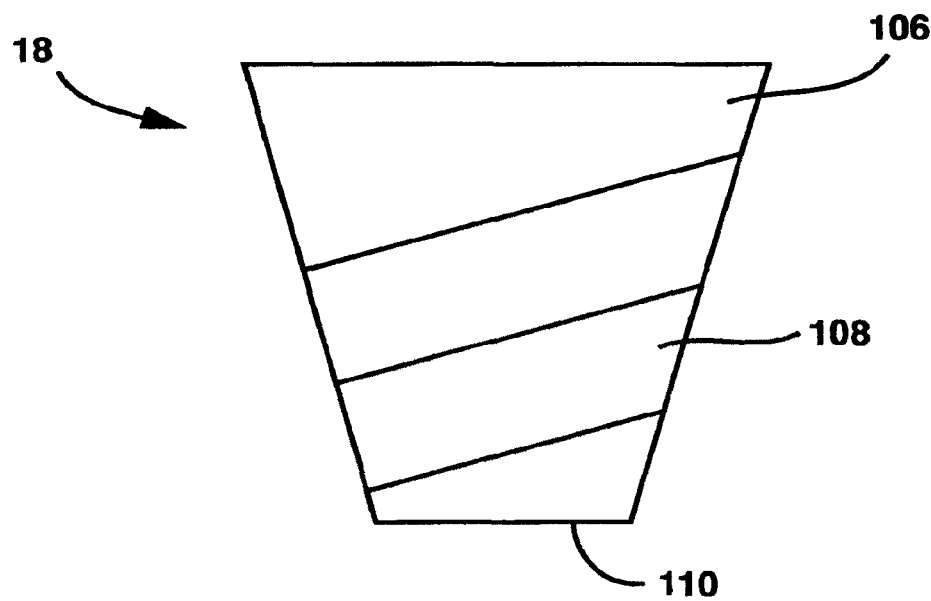
FIG. 30 is a side view of the locking screw of the static compression device of FIG. 28.
Figure 20:
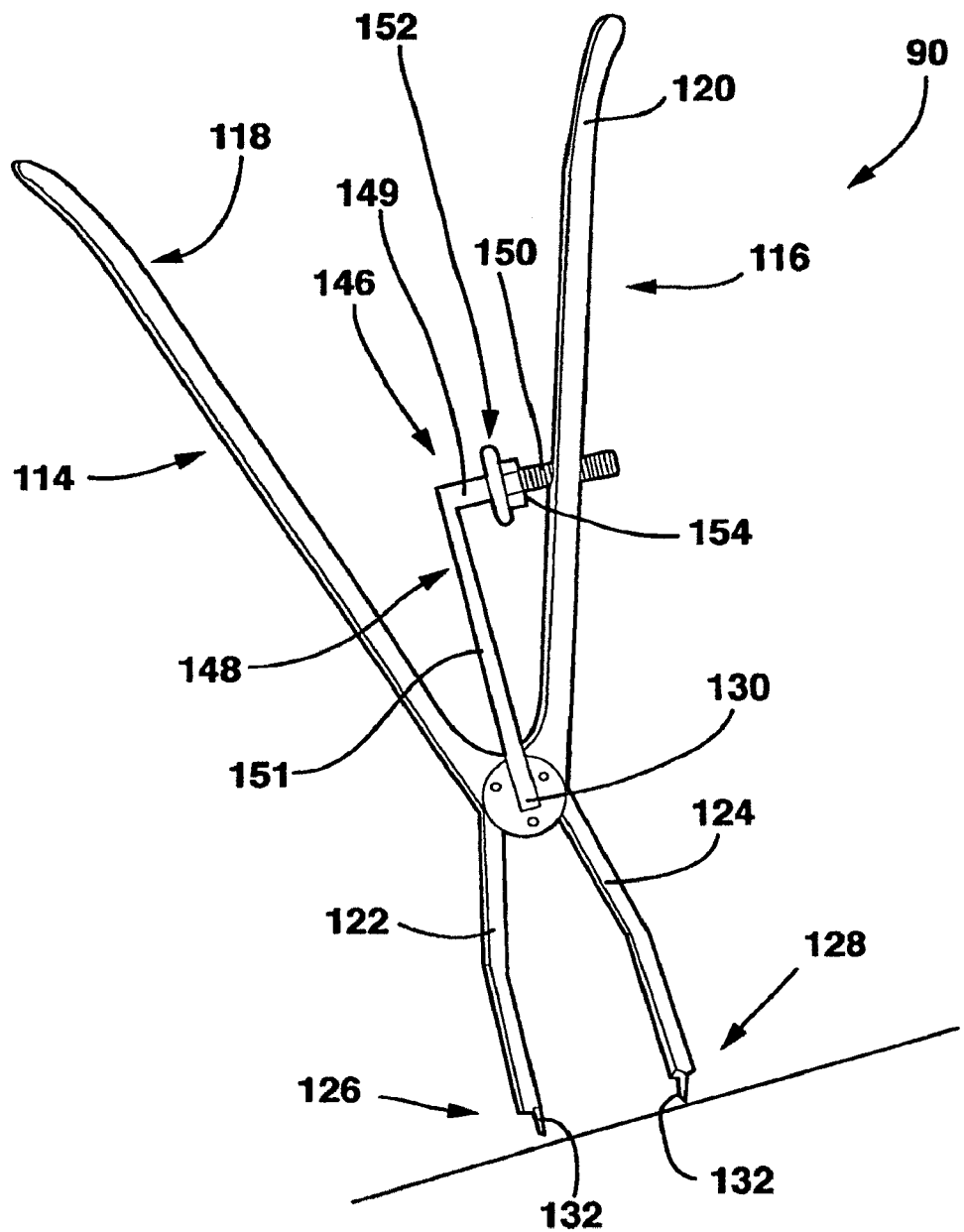
FIG. 20 is a perspective view of one embodiment of the compression tool of the present invention.

As shown in FIGS. 16 and 17, when the male plate 12 is moved into an intermeshing position with the female plate 14 and the appropriate amount of compression is applied to the SC device 10 through the compression device 90, the screwdriver 160 is coupled to the head 106 of the locking screw 18. The screwdriver 160 is rotated so that the threaded body 108 of locking screw 18 is threaded into the threaded hole 35. The locking screw 18 is then screwed further onto the central protrusion 28 on the male plate 12 so that the head 106 contacts the top surface 92 of the locking clamp 16.

Once the head 106 has contacted the top surface 92, further rotation of the locking screw 18 will cause the head to be forced into the material of the top surface 92 of the locking clamp 16. This will cause the locking clamp 16 to interfere so that the parallel sides 96 will be forced into engaging and locking contact with the inner surfaces 61 of the left and right guides 58, 60 on the female plate 14 or the interconnecting plate 15. This outward compression from the interference fit is transferred through the left and right guides 58, 60 to cause engaging and locking contact between the outer surface 63 of the left and right guides 58, 60 and the inner surface 37 of the side protrusions 29. The interaction between the head 106 and the screw hole 35 locks the locking clamp 16 against the right and left guides 58, 60. Once male plate 12 is secured with respect to the female plate 14, the compression device 90 is removed. As a result, the compression applied to the SC device 10 through the compression device 90 will be locked to the vertebral bone through the male plate 12 and female plate 14 (and interconnecting plate 15 if used) because these various components are locked in a fixed relationship to each other.

An alternate embodiment of the locking mechanism 88 is shown in FIGS. 28-32 and is described as follows. In this embodiment there is no locking clamp 16 and the locking screw 18 (FIG. 30) is large in diameter and is tapered from the head 106 to the distal end 110 so that the diameter of the head 106 is significantly larger than the diameter of the distal end 110. In addition, the diameter of head 106 of the locking screw 18 is greater than the width of the central protrusion 28. Further, the threaded hole 35 of the central protrusion 28 of the male plate 12 is fashioned in a threaded tapered fashion so that the locking screw 18 fits into the threaded hole 35. In this embodiment the central protrusion 28 may include a slot 41 through which the threaded hole 35 passes to allow maximal deformation of the central protrusion 28 along the length of the central protrusion 28.

Thus, when appropriate compression has been applied to the vertebral bodies by the SC device 10, the locking mechanism 88 is engaged by advancing the locking screw 18 into the threaded hole 35. The advancement of the locking screw 18 into the threaded hole 35 deforms the outer aspect of the central protrusion 28 which surrounds the threaded hole 35 thereby causing this portion of the central protrusion 28 to expand and interfere with the inner surface 61 of left guide 58 and right guide 60 of the female plate 14. The presence of the slot 41 helps the deformation of the outer aspects of the central protrusion 28 by making it easier for the two sides of the central protrusion 28 to move away from the threaded hole 35 under the influence of the locking screw 18. This outward compression from the interference between expanded central protrusion 28 and left and right guides 58, 60 is transferred through the left and right guides 58, 60 to cause engaging and locking contact between the outer surfaces 63 of the left and right guides 58, 60 and the inner surface 37 of the side protrusions 29.

It should be noted that the SC device 10 is a modular and expandable device. The characteristics of this device allow it to be disassembled in vivo and expanded to immobilize adjacent vertebral segments (or other bone pieces or segments) by the insertion of one or more interconnecting plates 15 to form an interconnecting span as described above.

Thus, should subsequent surgery be required, as for example, in the case of adjacent segment disease (the segment adjacent to a fused segment undergoing accelerated degeneration), it is not necessary to expose the entirety of the SC device 10 and remove it to extend the fusion to the adjacent segment (as is the case with nearly all current plates). Instead, an end portion of the SC device 10 (e.g., either the male plate 12 or female plate 14) may be removed (leaving the remainder of the SC device 10 intact), the fusion completed and the SC device 10 simply expanded to include the newly fused segment by inserting one or more interconnecting plate IS, then reapplying the end portion (either the male plate 12 or female plate 14, respectively) of the SC device 10 to the newly fused vertebrae, applying compression as explained herein and locking and securing the SC device 10.

Figure 33:
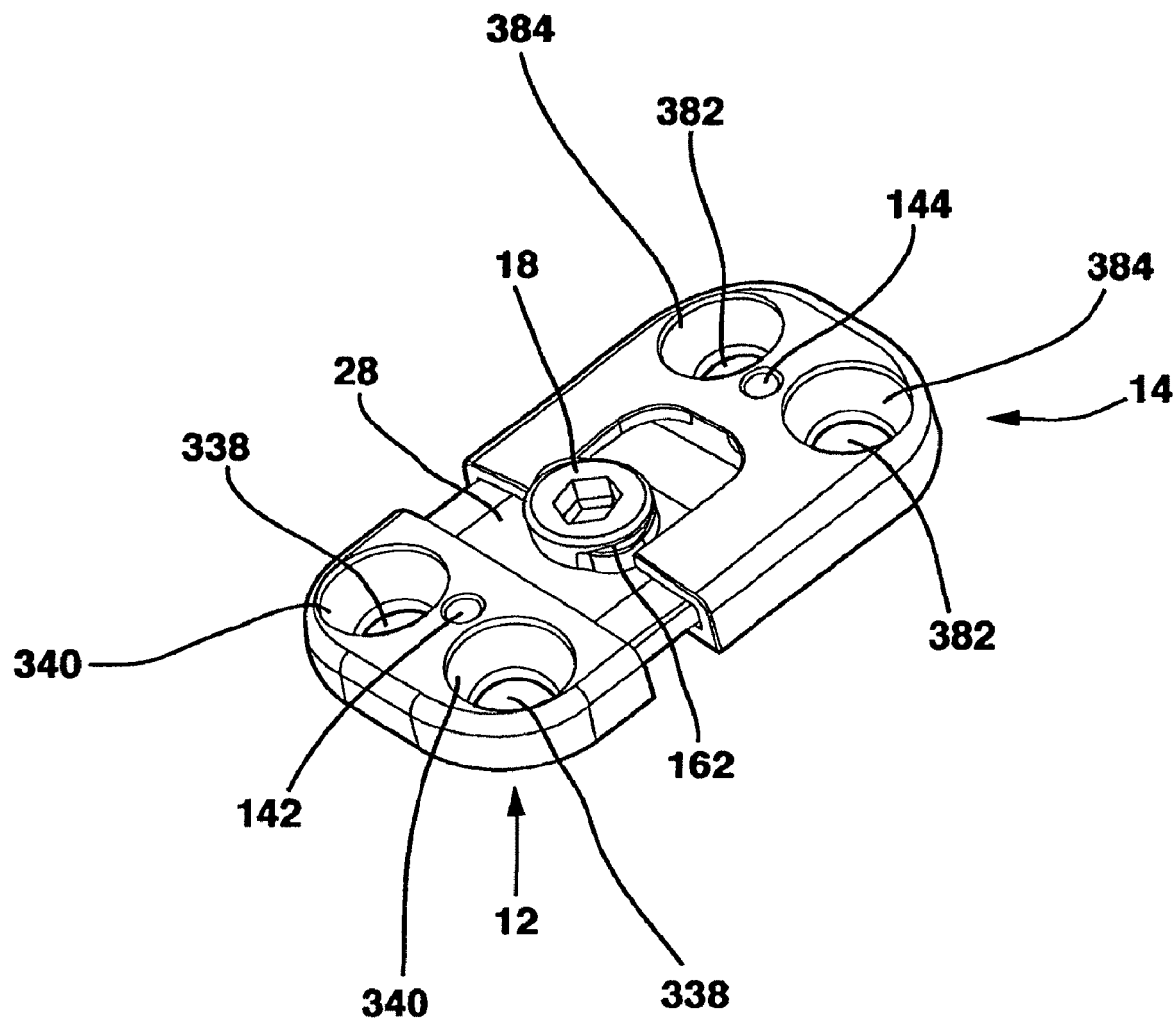
FIG. 33 is a perspective view of an alternate embodiment of the static compression device.
Figure 34:
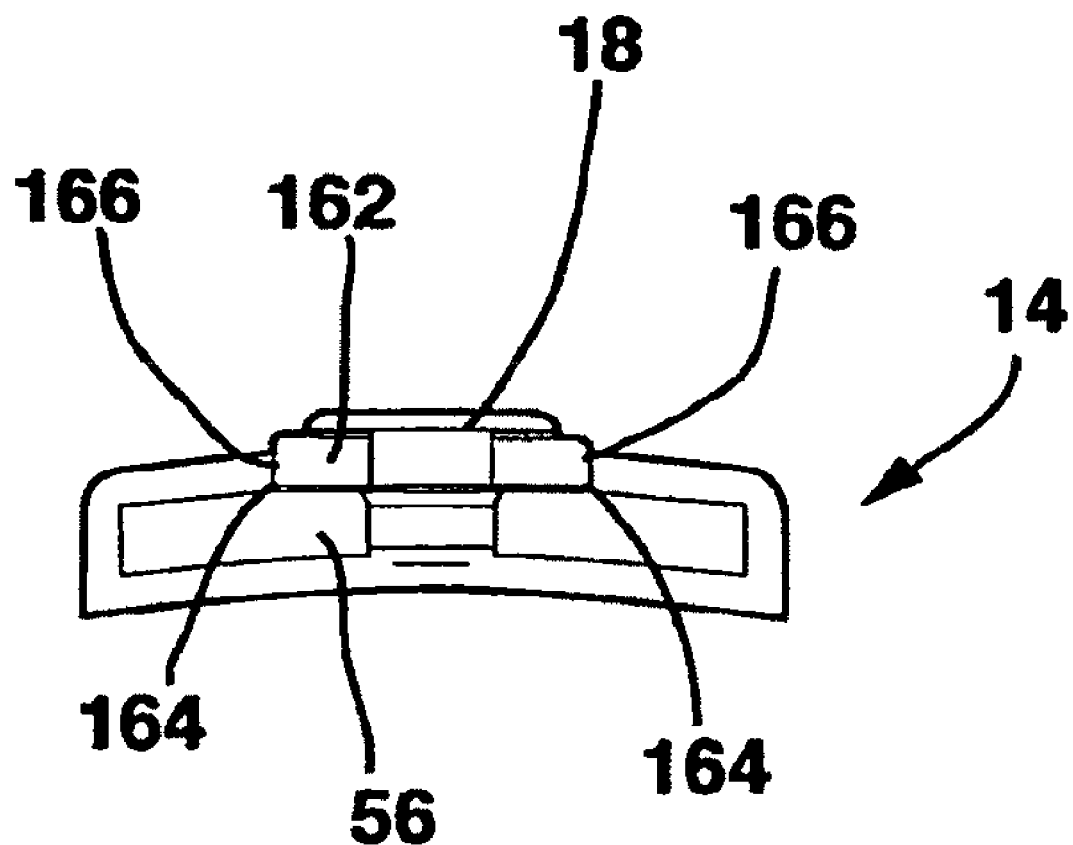
FIG. 34 is an end view of the female plate of the static compression device of FIG. 33 with the locking screw and cam in place.
Figure 35:
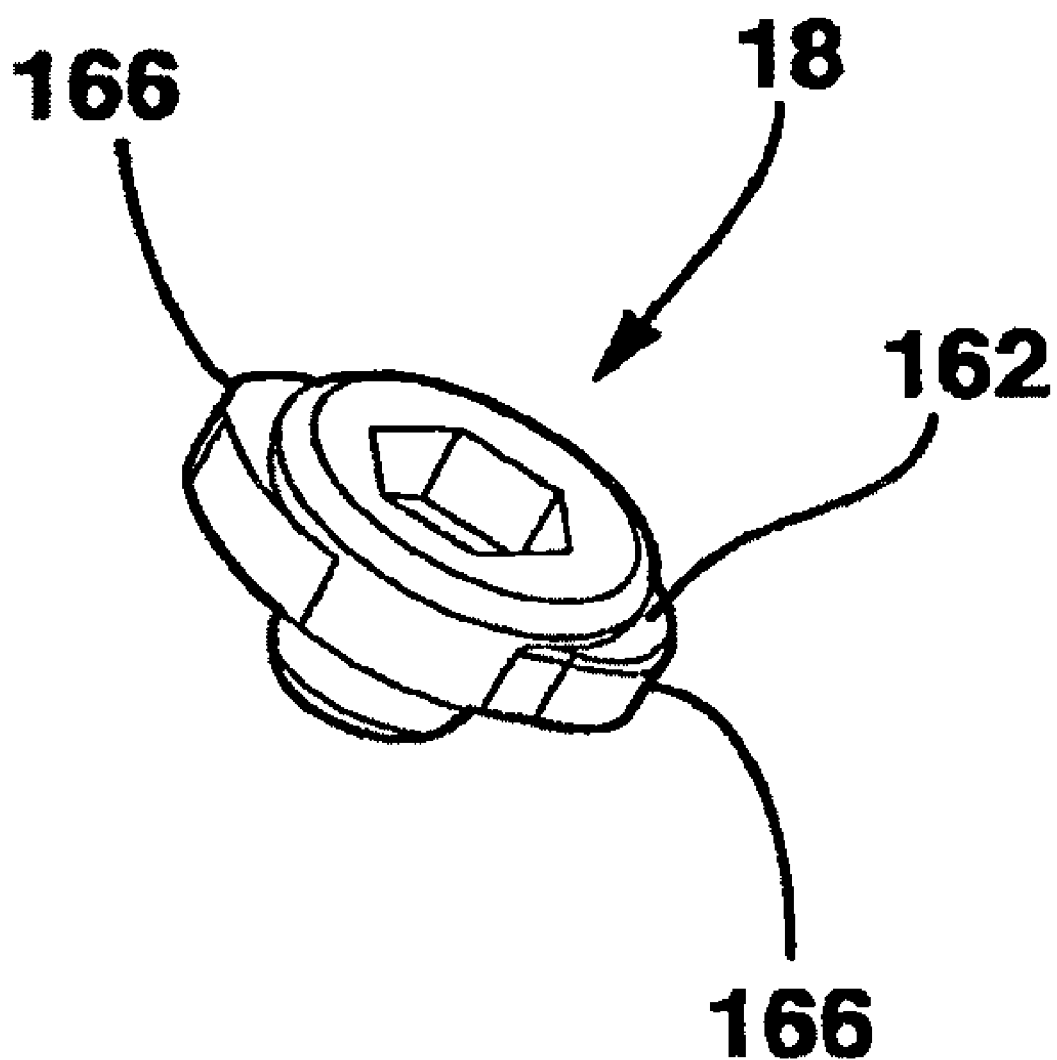
FIG. 35 is a perspective view of the locking screw and cam of the static compression device of FIG. 33.
Figure 36:
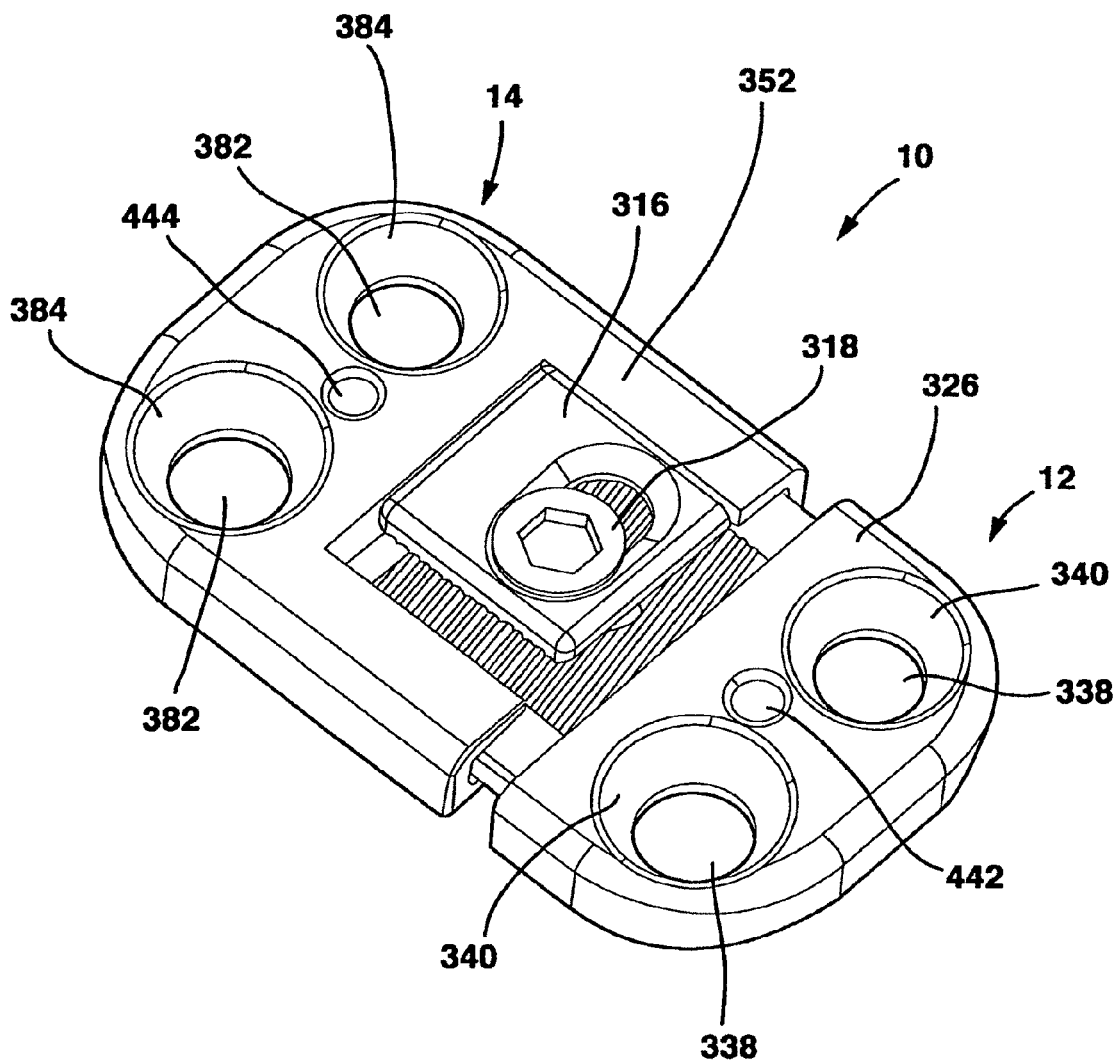
FIG. 36 is a perspective view of one embodiment of the static compression device of the present invention.
Figure 37:
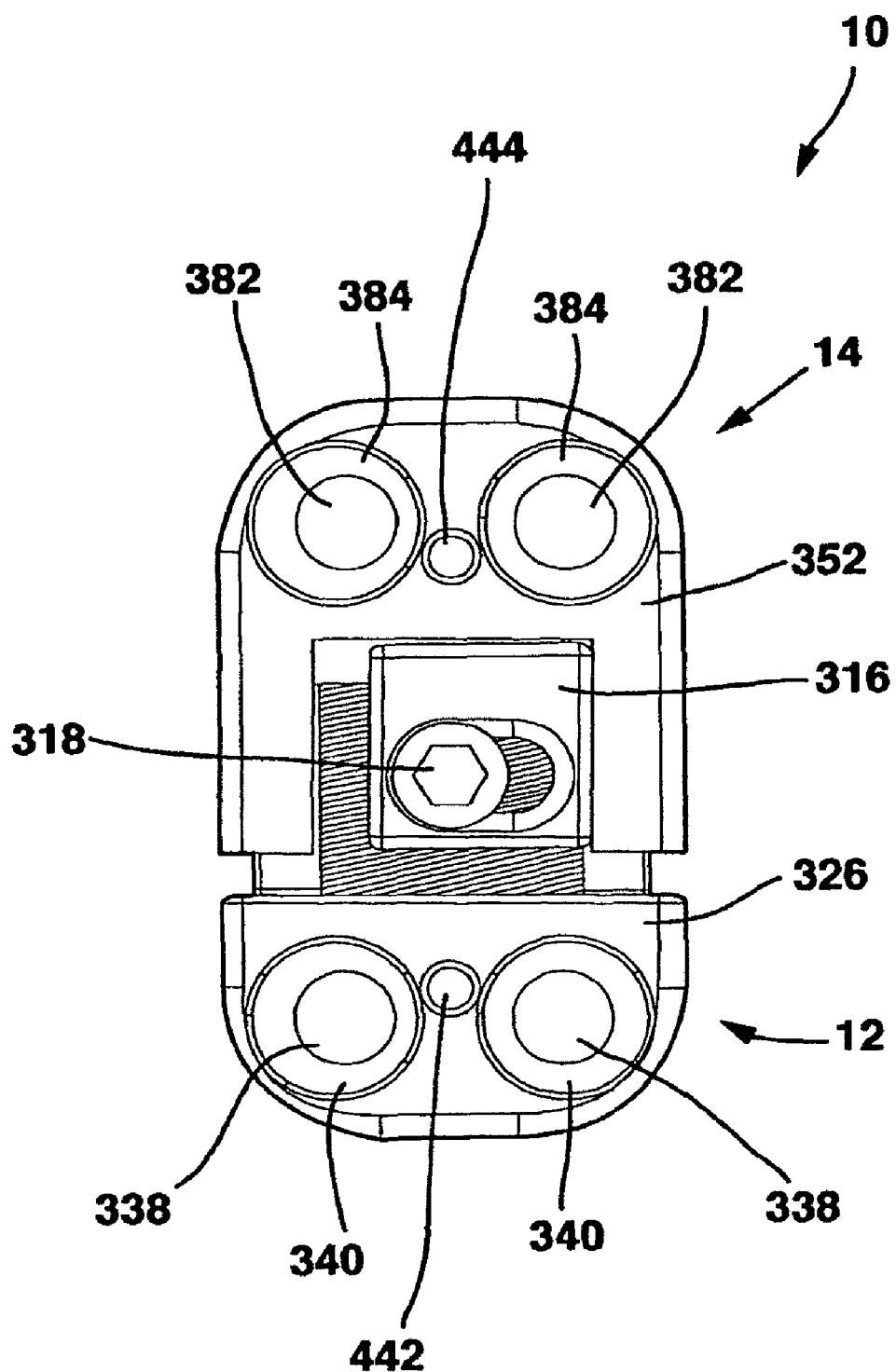
FIG. 37 is a top view of the static compression device of FIG. 36.
Figure 38:
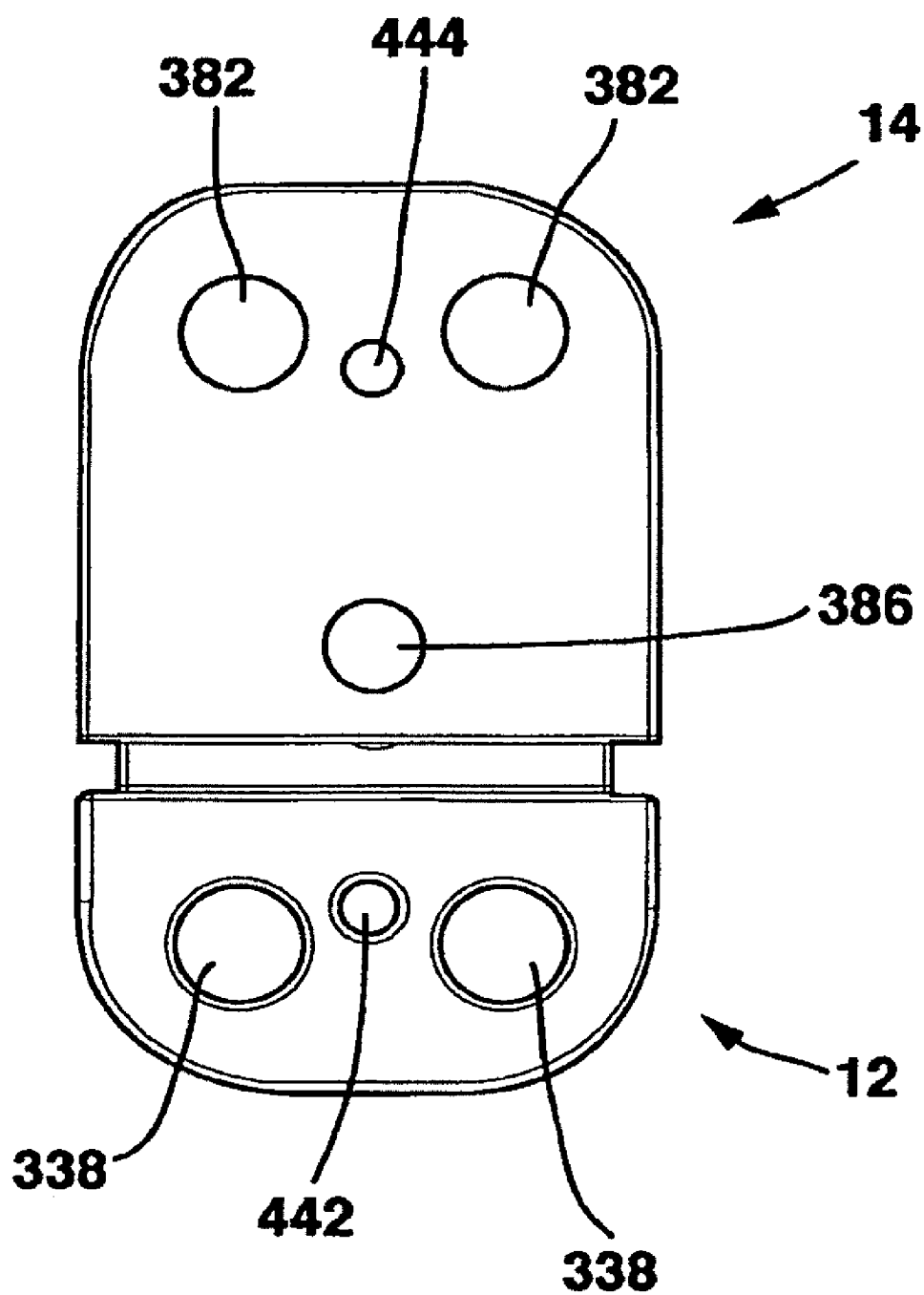
FIG. 38 is a bottom view of the static compression device of FIG. 36.

An alternate embodiment of the SC device 10 is shown in FIGS. 33-35. In this embodiment, the locking screw 18 of the locking mechanism 88 is modified to include a cam 162 that rotates around the locking screw 18 below the head 106 (FIG. 35). Further, the edges of channel 80 form a track 164 (FIG. 34) dimensioned to receive and constrain the cam 162 within the track 164 in a relatively conformal manner. In addition, in this embodiment of the locking mechanism 88, there is no locking clamp 16 and the central protrusion 28 does not have the protrusion ridges 50.

Cam 162 is relatively disk shaped with elongated opposed outer edges 166. The outer edges 166 resemble somewhat a "V" with the bottom of the V being farther from the body 108 than the open mouth of the V which rotates around the body 108 of locking screw 18. The locking screw 18 in this embodiment rotates freely with respect to cam 162. However, the cam portion can be rotated into contact with and engage the track 164 when rotated 90 degrees about the body 108. When the locking screw 18 is in the unlocked position, the male plate 12 is inserted into the protrusion receiving channel 56. With the cam 162 rotated so that the cam 162 does not contact the track 164, the cam 162 and the locking screw 18 move easily into the channel 80. Then the male plate 12 and the female plate 14 are moved to the desired position relative to each other, the cam 162 is rotated 90 degrees so that the cam 162 contacts the wall of the track 164 where such frictional contact prevents the male plate 12 from moving relative to the female plate 14. In addition, though both the locking screw 18 and the female plate 14, including the track 164 are preferably made of titanium, the locking screw 18 is of a significantly harder grade. In this way, as the locking screw 18 is rotated 90 degrees, because the cam 162 is present and has a cam shape, the cam 162 is forced into the track 164, effectively deforming the cam 162 and forming a "cold weld" with the track 164. In this way, a rigid, permanent fixation between the locking screw 18 and the male plate 12 to which it is attached and the female plate 14 through track 164 is achieved and compression is maintained. The SC device 10 in this embodiment is also designed to work with the compression device 90.

An alternate embodiment of the SC device 10 in a preferred embodiment shown in FIGS. 36-54 S also has a male plate 12 and a female plate 14. In addition, the SC device 10 in this embodiment also has a locking plate 316 and a locking screw 318 that, in combination with standard cancellous bone screws (not shown) fix the SC device 10 to the patient's vertebrae. This SC device 10 has a top side 320, a bottom side 322 and opposed medial sides 324.

The male plate 12 has a male main body 326 and a protrusion 328 extending away from the male main body 326. The protrusion 328 has a top surface 330 and a longitudinal axis 332. The male main body 326 is relatively flat with a top side 334 and a bottom side 336 and, in a preferred embodiment, has two screw receiving holes 338. The screw receiving holes 338 each have a bowl-shaped basin 340 on the top side 334 to receive the heads of the screws and a throughhole 342 through which the main body of the screws pass to come into contact with the vertebral body. The throughholes 342 are machined to have a S rigid relationship with the bone screws as will be described hereafter.

The bottom side 336 of the male plate 12 plate is preferable roughened, thereby allowing the bottom side 336 of male plate 12 to "grip" the vertebral body when the bottom side 336 is brought into contact with and is secured to the vertebral body by the interaction of the screws and the male main body 326 as described above.

As mentioned, the male plate 12 has a protrusion 328 with a top surface 330 and a longitudinal axis 332. Protrusion 328 is dimensioned to mate with and secure the male plate 12 with the female plate 14 as will be described in detail hereafter. The length of protrusion 328 along the longitudinal axis 332 is chosen to be slightly longer than the distance the SC device 10 is intended to provide compression over.

Protrusion 328 has a slot 344 extending entirely through it approximately perpendicular to the top surface 330. Protrusion 328 also has a series of alternating ridges 346 and valleys 348, collectively protrusion ridges 350, located on a portion of its top surface 330. Ridges 350 are preferable angled slightly with respect to the longitudinal axis 332 for a purpose to be explained hereafter.

The female plate 14 has a female main body 352 with a bottom side 354 and a protrusion receiving channel 356. Protrusion receiving channel 356 is comprised of a left channel 358, a right channel 360 and a connecting piece 362. Left channel 358 is basically "C" shaped with a top piece 370, bottom piece 372 and an outer piece 374. Although left channel 358 has been described as having a top piece 370, bottom piece 372 and outer piece 374, left channel 358 is preferable a single contiguous piece although it could be made of these separate segments connected together.

Right channel 360 has a top piece 370, a bottom piece 372 and an outer piece 374. Although right channel 360 has been described as having a top piece 370, bottom piece 372 and outer piece 374, right channel 360, like left channel 358, is preferable a single contiguous piece although it could be made of these separate segments connected together.

Connecting piece 362 connects the left channel 358 to the right channel 360 at the respective bottom pieces 372. In the preferred embodiment, connecting piece 362 is integrally formed with the bottom pieces 372 although it could be made of these separate segments connected together. Connecting piece 362 has a threaded hole 376 that extends into connecting piece 362.

Protrusion receiving channel 356 is dimensioned to snugly receive the protrusion 328 so that the protrusion 328 is "captured" and held in the protrusion receiving channel 356 by relatively conformal physical contact between the outer surface of the protrusion 328 and the inner surfaces of the left channel 358, right channel 360 and connecting piece 362.

The female main body 352 also has an upper surface 378 and a channel 380 formed in the upper surface 378 between the left channel 358 and the right channel 360. Channel 380 extends entirely through the upper surface 378.

The female plate 14, also in a preferred embodiment, has two screw receiving holes 382. These screw receiving holes 382 receive standard cancellous bone screws (not shown) that are threaded into the bone of the vertebrae. In similar fashion to screw receiving holes 338, the screw receiving holes 382 also have a bowl-shaped basin 384 on the upper surface 378 to receive the heads of the bone screws and a throughole 386 through which the main body of the bone screws pass to come into contact with the vertebral body. The throughholes 386 are machined to provide a rigid relationship with the bone screws.

The SC device 10 has a locking mechanism 388. The locking mechanism 388 includes locking plate 316 and locking screw 318 as well as the ridges 346 and valleys 348 on the top surface 330 of protrusion 328 of the male plate 12 and the threaded hole 376 and channel 380 of female plate 14 as described below. Locking mechanism 388 converts "active" compression applied by the surgeon using the compression device 90 described above interacting with the SC device 10 at the time of surgery to "static" compression after surgery. The locking mechanism 388 also provides rigid fixation to the SC device 10 to optimize bone healing and preventing further settling from occurring.

The locking plate 316 has a top surface 392, a bottom surface 394 and parallel sides 396. The bottom surface of locking plate 316 preferably has a series of ridges 398 and valleys 400, collectively locking ridges 402, of similar dimensions to the ridges 346 and valleys 348 of the protrusion 328 to locate and affix the locking plate 316 to the protrusion 328 as will be described hereafter. In a most preferred embodiment of the invention, the ridges 346 and valleys 348 of the protrusion 328 and the ridges 398 and valleys 400 of the locking plate 316 are angled slightly with respect to the longitudinal axis 332. Through this configuration, the ridges 398 and valleys 400 of the bottom surface 394 of the locking plate 316 preferably contact and engage with the ridges 346 and valleys 348 of the protrusion 328 in frictional or mechanical contact to precisely locate and affix the locking plate 316 to the protrusion 328. Further, as shown in FIGS. 42 and 48-53, because the protrusion ridges 350 and the locking ridges 402 are angled, as the locking plate 316 is moved from one side of the channel 380 to the other, as the locking ridges 402 seat with the protrusion ridges 350, the male plate 12 is moved into compression with the female plate 14. This compression is transferred through the male plate 12 and female plate 14 to the vertebral bone.

The width of the locking plate 316 (i.e, the distance between the parallel sides 396) is such that the locking plate 316 will fit snugly into the channel 380 formed in the upper surface 378 of the female plate 14 of the SC device 10 but still allow the locking plate 316 to move in a direction perpendicular to the parallel sides 396 within the channel 380.

Locking plate 316 has a slot 404. Slot 404 is aligned with channel 344 of the protrusion 328 and allows a locking screw 318, as explained hereafter, to pass through both the slot 404 and mate with the threaded hole 376 as described hereafter. Slot 404 is also dimensioned to conformally mate with the head 406 of screw 318 so that contact between the head 406 and slot 404 as the locking screw 318 is threaded into threaded hole 376 moves the locking ridges 402 into contact with the protrusion ridges 350.

A single large locking screw 318 is dimensioned to rotate freely within the slot 404 of the locking plate 316 activates the locking mechanism 388. In the embodiment of the invention shown in FIGS. 36-54, the locking screw 318 has a head 406, a threaded body 408 and a distal end 410 where the head 406 has a larger cross-sectional diameter than the threaded body 408.

Figure 39:
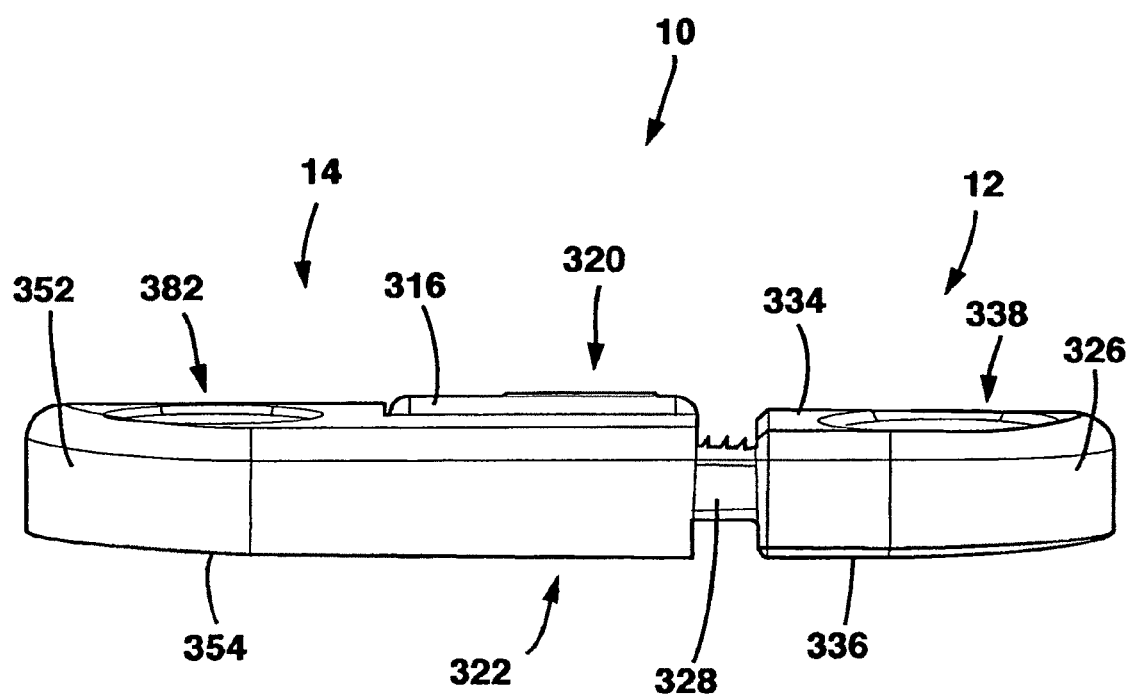
FIG. 39 is a side view of the static compression device of FIG. 36.
Figure 40:
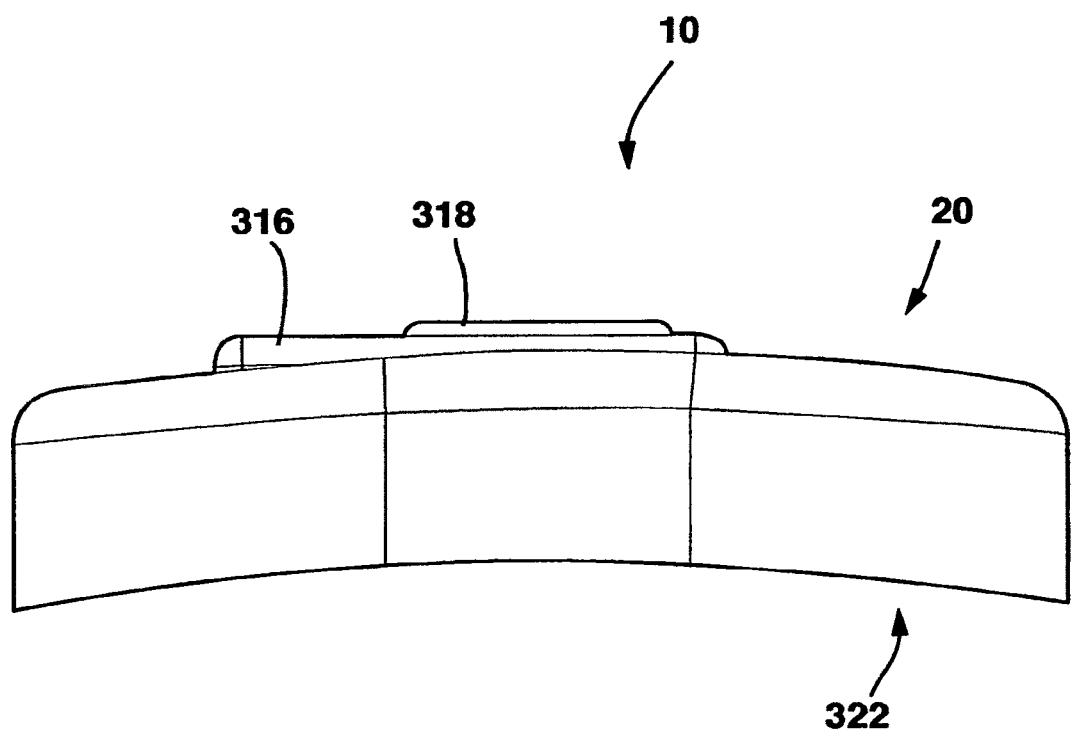
FIG. 40 is a bottom end view of the static compression device of FIG. 36.
Figure 41:
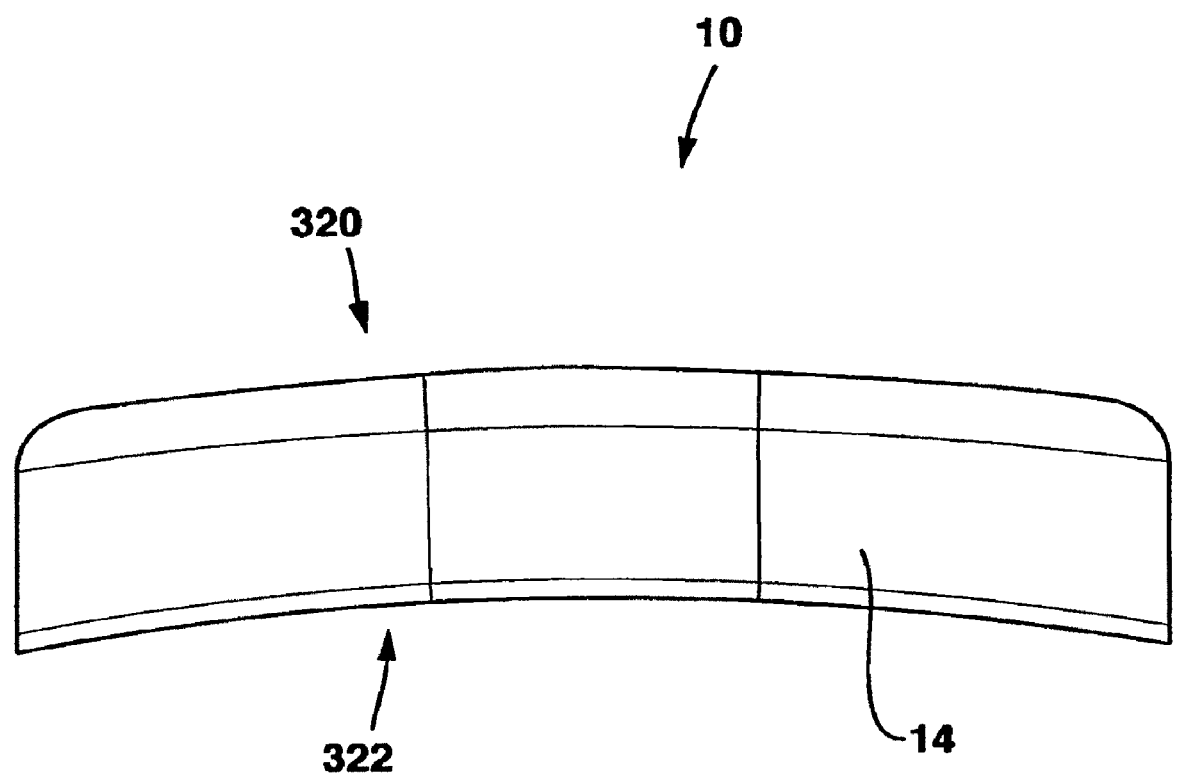
FIG. 41 is a top end view of the static compression device of FIG. 36.
Figure 42:
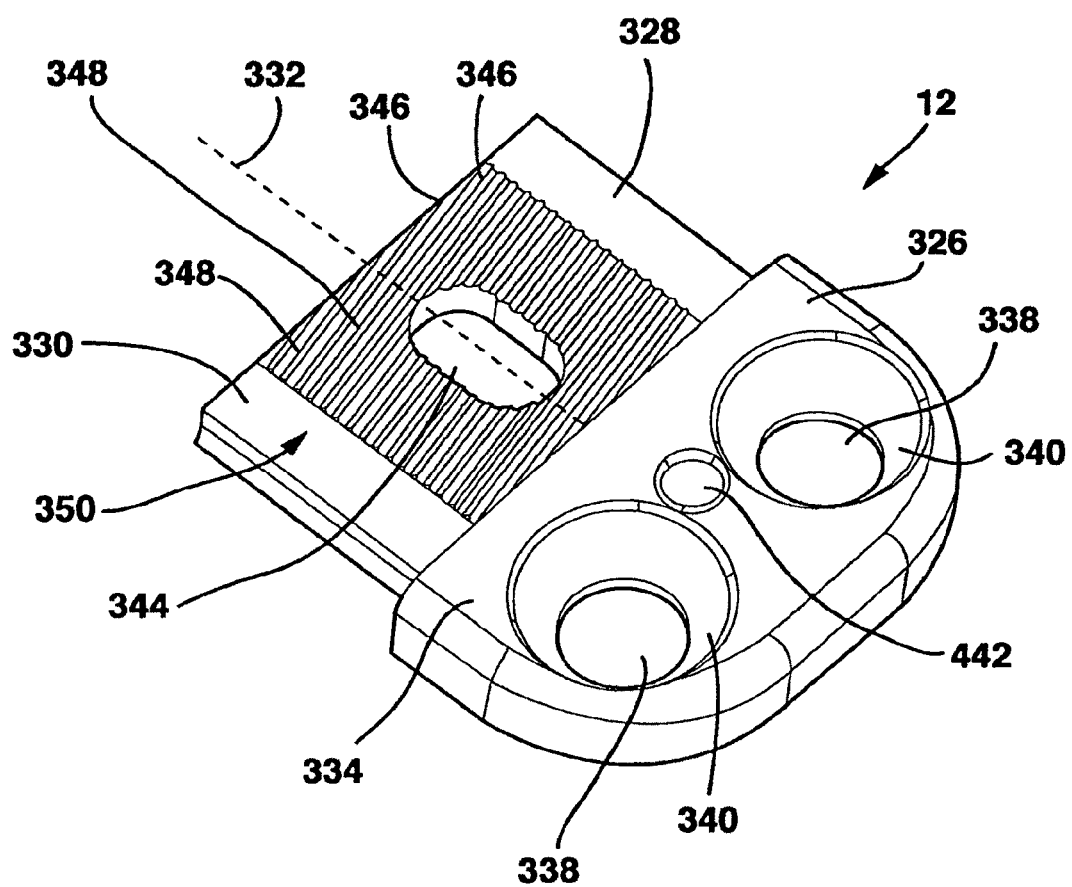
FIG. 42 is a perspective view of the male plate of the static compression device of FIG. 36.
Figure 43:
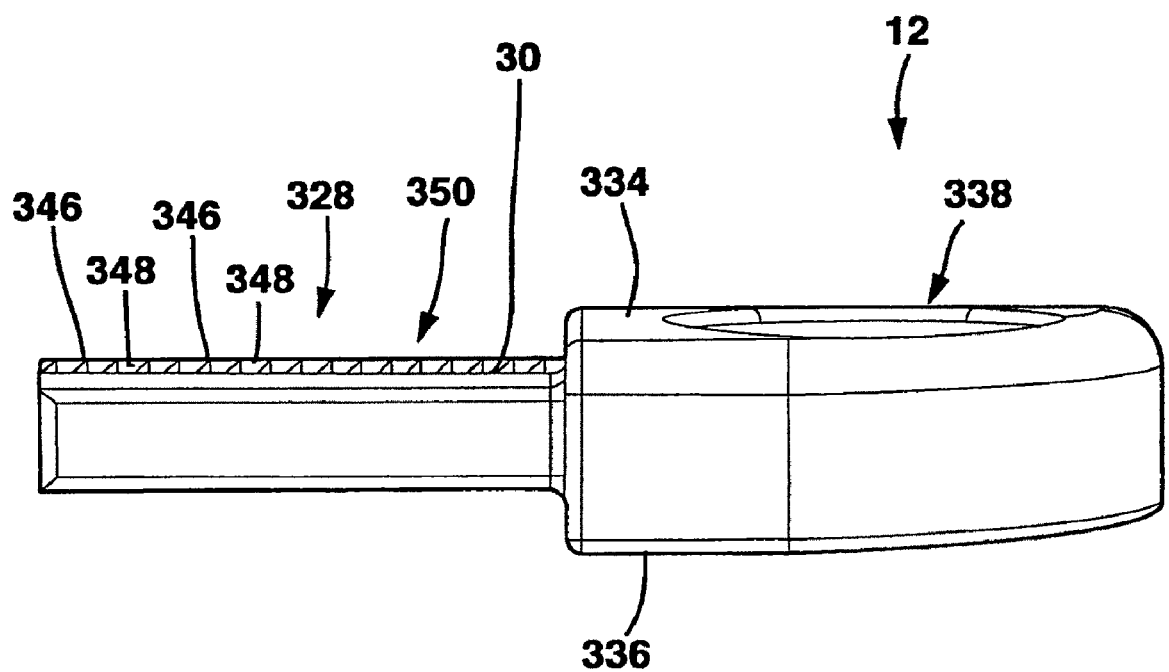
FIG. 43 is a side view of the male plate of the static compression device of FIG. 36.
Figure 44:
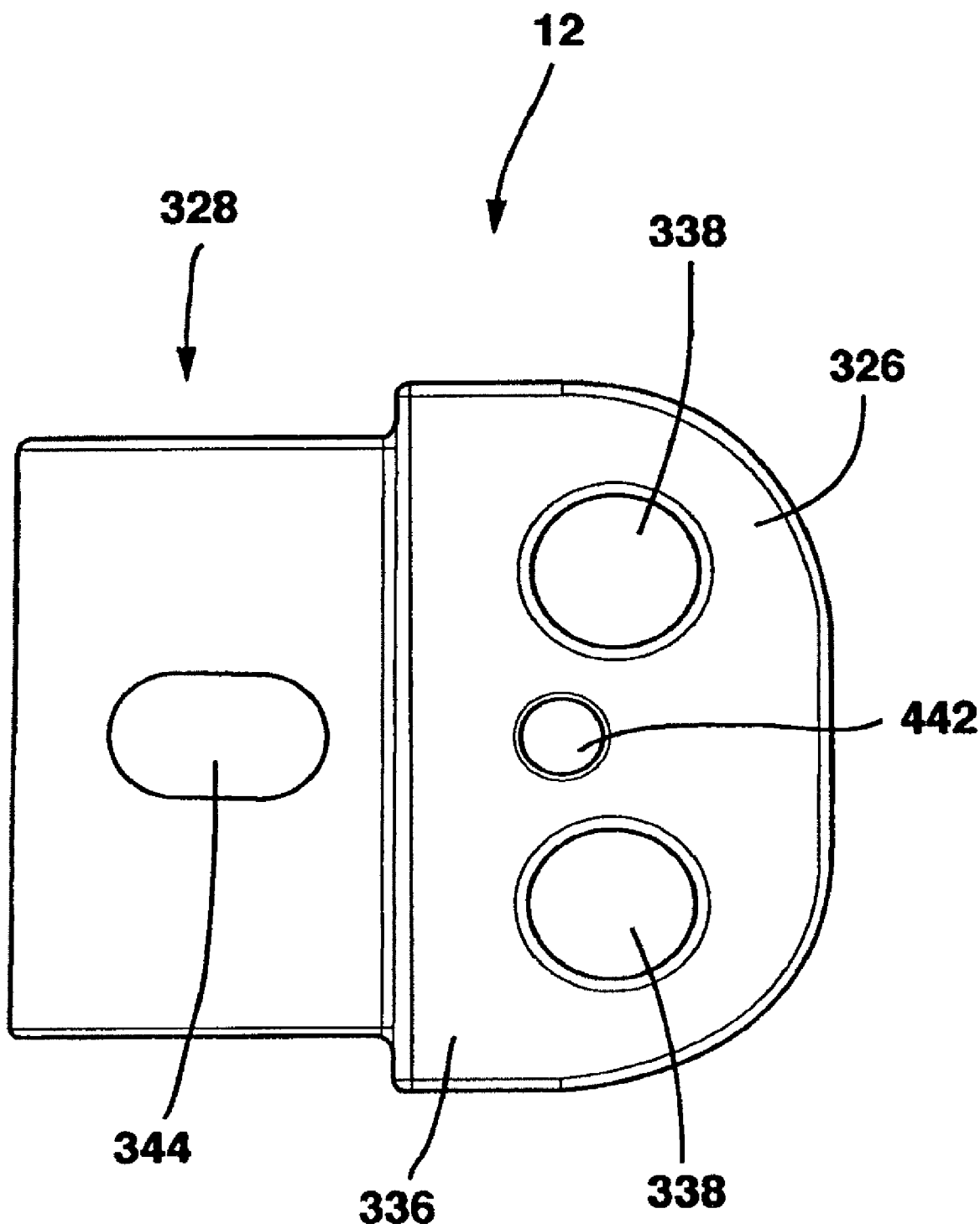
FIG. 44 is a bottom view of the male plate of the static compression device of FIG. 36.
Figure 45:
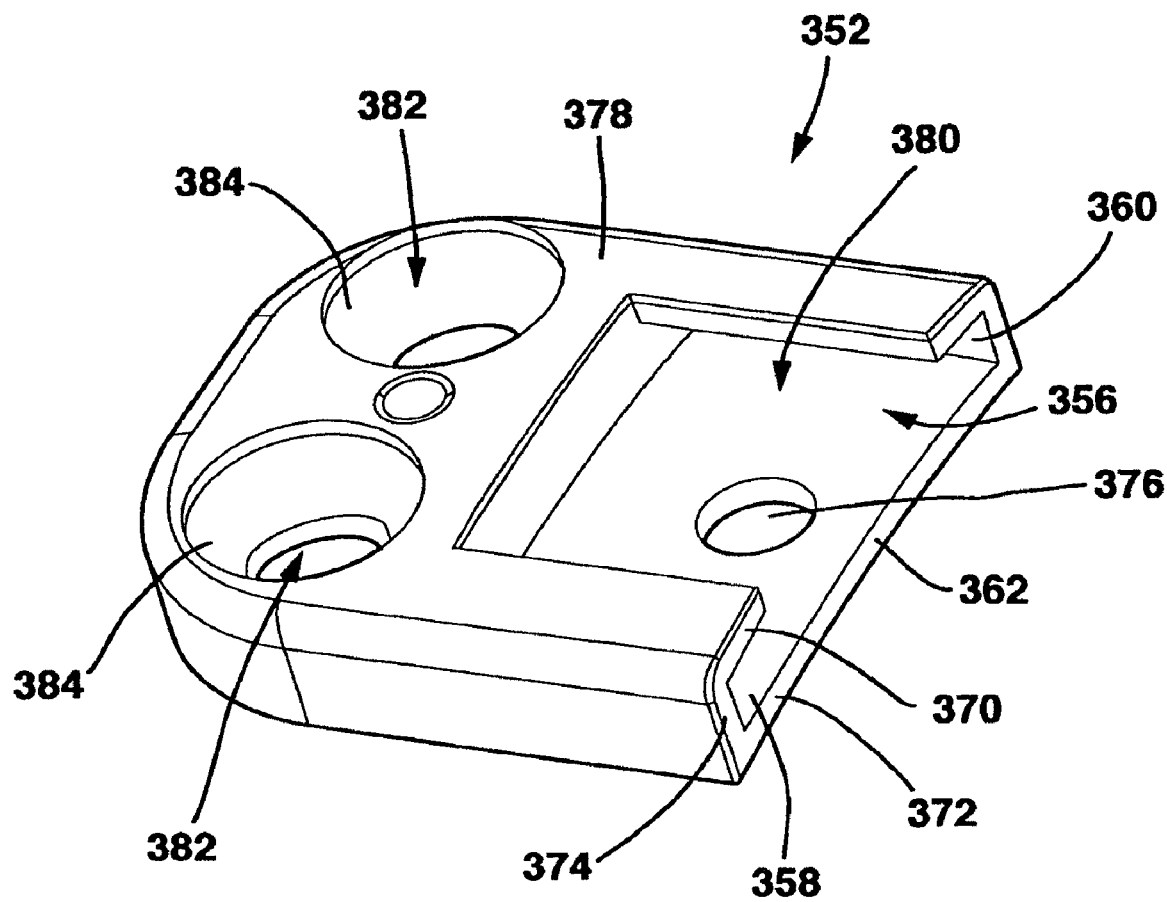
FIG. 45 is a perspective view of the female plate of the static compression device of FIG. 36.
Figure 46:
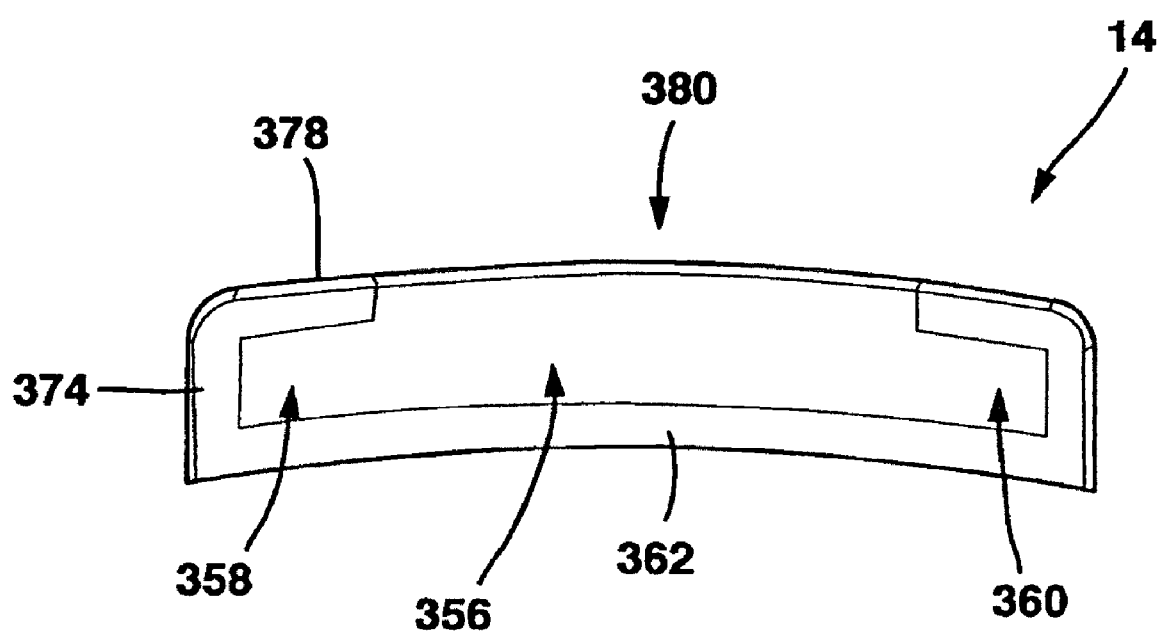
FIG. 46 is an end view of the female plate of the static compression device of FIG. 36.
Figure 47:
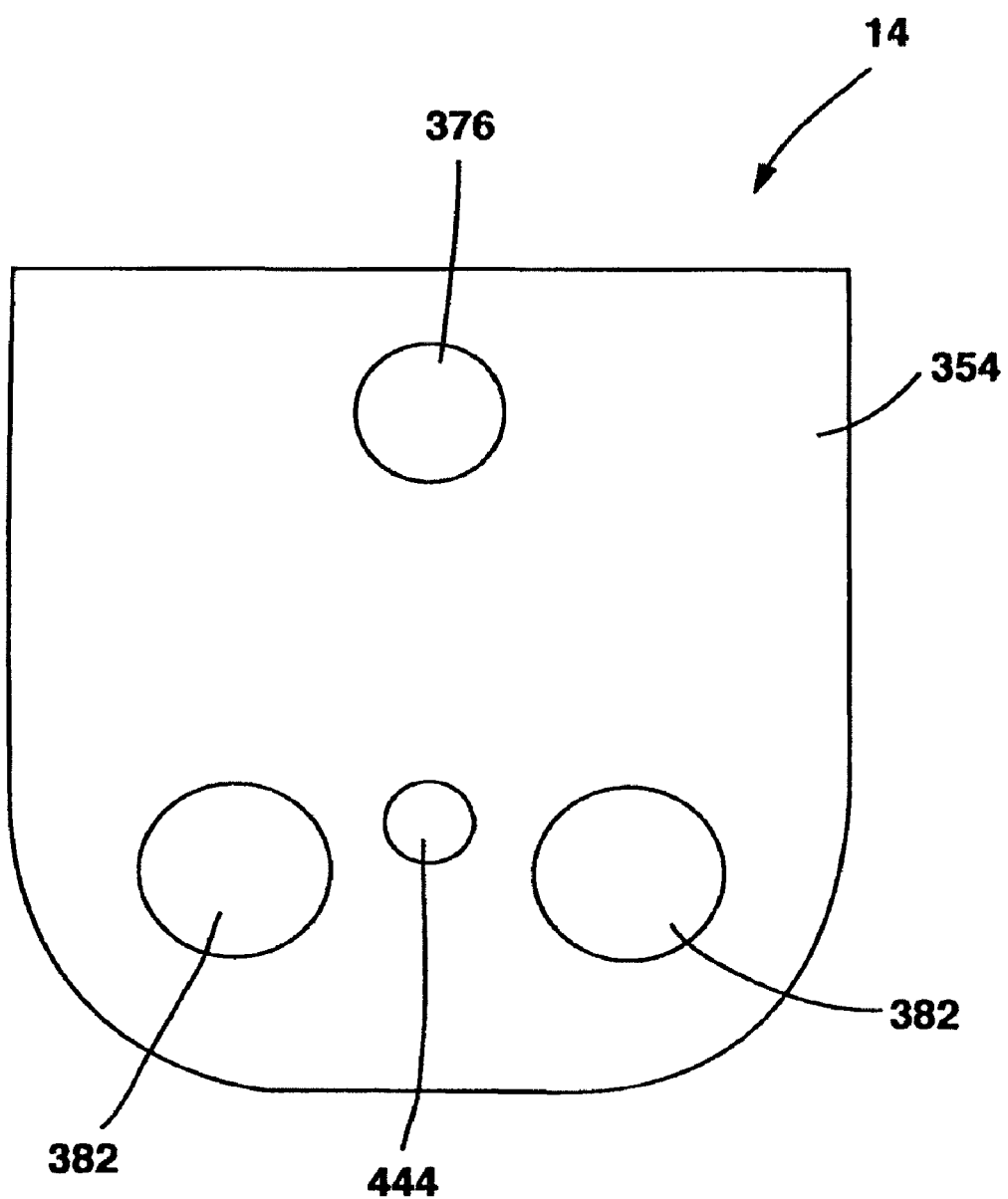
FIG. 47 is a bottom view of the female plate of the static compression device of FIG. 36.
Figure 48:
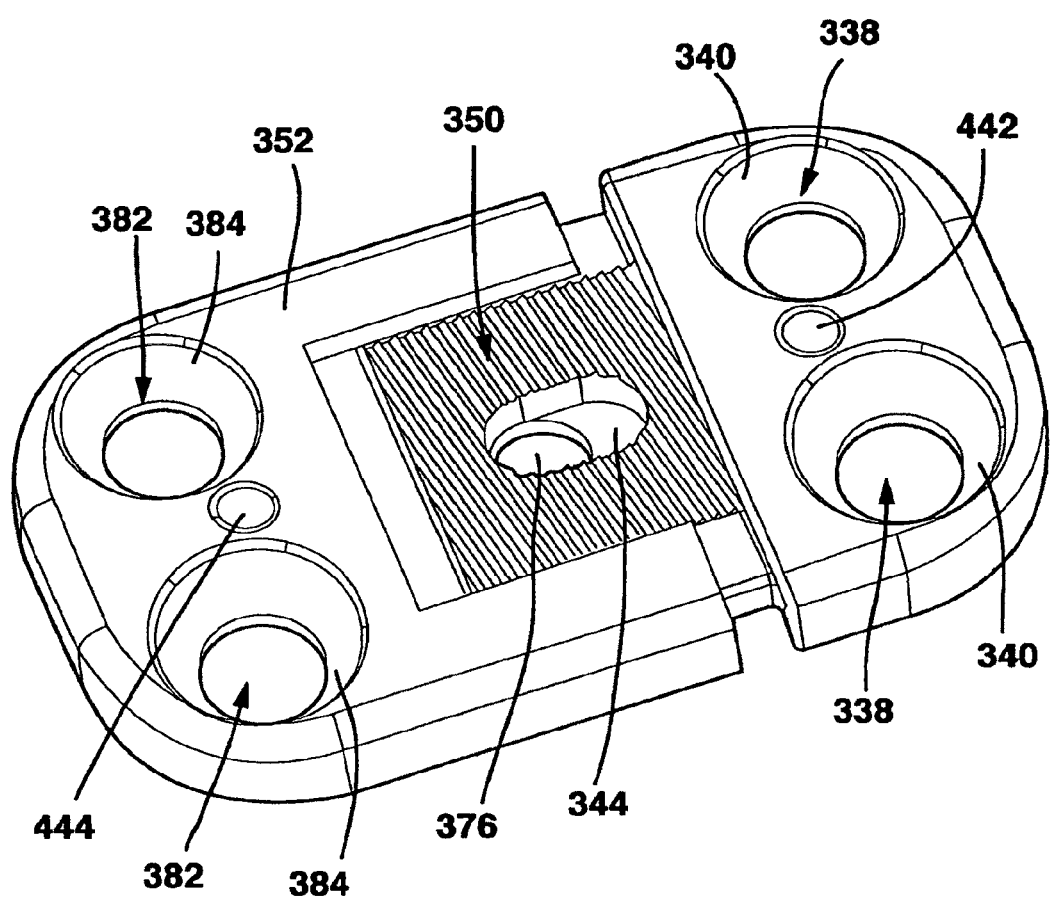
FIG. 48 is a perspective view of the male plate and female plate of the static compression device of FIG. 36 in an interconnected relationship.
Figure 49:
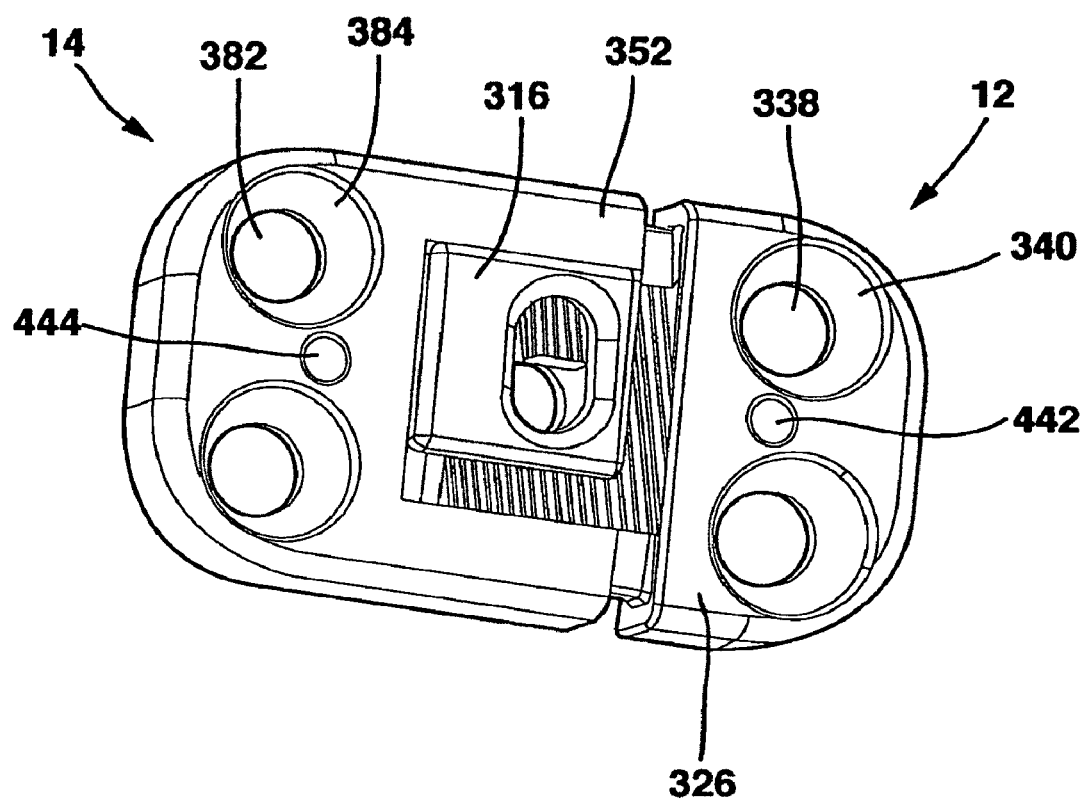
FIG. 49 is a perspective view of the male plate and female plate of the static compression device of FIG. 36 in an interconnected relationship and with the locking plate in place.
Figure 50:
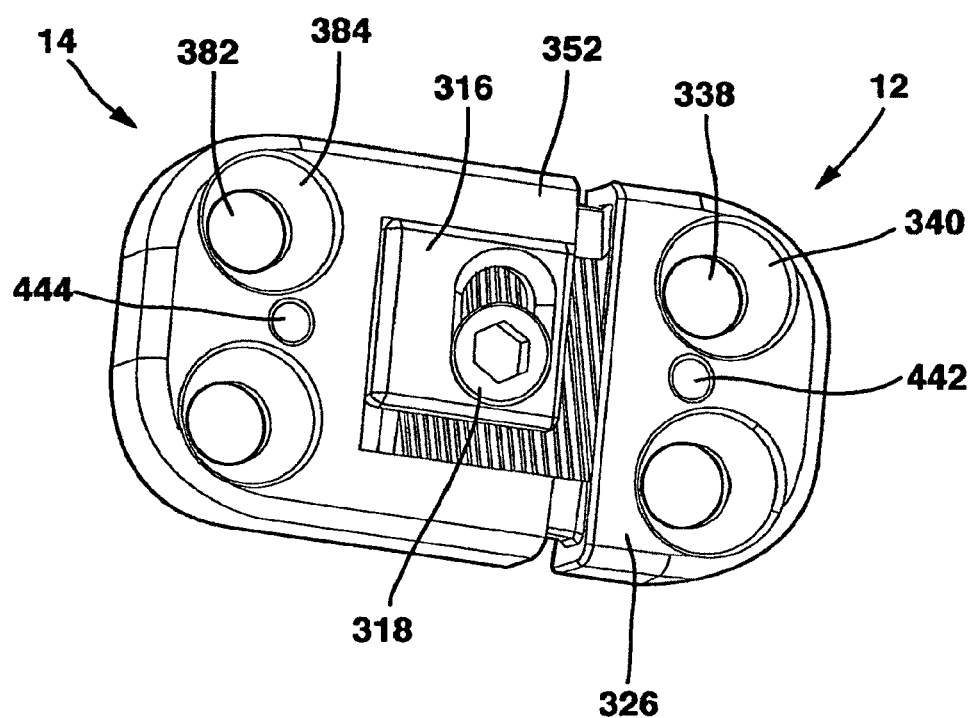
FIG. 50 is a perspective view of the male plate and female plate of the static compression device of FIG. 36 in an interconnected relationship and with the locking plate and locking screw in place.
Figure 51:
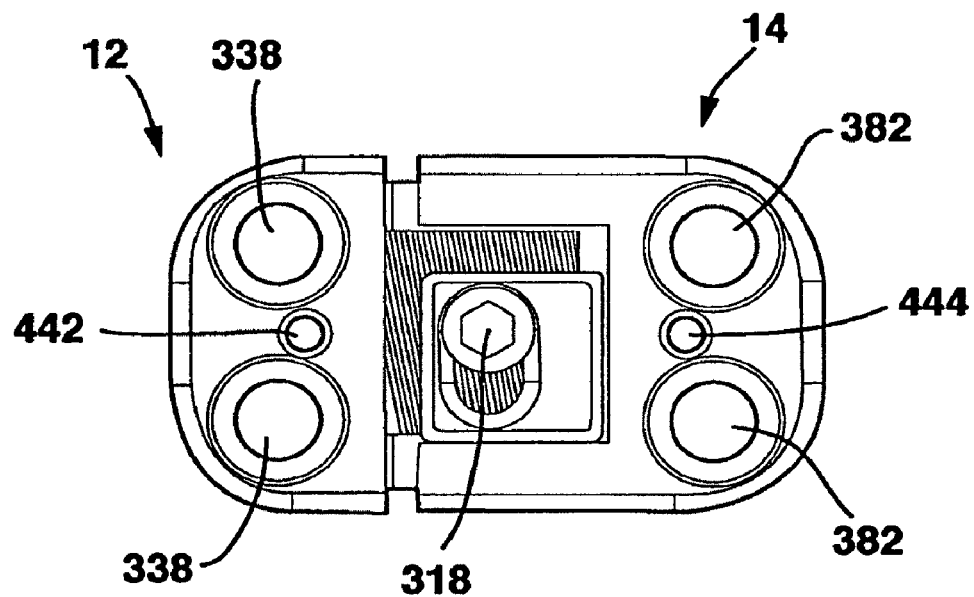
FIG. 51 is a top view of the static compression device of FIG. 36 with the male plate interconnected to the female plate and with the locking plate in place and in the uncompressed position.

In use, the protrusion 328 is inserted into the protrusion receiving channel 356 (FIGS. 39 and 48). Because protrusion receiving channel 356 is dimensioned to conformally receive protrusion 328, protrusion is precisely located and retained within the protrusion receiving channel 356. Locking plate 316 is placed on the top surface 330 of protrusion 328 within the channel 380 so that the protrusion ridges 350 come into contact with the locking ridges 402 (FIG. 49). The locking screw 318 is passed through the slot 404 so that its distal end 410 comes into contact with and is threaded into the threaded hole 376 a sufficient amount to locate the distal end 410 of the locking screw 318 in the threaded hole 376 but not a sufficient amount to secure the locking ridges 402 of the locking plate 316 into secure contact with the protrusion ridges 350 (FIGS. 50-51).

Bone screws are passed through the screw receiving holes 338 and 376 and into the vertebral bone. These bone screws are screwed into the vertebral bone until the heads of the bone screws seat into the basins 334, 378 of the male plate 12 and female plate 14, respectively.

Figure 52:
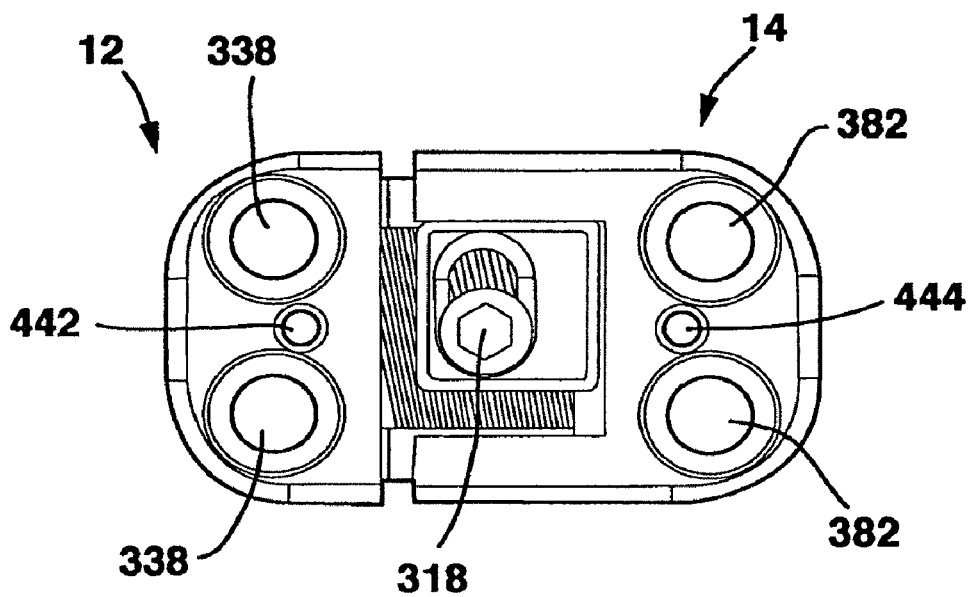
FIG. 52 is a top view of the static compression device of FIG. 36 with the male plate interconnected to the female plate and with the locking plate in place and in the compressed position.
Figure 53:
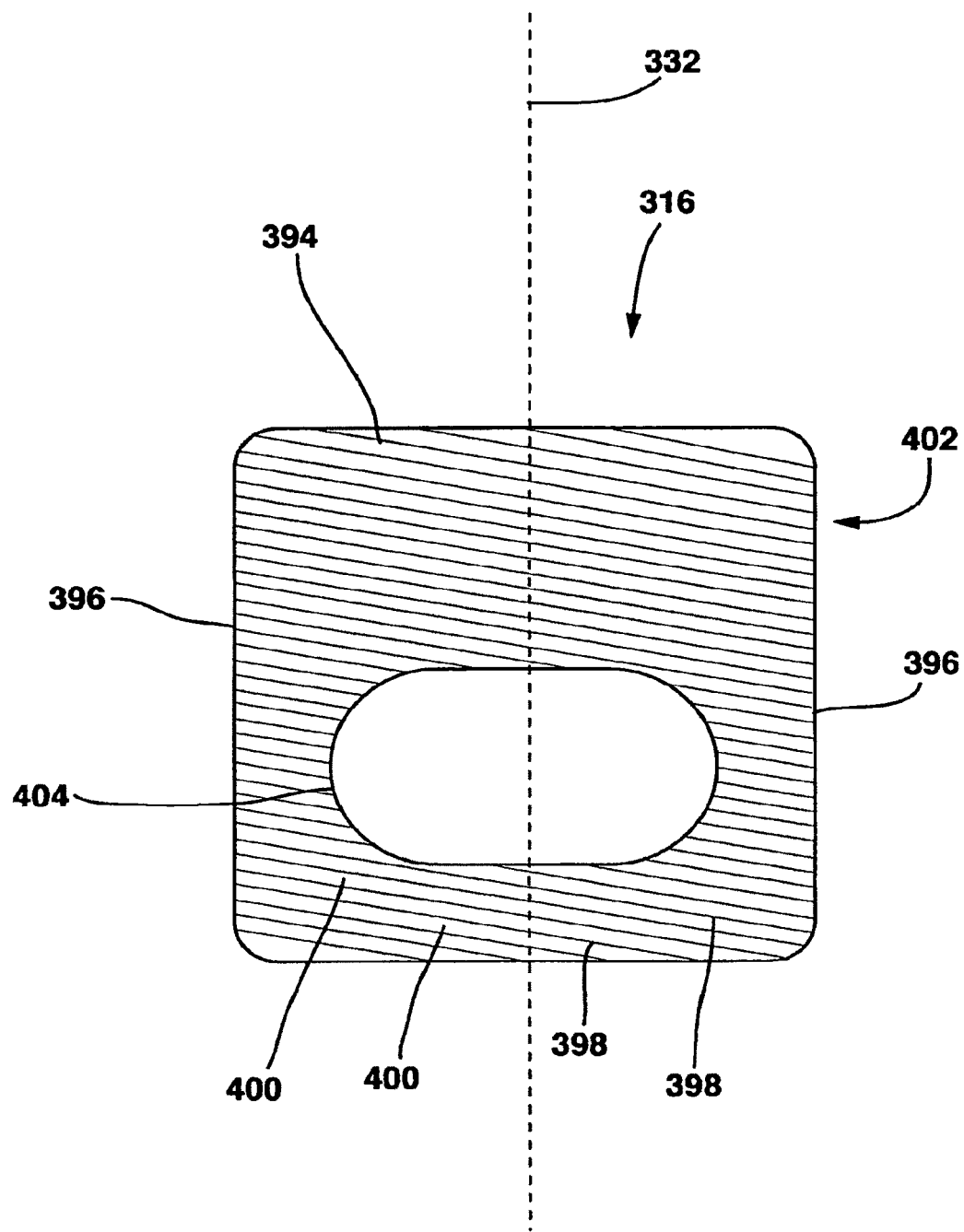
FIG. 53 is a bottom view of the locking plate of the static compression device of FIG. 36.
Figure 54:
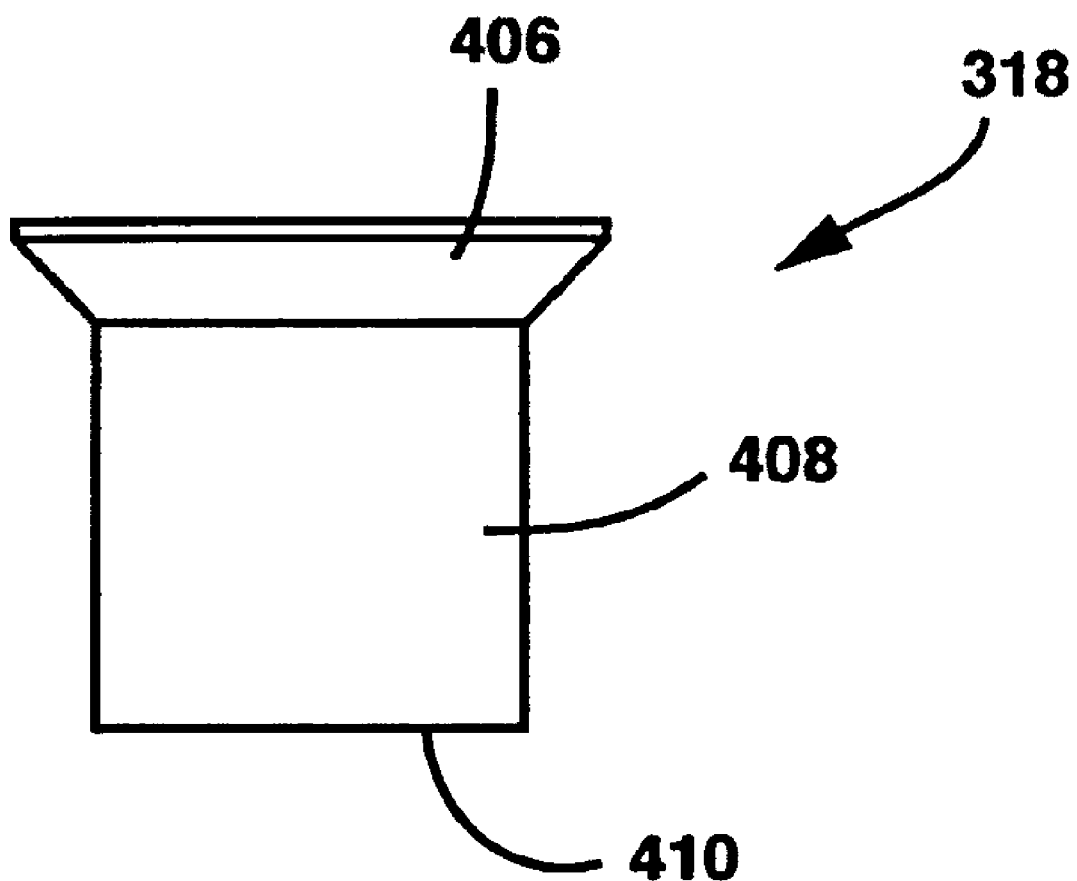
FIG. 54 is a side view of the locking screw of the static compression device of FIG. 36.

The compression device 90 is then used to apply the desired compression to the SC device 10. The pins 132 are placed in the notches 442, 444 and the handles 118, 120 are squeezed together. As a result, compression pressure is applied to the male plate 12 and female plate 14 and thereby to the vertebral bone through the bone screws. As mentioned above, where a gauge 146 is present, the amount of compressive force applied to the SC device 10 can be ascertained. Once the desired amount of compressive force is applied to the device 10, the screwdriver 160 is coupled to the head 406 of the locking screw 318. The screwdriver 160 is rotated so that the threaded body 408 of locking screw 318 is threaded into the threaded hole 376. In this process, the locking ridges 402 are brought into secure contact with the protrusion ridges 350. But, to secure an optimum fit between the locking ridges 402 and the protrusion ridges 350, it may be necessary to move the locking plate 316 from side to side within the channel 380 until they mate optimally and impart a compression on the male plate 12 and female plate 14 (FIG. 52). Once this optimal mating occurs, the screwdriver 160 is rotated further. The interaction between the head 406 and the slot 404 locks the locking plate 316 against the protrusion 328. Locking screw 318 is tightened into tight the threaded hole 376 so that the male plate 12 is securely positioned with respect to the female plate 14. Once male plate 12 is secured with respect to the female plate 14, the compression device 90 is removed.

Figure 55:
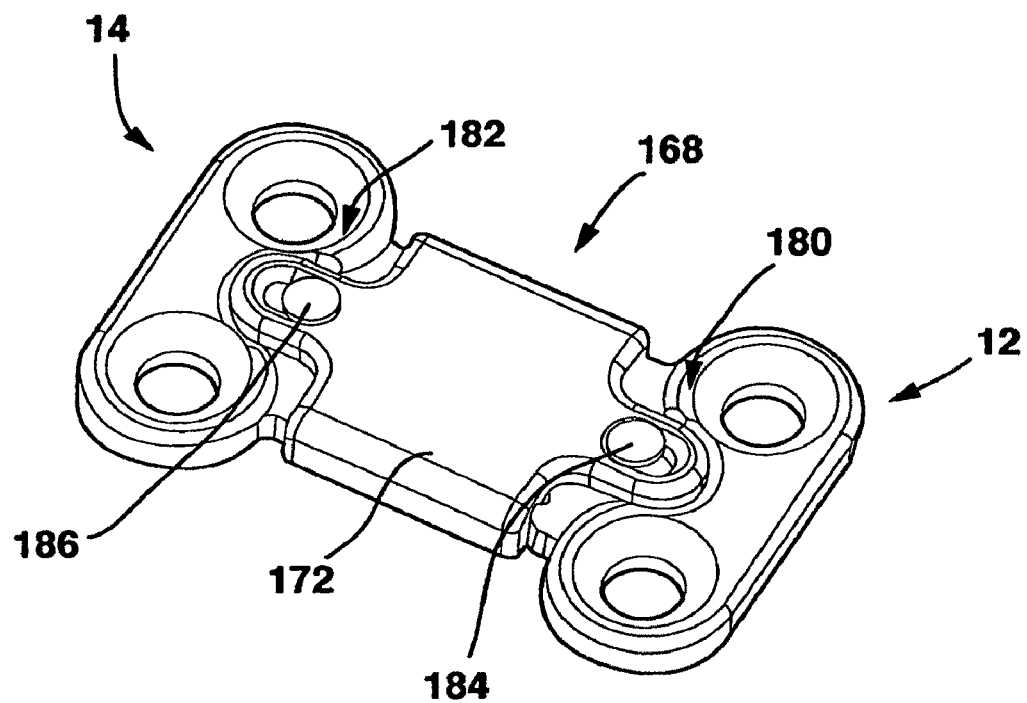
FIG. 55 is a perspective view of an alternate embodiment of the static compression device.
Figure 56:
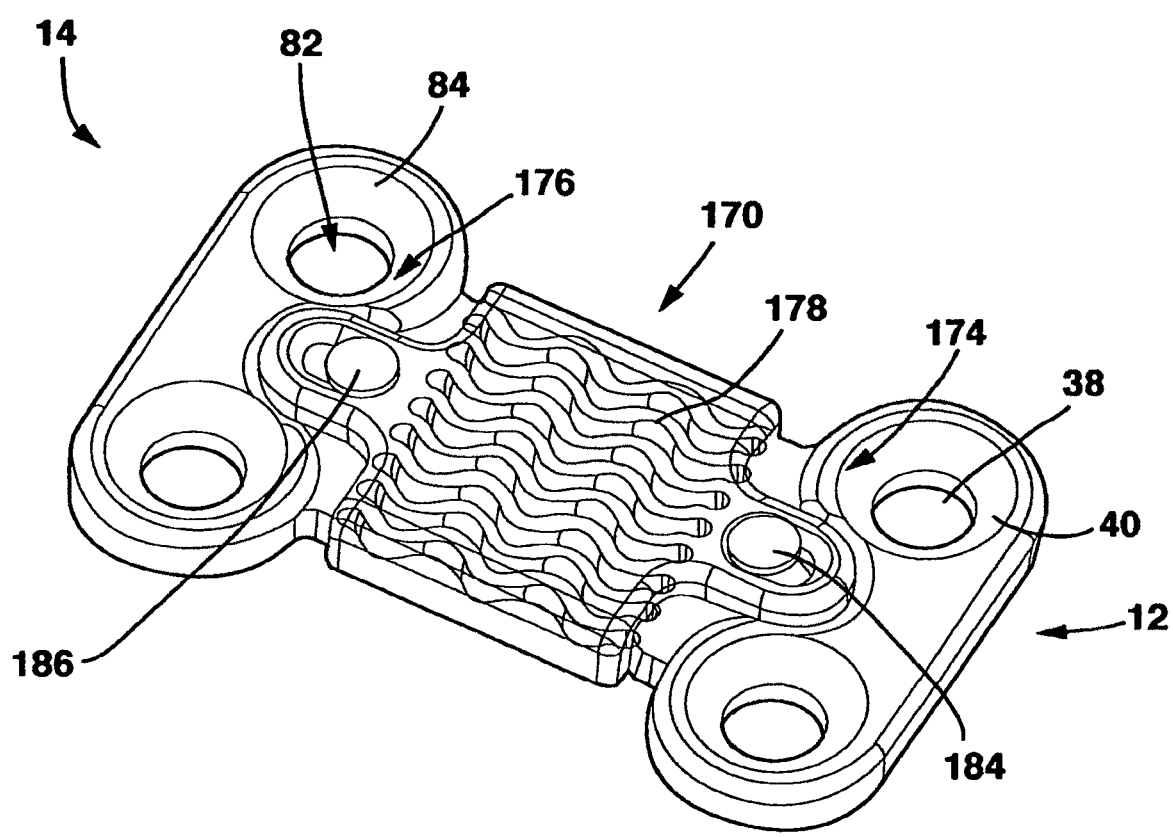
FIG. 56 is a perspective view of the static compression device of FIG. 55 with the guide plate shown in phantom.

Another alternate embodiment of the SC device 10 is shown in FIGS. 55-56. In this embodiment, the SC device 10 is as described above except that the SC device 10 has a spring mechanism 168 integral between the ends of the male plate 12 and female plate 14 that provides a near constant force applied to a fixed vertebral segment (or segments) through a standard buttressing or tension band construct. Spring mechanism 168 has three parts, a relatively flat spring plate 170, guide pins 184, 186 and a guide plate 172. Spring plate 170 has ends suitable for attaching to bone via one or more bone screws.

Spring 178 is preferable a plurality of flexible members that resist being moved in a lateral direction, in this case, in the direction of moving the one plate end 174 away from the other plate end 176. In a preferred version of this embodiment, the spring 178 is a plurality of flat serpentine shaped members made of a spring metal such as spring steel. However, the spring 178 could also be made of a single member that has spring-like attributes and could be made of materials other than metal so long as the elements of spring 178 possess the ability to resist stretching according to a linear restoring force (i.e., follows Hooke's law).

Guide plate 172 reinforces spring plate 170 and provides over extension protection as well as flexion/extension moment buffering. Over extension protection is provided by guide pins 184, 186 attached to spring plate 12 via slots and limit the extension of the spring 178. Flexion/extension is controlled by the guide plate 172 in close contact with the spring plate 12.

This embodiment of SC device 10 allows the SC device 10 to settle into position on the vertebral bone and minimize the deflection of the male plate 12 and the female plate 14 without a drastic reduction in the SC device 10's ability to provide a consistent tension force. Further, after the SC device 10 is implanted, the surgeon can determine the actual level of compression by measuring the overall change in length of the construct and applying Hooke's law to determine the relative rate of compression.

Figure 57:
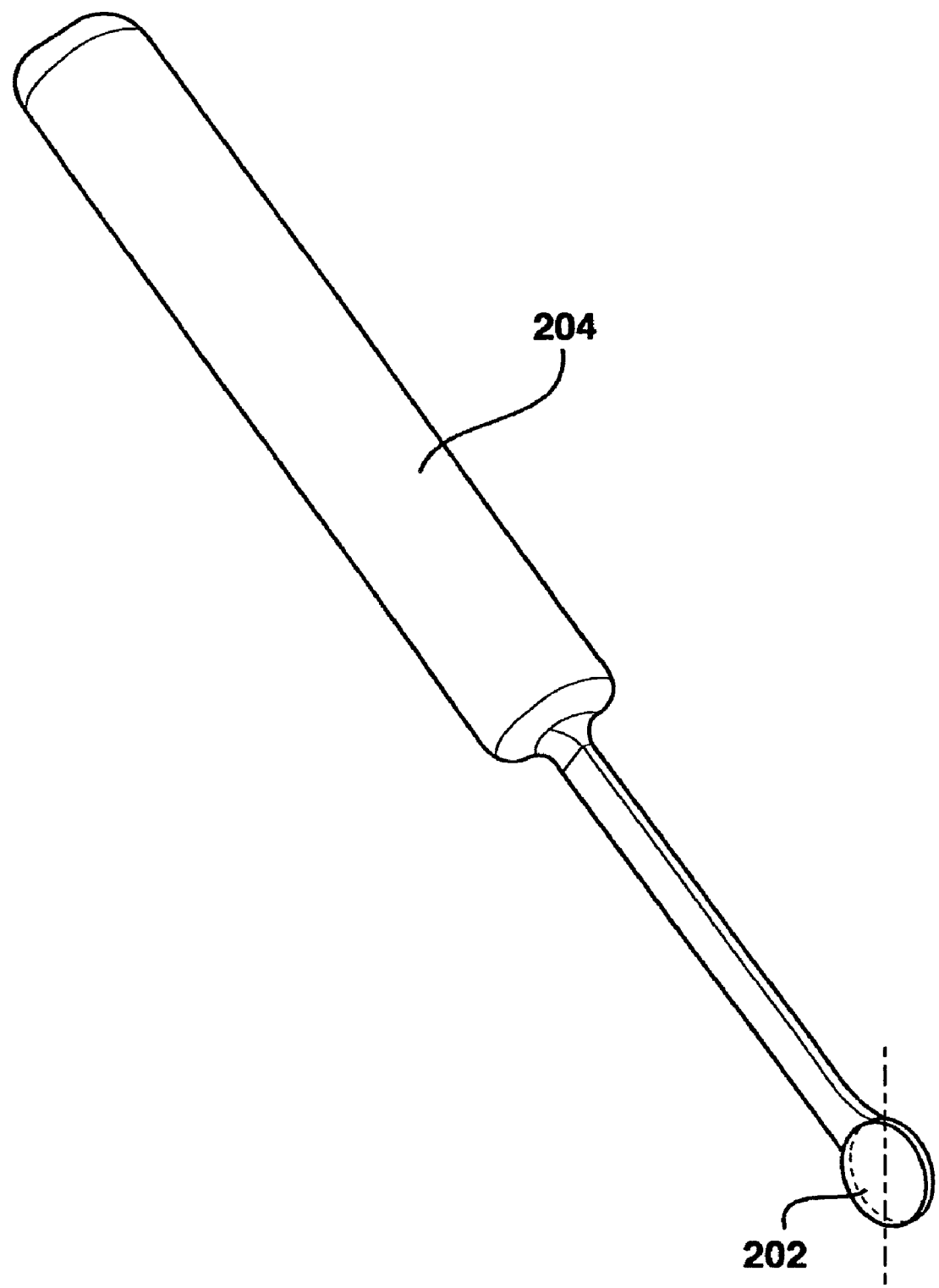
FIG. 57 is a perspective view of a series of trial spacers and corresponding handle of one aspect of the present invention.

Another feature of an embodiment of the invention shown in FIG. 57 is that of a series of trial spacers 202 that include a strain gauge capable of measuring compressive strain through electromagnetic techniques as are well understood in the art. These spacers 202 are preferably cylindrical in shape with a handle which allows them to be inserted between the vertebral bodies. The spacers are machined to have the approximate dimensions of the bone graft which is to be placed between adjacent vertebrae (in the disc space once the disc has been removed). This embodiment also includes a handle 204 attached to the spacer 202 in order to allow the surgeon ease in facilitating insertion and extraction of the spacer 202. The cylinders of the spacer 202 are preferably machined in height increments (e.g. one millimeter) in order to accommodate a variety of disc space heights.

The spacer 202 serves two purposes. First, it enables the surgeon to "size" the disc space in order to place an appropriate sized graft, in the same manner that many allograft spacers currently have "trials". Second, each spacer 202 has the characteristics of a strain gauge which is able to directly measure the "passive" force applied to that spacer 202 by the adjacent vertebral bodies, once the spacer 202 is inserted. In this way the surgeon may estimate the approximate "passive"

force which would be applied to a similar sized bone graft. The total force applied to that graft, then, would be the sum of the passive force applied to the graft (as measured by the spacer of similar dimensions) and the active force applied by the surgeon through the compression device 90. Thus, by using the strain-gauge spacer 202 in conjunction with the compression device 90, the surgeon may obtain an accurate assessment of total force applied to the graft. This is beneficial in that it allows further study of the "optimal" force which must be applied in order to reliably achieve fusion.

In all the embodiments shown, the SC device 10 is a unique device that utilizes Wolff's law to compress two or more adjacent cervical vertebrae while fusion between the vertebrae occurs by allowing static, rigid compression to be applied to interbody graft in the cervical spine. Static, rigid compression has definitively been shown to increase bony union in a long bone fracture model. Lumbar interbody fusions have been shown to heal at a higher rate than intertransverse fusions, presumably because of the constant loading of the graft. No other currently available cervical device allows for active, static compression.

Figure 58:
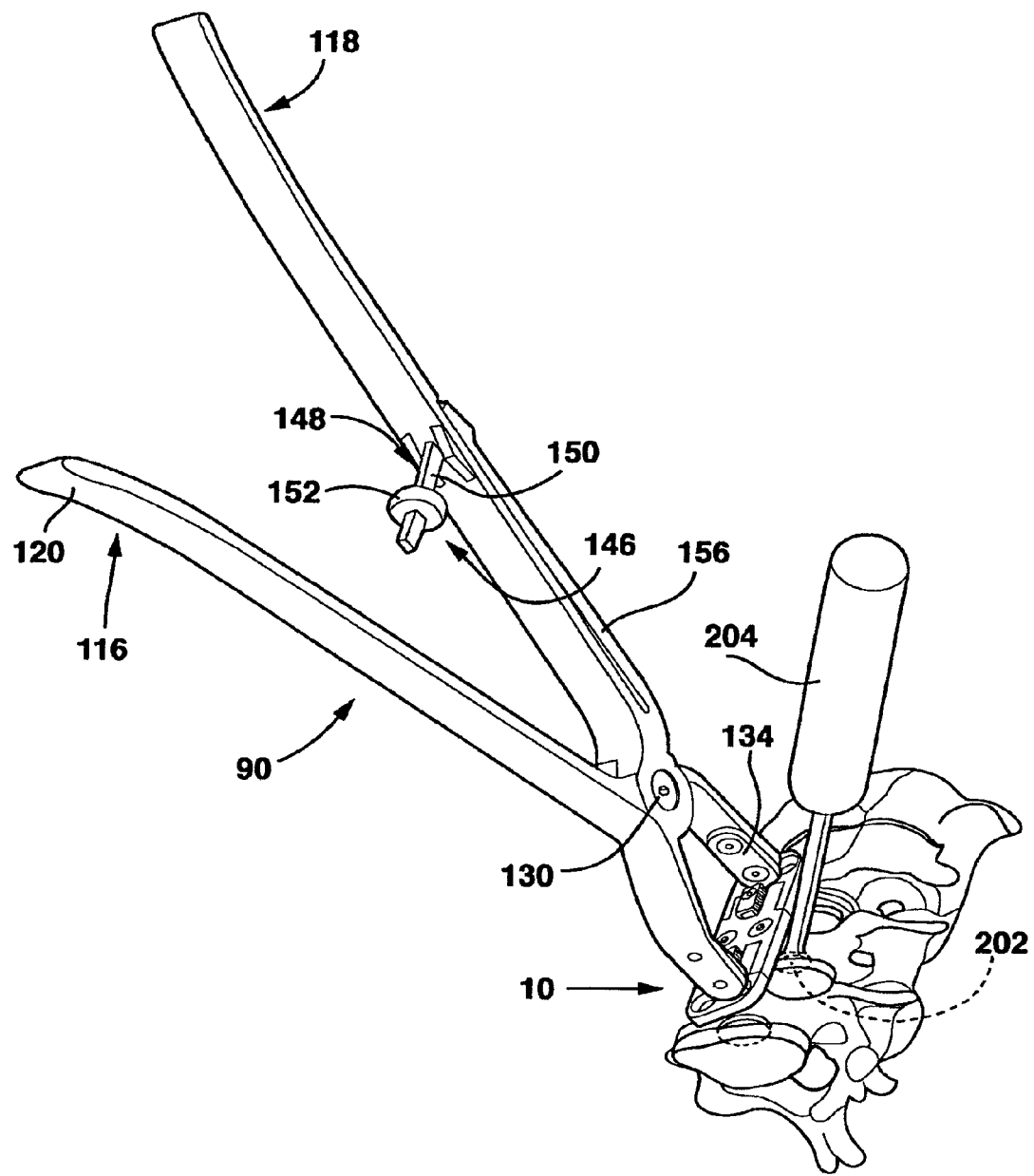
FIG. 58 is a perspective view of an embodiment of the static compression device designed to be used in the thoracic or lumbar region of the spine.
Figure 59:
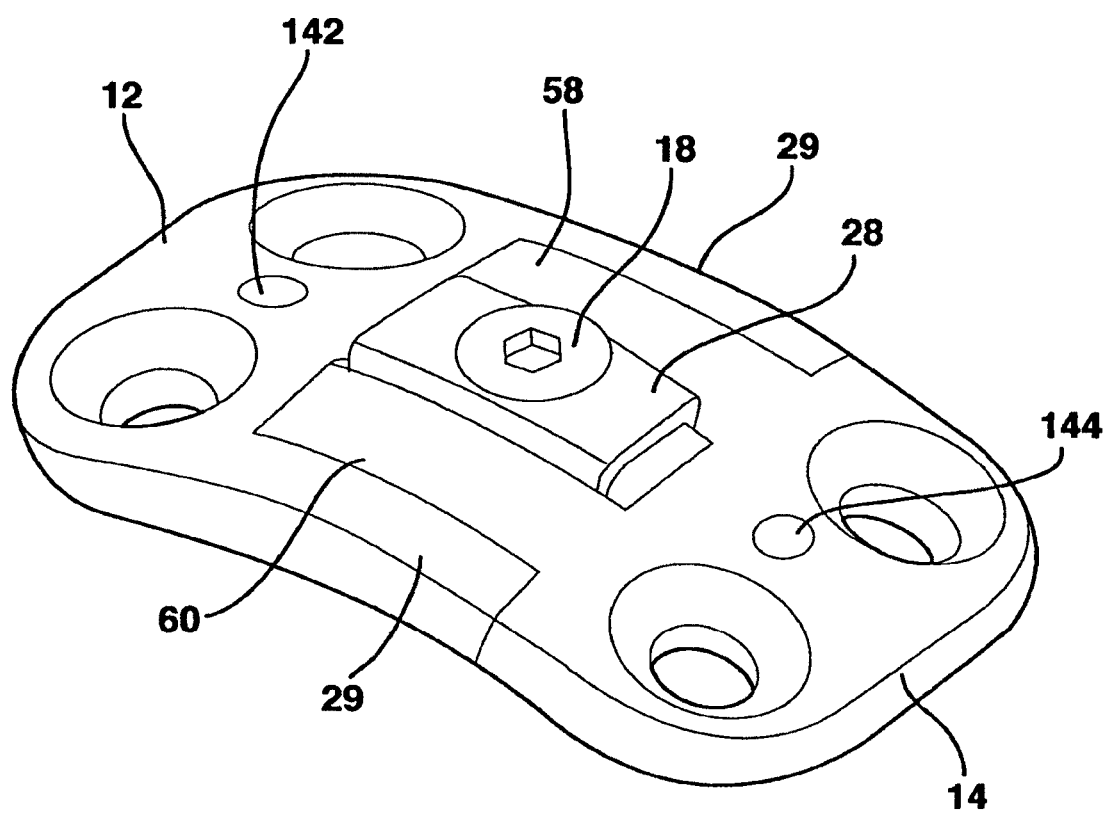
FIG. 59 is a perspective view of an embodiment of the static compression device designed to be used to treat fractures.

It should be noted that use of the SC device 10 is by no means limited to use in the cervical spine. Any of the aforementioned embodiments, in a somewhat larger version or having a curved bottom side 22 (FIG. 58) as will be clear to those skilled in the art, may be used for the same or similar purposes in the thoracic or lumbar spine, or in instances where static compression is desired outside of the spine (e.g., and without limitation, bone fractures, as for example, of long bones like the femur or bones of the skull, hip or scapula) (FIG. 59).

In the thoracic spine a larger version of the SC device 10 may be placed on the side of the thoracic spine (as opposed to the front) in order to facilitate approach to the thoracic spine and to avoid large vascular structures that reside immediately in front of the thoracic spine.

In the lumbar spine, a larger version of the SC device 10 may be placed either on the side of the spine to facilitate exposure and avoid vascular structures or directly on the front of the spine, especially at the lumbosacral junction. It is believed that in order to obtain anterior fusion at L5-S1, it is important to have a fully contoured SC device 10 (FIG. 58) that is simply comprised of a male plate 12 and a female plate 14 with a curved bottom side 22 matching the curvature of the vertebral segments in the LS-S1 region.

As mentioned above, the SC device 10 may be used to obtain union of fractures, nonunions, osteotomies and other bony defects in regions other than the spine. In the embodiment suited for use with other bones, the SC device 10 should be sized appropriately to the bone and have the option of placing more than two screws 138 on either side of the defect where union is desired (FIG. 59). The SC device 10 allows for maximum utilization of Wolff's Law to facilitate healing in that reproducible measurable compression is applied in each of these scenarios to obtain bony union.

Figure 60:
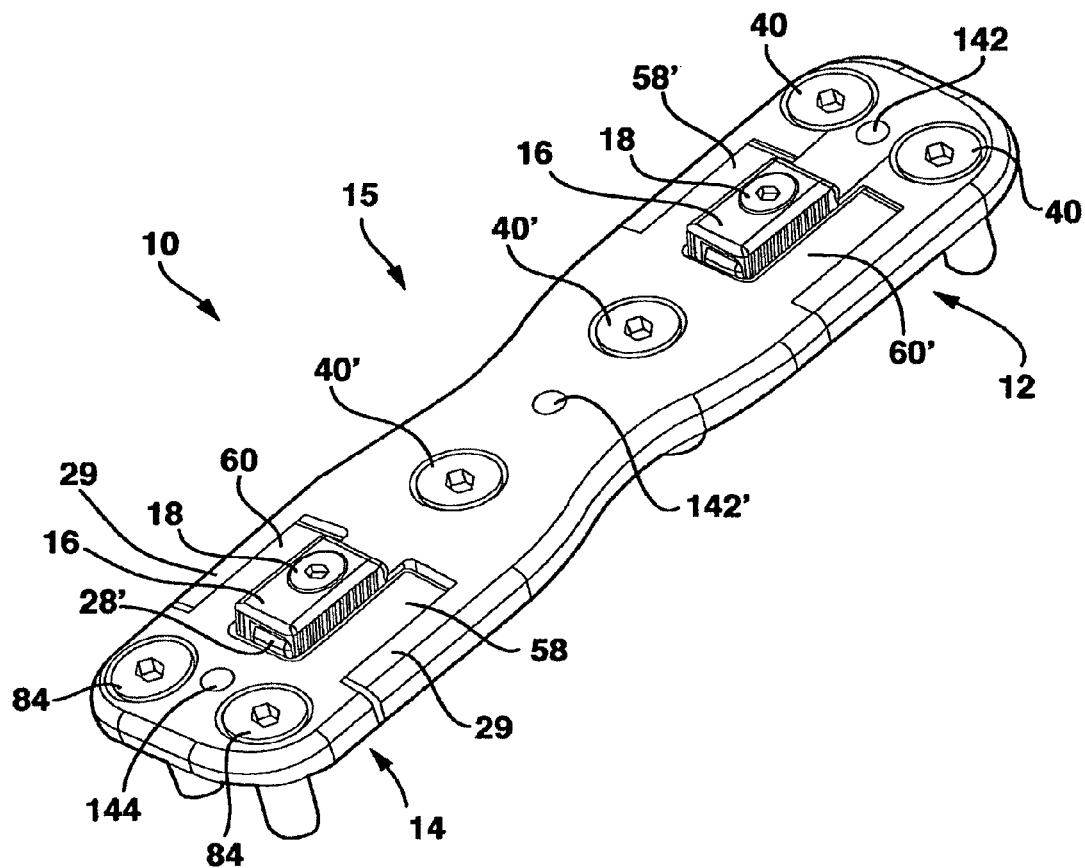
FIG. 60 is a perspective view of an embodiment of the static compression device designed to be used to treat fractures.

FIG. 60 is a perspective view of an embodiment of the static compression device designed to be used to treat fractures. The reference numerals correspond to elements described in other embodiments above. Reference numerals designated with a prime symbol simply refer to the same element disposed in a different structural configuration.

The SC device 10 described herein has the following four unique characteristics which together provide for static compression of the vertebral body-graft interface:

The use of fixed-angle screws to secure the SC device 10 to the vertebral bodies;

The use of a compression device to apply and measure the pressure applied to the vertebral bodies by the SC device 10;

The technique of using active, static compression to assist the fusion process; and The use of a locking mechanism 88 that maintains compression during the fusion process to facilitate bone growth.

These four characteristics of the SC device 10 are not currently found in any other spinal device. As a result, it is believed that the SC device 10 in any of the disclosed embodiments provides an optimal environment for spinal fusions to consolidate while preventing frequent non-unions and occasional deformities seen with the use of current dynamic plates.

The SC device 10 in several embodiments has been described in detail above. However, it is to be understood that the specific features of the various components may be modified as will occur to those skilled in the art and still fall within the parameters of the invention. For example, the specific cross-sectional shape of the protrusion 28, left and right guides 58, 60 and side protrusions 29 may be modified so long as these components interlock with each other as described herein. Further, the shape of the locking clamp 16 may be modified so long as it is able to be deformed to force frictional or mechanical contact between the various components as described above.

Further, the invention has been described as having a protrusion 28 with side protrusions 29 on a male plate 12 or interconnecting plate IS and a left guide 58 and right guide 60 on a female plate 14 or interconnecting plate 15. It is clear that the invention could also be practiced with the male plate 12 or interconnecting plate 15 having a single protrusion 28 with the female plate 14 or interconnecting plate 15 still having the left guide 58 and right guide 60. Also, the SC device 10 could have two or more protrusions 28 on the male plate 12 or interconnecting plate 15 with a corresponding number of protrusion receiving channels 56 to receive these protrusions 28 and a corresponding number of locking clamps 16.

The present invention has been described in connection with certain embodiments, configurations and relative dimensions. It is to be understood, however, that the description given herein has been given for the purpose of explaining and illustrating the invention and are not intended to limit the scope of the invention. For example, complimentary versions of the mating aspects of the SC device 10 could be formed and still be within the scope of the invention. In addition, it is clear that an almost infinite number of minor variations to the form and function of the disclosed invention could be made and also still be within the scope of the invention. Consequently, it is not intended that the invention be limited to the specific embodiments and variants of the invention disclosed. It is to be further understood that changes and modifications to the descriptions given herein will occur to those skilled in the art. Therefore, the scope of the invention should be limited only by the scope of the claims.

The invention claimed is:

1. A method of compressing adjacent vertebrae comprising the steps of:

providing active, controlled compression between a first plate having a first longitudinal axis, and a second plate having a second longitudinal axis wherein the first plate and the second plate move relative to each other when their respective axes are commonly aligned, wherein the first plate and second plate have a locking mechanism to precisely locate the first plate with respect to the second plate, and wherein the first plate is attachable to a first vertebra and the second plate is attachable to a second vertebra;
(b) attaching the first plate to a first vertebra;
(c) attaching the second plate to a second vertebra, the second vertebra being adjacent to the first vertebra;
(d) applying compression to the first and second plates so that compression is transferred to the first and second vertebra;
(e) providing the first plate with a male main body with a bottom side and a central protrusion extending away from the male main body, the first plate having a fourth longitudinal axis;
(f) providing the second plate with a female main body with a bottom side and a protrusion receiving channel adapted to conformally receive the central protrusion, the second plate having a fifth longitudinal axis, wherein the fourth longitudinal axis of the first plate is aligned with the fifth longitudinal axis of the second plate when the protrusion receiving channel receives the central protrusion; and
(g) providing a locking mechanism for allowing the first and the second plate to move with respect to each other under compression along their aligned fourth and fifth longitudinal axes when the central protrusion is engaged with the protrusion receiving channel until a desired configuration is achieved, and thereafter to prevent the first and second plate from moving with respect to each other and
(h) providing a compression device for providing active, controlled compression between the first plate and the second plate, the compression device comprising:
  (i) a first arm with a proximal end and a distal end, the proximal end having a handle and the distal end having a foot, the foot adapted to securely connect the distal end of the first arm to the first plate;
  (ii) a second arm with a proximal end and a distal end, the proximal end having a handle and the distal end having a foot, the foot adapted to securely connect the distal end of the second arm to the second plate;
  (iii) a pivot pivotally connecting the first arm to the second arm so that the first arm and second arm may move in scissors-like movement with respect to each other,
  (iv) a central processing unit capable of calculating, by running a formula, the force corresponding to electrical resistance across a strain gauge or of looking up values of force corresponding to detected electrical resistance across a strain gauge;
  (v) a display connected to the central processing unit to indicate the amount of force applied in either compression or distraction by the compression device;
  (vi) a strain gauge, connected to the central processing unit, that is secured to either the first or second arm of the compression device; and
  (vii) a turnbuckle located between and attached to either the handles of the first or second arms of the compression device or between the distal ends of the first and second arms of the compression device, wherein rotation of the turnbuckle in a first direction moves, respectively, the handles apart from each other or the distal ends apart from each other, and wherein rotation of the turnbuckle in a second direction opposite the first direction moves, respectively, the handles toward each other or the distal ends toward each other,
wherein the central processing unit measures the resistance across the strain gauge and then determines, by formula or through a lookup table, the amount of force applied in distraction or compression by the compression device, and then indicates the amount of force on the display,
whereby, a surgeon squeezing the handles on the first arm and the second arm moves the distal ends of the first arm and the second arm together thereby applying compression to the first plate and second plate, and thus to adjacent respective vertebrae, through the interaction of the feet and the respective first plate and second plate.

2. The method of claim 1, wherein the step of providing active, controlled compression between the first plate and the second plate further comprises a step of:
providing one or more interconnecting plates, the one or more interconnecting plates having a third longitudinal axis wherein the first plate, second plate, and the one or more interconnecting plates move relative to each other when their respective axes are commonly aligned, and
wherein the locking mechanism comprises a plurality of locking mechanisms disposed so that the first plate, the second plate, and the one or more interconnecting plates each connect via the plurality of locking mechanisms to precisely locate the first plate with respect to the one or more interconnecting plates, the one or more interconnecting plates with respect to each other, and the second plate with respect to the one or more interconnecting plates, and
wherein the one or more interconnecting plates are attached to one or more vertebrae, respectively, between the first and second vertebrae.

3. The method of claim 1, further comprising the step of:
(i) providing a zeroing function system comprising means for communicating to the central processing unit that sufficient distraction has been applied by the compression device to vertebrae connected to the compression device to establish lift-off of vertebrae to which the compression device is attached.

4. The method of claim 3, further comprising the steps of:
(j) displaying on the display, under direction by the central processing unit, a null value upon communication to the central processing unit that sufficient distraction has been applied by the compression device to vertebrae connected to the compression device to establish lift-off of vertebrae to which the compression device is attached; and
(k) displaying on the display, under direction by the central processing unit, the value of the force applied anatomically and by the compression device to vertebrae to which the compression device is attached.

5. The method of claim 1, wherein the step of providing a compression device further comprises the step of providing a zeroing function system comprising means for communicating to the central processing unit that no distraction has been applied by the compression device to vertebrae to which the compression device is attached.

6. The method of claim 5, further comprising the steps of:
(l) displaying on the display, under direction by the central processing unit, a null value upon communication to the central processing unit that no distraction has been applied by the compression device to vertebrae to which the compression device is attached; and
(m) displaying on the display, under direction by the central processing unit, the value of the force applied through distraction or compression by the compression device to vertebrae to which the compression device is attached.

7. The method of claim 1, wherein the locking mechanism is selectable between locked and unlocked configurations, to operate in either static or dynamic modes, respectively.

8. The method of claim 1, comprising the further step of:
(n) fixedly locking the first and second plates with respect to one another.

9. The method of claim 8, comprising the further step of:
(o) removing the active, controlled compression between the first and second plates.

10. A method of compressing two or more adjacent pieces of bone comprising the steps of:
(a) providing a device for providing active, controlled compression between a first plate having a longitudinal axis and a second plate having a longitudinal axis wherein the first plate and the second plate move relative to each other when their respective longitudinal axes are commonly aligned and wherein the first plate and second plate have a locking mechanism to precisely locate the first plate with respect to the second plate and wherein the first plate is attachable to a first piece of bone and the second plate is attachable to a second piece of bone;
(b) attaching the first plate to a first piece of bone;
(c) attaching the second plate to a second piece of bone the second piece of bone being adjacent to the first piece of bone; and
(d) applying compression to the device so that compression is transferred to the first and second pieces of bone,
wherein the device comprises:
(i) a first arm with a proximal end and a distal end, the proximal end having a handle and the distal end having a foot, the foot adapted to securely connect the distal end of the first arm to the first plate;
(ii) a second arm with a proximal end and a distal end, the proximal end having a handle and the distal end having a foot, the foot adapted to securely connect the distal end of the second arm to the second plate;
(iii) a pivot pivotally connecting the first arm to the second arm so that the first arm and second aim may move in scissors-like movement with respect to each other,
(iv) a central processing unit capable of calculating, by running a formula, the force corresponding to electrical resistance across a strain gauge or of looking up values of force corresponding to detected electrical resistance across a strain gauge;
(v) a display connected to the central processing unit to indicate the amount of force applied in either compression or distraction by the compression device;
(vi) a strain gauge, connected to the central processing unit, that is secured to either the first or second arm of the compression device; and
(vii) a turnbuckle located between and attached to either the handles of the first or second arms of the compression device or between the distal ends of the first and second arms of the compression device, wherein rotation of the turnbuckle in a first direction moves, respectively, the handles apart from each other or the distal ends apart from each other, and wherein rotation of the turnbuckle in a second direction opposite the first direction moves, respectively, the handles toward each other or the distal ends toward each other, and
wherein the central processing unit measures the resistance across the strain gauge and then determines, by formula or through a lookup table, the amount of force applied in distraction or compression by the compression device, and then indicates the amount of force on the display,
whereby, a surgeon squeezing the handles on the first arm and the second arm moves the distal ends of the first arm and the second arm together thereby applying compression to the first plate and second plate, and thus to adjacent respective vertebrae, through the interaction of the feet and the respective first plate and second plate.

11. The method of claim 10, further comprising:
providing one or more interconnecting plates, each of the one or more interconnecting plates having a longitudinal axis;
the first plate, the second plate, and the one or more interconnecting plates move relative to each other when their respective longitudinal axes are commonly aligned;
the first plate, the second plate, and the one or more interconnecting plates each connect to a locking mechanism to precisely locate the first plate with respect to the one or more interconnecting plates, the one or more interconnecting plates with respect to another of the one or more interconnecting plates, and the second plate with respect to the one or more interconnecting plates; and
wherein the one or more interconnecting plates are attachable to one or more pieces of bone, respectively, between the first and second pieces of bone.

12. The method of claim 10, wherein the step of providing further comprises the steps of:
(e) providing the first plate with a male main body including a bottom side thereof, the first plate further having a longitudinal axis and a central protrusion extending away from the male main body;
(f) providing the second plate with a female main body including a bottom side thereof, the second plate further having a longitudinal axis and a protrusion receiving channel adapted to conformally receive the central protrusion of the first plate; and
(g) providing a locking mechanism for allowing the first and second plates to move with respect to each other under compression along a common longitudinal axis when the central protrusion is engaged with the protrusion receiving channel until a desired configuration is achieved and thereafter to prevent the first and second plate from moving with respect to each other,
wherein the longitudinal axis of the first plate is aligned with the longitudinal axis of the second plate, when the protrusion receiving channel receives the central protrusion, to form the common longitudinal axis.

* * * * *